US011596687B2

(12) United States Patent
Cook et al.

(10) Patent No.: US 11,596,687 B2
(45) **Date of Patent: *Mar. 7, 2023**

(54) RECOMBINANT NON-PATHOGENIC MAREK'S DISEASE VIRUS CONSTRUCTS ENCODING INFECTIOUS LARYNGOTRACHEITIS VIRUS AND INFECTIOUS BURSAL DISEASE VIRUS ANTIGENS

(71) Applicant: Intervet Inc., Madison, NJ (US)

(72) Inventors: Stephanie Cook, Omaha, NE (US); Mohamad Morsey, Omaha, NE (US); Ian Tarpey, St. Ives (GB); Iwan Verstegen, Boxmeer (NL); Paulus Jacobus Antonius Sondermeijer, Boxmeer (NL); Paul Vermeij, St. Anthonis (NL)

(73) Assignee: Intervet Inc., Madison, NJ (US)

(*) Notice: Subject to any disclaimer, the term of this patent is extended or adjusted under 35 U.S.C. 154(b) by 1117 days.

This patent is subject to a terminal disclaimer.

(21) Appl. No.: 16/309,297

(22) PCT Filed: Jun. 15, 2017

(86) PCT No.: PCT/EP2017/064662

§ 371 (c)(1),
(2) Date: Dec. 12, 2018

(87) PCT Pub. No.: WO2017/216287

PCT Pub. Date: Dec. 21, 2017

(65) Prior Publication Data

US 2022/0125915 A1 Apr. 28, 2022

Related U.S. Application Data

(60) Provisional application No. 62/351,471, filed on Jun. 17, 2016.

(51) Int. Cl.

| | |
|---|---|
| ***A61K 39/245*** | (2006.01) |
| ***C12N 7/00*** | (2006.01) |
| ***A61P 31/22*** | (2006.01) |
| *A61K 39/00* | (2006.01) |

(52) U.S. Cl.

CPC ............ *A61K 39/245* (2013.01); *A61P 31/22* (2018.01); *C12N 7/00* (2013.01); *A61K 2039/5256* (2013.01); *A61K 2039/552* (2013.01); *A61K 2039/70* (2013.01)

(58) Field of Classification Search

CPC ...... A61K 2039/5256; A61K 2039/552; A61K 2039/70; A61K 39/12; A61P 31/14; C12N 15/86

See application file for complete search history.

(56) References Cited

U.S. PATENT DOCUMENTS

| | | | | |
|---|---|---|---|---|
| 5,187,087 | A | 2/1993 | Sondermeijer et al. | |
| 5,733,554 | A | 3/1998 | Audonnet et al. | |
| 5,830,745 | A | 11/1998 | Hock et al. | |
| 5,834,305 | A | 11/1998 | Cochran et al. | |
| 5,853,733 | A | 12/1998 | Cochran et al. | |
| 5,928,648 | A | 7/1999 | Cochran | |
| 5,961,982 | A | 10/1999 | Cochran | |
| 5,965,138 | A | 10/1999 | Cochran et al. | |
| 5,980,906 | A | 11/1999 | Audonnet et al. | |
| 6,121,043 | A | 9/2000 | Cochran et al. | |
| 6,183,753 | B1 | 2/2001 | Cochran et al. | |
| 6,299,882 | B1 | 10/2001 | Junker | |
| 6,875,856 | B2 | 4/2005 | Wild et al. | |
| 6,913,751 | B2 | 7/2005 | Cochran et al. | |
| 8,932,604 | B2 | 1/2015 | Cook et al. | |
| 9,114,108 | B2 | 8/2015 | Bublot et al. | |
| 9,409,954 | B2 | 8/2016 | Cook et al. | |
| 9,555,016 | B2 | 1/2017 | Makridakis | |
| 9,555,096 | B2 | 1/2017 | Bublot et al. | |
| 9,770,502 | B2 | 9/2017 | Bublot et al. | |
| 10,188,720 | B2 | 1/2019 | Esaki et al. | |
| 10,308,956 | B2 | 6/2019 | Verstegen et al. | |
| 10,323,257 | B2 | 6/2019 | Bublot et al. | |
| 10,655,146 | B2 | 5/2020 | Esaki et al. | |
| 10,813,991 | B2 | 10/2020 | Reddy et al. | |
| 10,822,620 | B2 | 11/2020 | Bublot et al. | |
| 11,058,761 | B2 | 7/2021 | Mebatsion et al. | |
| 11,123,425 | B2 | 9/2021 | Fujisawa et al. | |
| 11,229,698 | B2 * | 1/2022 | Cook .................. | A61K 39/255 |

(Continued)

FOREIGN PATENT DOCUMENTS

| | | | |
|---|---|---|---|
| CN | 1472315 | A | 2/2004 |
| CN | 103589693 | A | 2/2014 |
| CN | 103874508 | A | 6/2014 |
| CN | 103890183 | A | 6/2014 |
| EP | 728842 | A2 | 8/1996 |
| EP | 1298139 | B1 | 5/2007 |
| EP | 2644702 | A1 | 10/2013 |

(Continued)

OTHER PUBLICATIONS

Bobrovskaya, Irina Vladimirovna, Antigenic Properties of Infectious and Thermoinactivated Vaccine Preparations of Marek's Disease Virus Strains, Shchyolkovo, 2000, 1-28, N/A.

(Continued)

*Primary Examiner* — Bao Q Li
(74) *Attorney, Agent, or Firm* — Michael D. Davis

(57) ABSTRACT

The present invention discloses novel recombinant multivalent non-pathogenic Marek's Disease virus constructs that encode and express both Infectious Laryngotracheitis Virus protein antigens and an Infectious Bursal Disease virus protein antigen, and methods of their use in poultry vaccines.

25 Claims, 2 Drawing Sheets

Specification includes a Sequence Listing.

(56) References Cited

U.S. PATENT DOCUMENTS

| | | | |
|---|---|---|---|
| 2008/0233146 A1 | 9/2008 | Sato | |
| 2018/0163230 A1 | 6/2018 | Bublot et al. | |
| 2021/0010033 A1 | 1/2021 | Bublot et al. | |
| 2021/0386854 A1 | 12/2021 | Ameiss et al. | |

FOREIGN PATENT DOCUMENTS

| | | | |
|---|---|---|---|
| EP | 3041939 | B1 | 3/2019 |
| EP | 3708670 | A1 | 9/2020 |
| JP | 2015500631 | A | 1/2015 |
| RU | 2593950 | C2 | 8/2016 |
| RU | 2624037 | C2 | 6/2017 |
| WO | 198704463 | A1 | 7/1987 |
| WO | 198704663 | A1 | 7/1987 |
| WO | 199203554 | A1 | 3/1992 |
| WO | 1996005291 | A1 | 2/1996 |
| WO | 1998037216 | A1 | 8/1998 |
| WO | 2000061736 | A2 | 10/2000 |
| WO | 2013057235 | A1 | 4/2013 |
| WO | 2013057236 | A1 | 4/2013 |
| WO | 2013082327 | A1 | 6/2013 |
| WO | 2016102647 | A1 | 6/2016 |
| WO | 2017216287 | A1 | 12/2017 |
| WO | 2018112051 | A1 | 6/2018 |
| WO | 2020127964 | A1 | 6/2020 |
| WO | 2021257706 | A1 | 12/2021 |

OTHER PUBLICATIONS

Bobrovskaya, Irina Vladimirovna, Antigenic Properties of Infectious and Thermoinactivated Vaccine Preparations of Marek's Disease Virus Strains, Shchyolkovo, 2000, 1-31, N/A.

Afonso, et al., The Genome of Turkey Herpesvirus, Journal of Virology, 2001, 971-978, 75-2.

Dartiel, et al., Herpesvirus of Turkey Recombinant Viruses Expressing Infectious Bursal Disease Virus (IBDV) VP2 Immunogen Induce Protection Against an IBDV Virulent Challenge in Chickens, Virology, 1995, 481-490, 211.

Fuchs, et al., Molecular Biology of Avian Infectious Laryngotracheitis Virus, Veterinary Research, 2007, 261-279, 38.

Johnson, et al., Protection Against Infectious Laryngotracheitis by In Ovo Vaccination with Commercially Available Viral Vector Recombinant Vaccines, Avian Diseases, 2010, 1251-1259, 54.

Kingham, et al., The Genome of Herpesvirus of Turkeys: Comparative Analysis with Marek's Disease Viruses, Journal of General Virology, 2001, 1123-1135, 82.

Murthy, et al., Pathogenesis of Marek's Disease: Effect of Immunization with Inactivated Viral and Tumor-Associated Antigens, Infection and Immunity, 1979, pp. 547-533, 26-2.

Petherbridge, et al., Cloning of Gallid Herpesvirus 3 (Marek's Disease Virus Serotype-2), Journal of Virological Methods, 2009, 11-17, 158.

Sondermeijer, et al., Avian Herpesvirus as a Live Viral Vector for the Expression of Heterologous Antigens, Vaccine, 1993, 349-358, 11.

Tsukamoto, et al., Complete, Long-Lasting Protection Against Lethal Infectious Bursal Disease Virus Challenge by a Single Vaccination with an Avian Herepesvirus Vector Expressing VP2 Antigens, Journal of Virology, 2002, 5637-5645, 76-11.

Van Zijl, et al., Regeneration of Herpesviruses from Molecularly Cloned Subgenomic Fragments, Journal of Virology, 1988, 2191-2195, 62-6.

Wild, et al., A Genomic map of Infectious Laryngotracheitis Virus and the Sequence and Organization of Genes Present in the Unique Short and Flanking Regions, Virus Genes, 1996, 107-116, 12-2.

Wu, et al., Molecular Detection and Differentiation of Infectious Bursal Disease Virus, Avian Diseases, 2007, 515-526, 51.

Hao, X. et al., Research Progress in Herpesvirus of Turkey Vectored Avian Influenza Vaccines, China Poultry, 2015, 48-52, 37(21).

Hao, Xiaoli et al., Research Progress in Herpesvirus of Turkey Vectored Avian influenza Vaccines, China Poultry, 2015, 48-52, 37(21).

Sun, et al., Protection of Chickens from Newcastle Disease and Infectious Laryngotracheitis with A Recombinant Fowlpox Virus Co-Expressing the F, HN Genes of Newcastle Disease Virus and gB Gene of Infectious Laryngotracheitis Virus, Avian Diseases, 2008, 111-117, 52.

* cited by examiner

SEQUENCE LISTING

<160> NUMBER OF SEQ ID NOS: 19

<210> SEQ ID NO 1
<211> LENGTH: 1134
<212> TYPE: DNA
<213> ORGANISM: Infectious laryngotracheitis virus

<400> SEQUENCE: 1

```
atggaccgcc atttattttt gaggaatgct ttttggacta tcgtactgct ttcttccttc      60

gctagccaga gcaccgccgc cgtcacgtac gactacattt taggccgtcg cgcgctcgac     120

gcgctaacca taccggcggt tggcccgtat aacagatacc tcactagggt atcaagaggc     180

tgcgacgttg tcgagctcaa cccgatttct aacgtggacg acatgatatc ggcggccaaa     240

gaaaaagaga aggggggccc tttcgaggcc tccgtcgtct ggttctacgt gattaagggc     300

gacgacggcg aggacaagta ctgtccaatc tatagaaaag agtacaggga atgtggcgac     360

gtacaactgc tatctgaatg cgccgttcaa tctgcacaga tgtgggcagt ggactatgtt     420

cctagcaccc ttgtatcgcg aaatggcgcg ggactgacta tattctcccc cactgctgcg     480

ctctctggcc aatacttgct gaccctgaaa atcgggagat ttgcgcaaac agctctcgta     540

actctagaag ttaacgatcg ctgtttaaag atcgggtcgc agcttaactt tttaccgtcg     600

aaatgctgga caacagaaca gtatcagact ggatttcaag gcgaacacct ttatccgatc     660

gcagacacca atacacgaca cgcggacgac gtatatcggg gatacgaaga tattctgcag     720

cgctggaata atttgctgag gaaaaagaat cctagcgcgc cagaccctcg tccagatagc     780

gtcccgcaag aaattcccgc tgtaaccaag aaagcggaag ggcgcacccc ggacgcagaa     840

agcagcgaaa agaaggcccc tccagaagac tcggaggacg acatgcaggc agaggcttct     900

ggagaaaatc ctgccgccct ccccgaagac gacgaagtcc ccgaggacac cgagcacgat     960

gatccaaact cggatcctga ctattacaat gacatgcccg ccgtgatccc ggtggaggag    1020

actactaaaa gttctaatgc cgtctccatg cccatattcg cggcgttcgt agcctgcgcg    1080

gtcgcgctcg tggggctact ggtttggagc atcgtaaaat gcgcgcgtag ctaa          1134
```

<210> SEQ ID NO 2
<211> LENGTH: 377
<212> TYPE: PRT
<213> ORGANISM: Infectious laryngotracheitis virus

<400> SEQUENCE: 2

```
Met Asp Arg His Leu Phe Leu Arg Asn Ala Phe Trp Thr Ile Val Leu
1               5                   10                  15

Leu Ser Ser Phe Ala Ser Gln Ser Thr Ala Ala Val Thr Tyr Asp Tyr
            20                  25                  30

Ile Leu Gly Arg Arg Ala Leu Asp Ala Leu Thr Ile Pro Ala Val Gly
        35                  40                  45

Pro Tyr Asn Arg Tyr Leu Thr Arg Val Ser Arg Gly Cys Asp Val Val
    50                  55                  60

Glu Leu Asn Pro Ile Ser Asn Val Asp Asp Met Ile Ser Ala Ala Lys
65                  70                  75                  80

Glu Lys Glu Lys Gly Gly Pro Phe Glu Ala Ser Val Val Trp Phe Tyr
                85                  90                  95

Val Ile Lys Gly Asp Asp Gly Glu Asp Lys Tyr Cys Pro Ile Tyr Arg
            100                 105                 110

Lys Glu Tyr Arg Glu Cys Gly Asp Val Gln Leu Leu Ser Glu Cys Ala
        115                 120                 125
```

```
Val Gln Ser Ala Gln Met Trp Ala Val Asp Tyr Val Pro Ser Thr Leu
    130                 135                 140

Val Ser Arg Asn Gly Ala Gly Leu Thr Ile Phe Ser Pro Thr Ala Ala
145                 150                 155                 160

Leu Ser Gly Gln Tyr Leu Leu Thr Leu Lys Ile Gly Arg Phe Ala Gln
                165                 170                 175

Thr Ala Leu Val Thr Leu Glu Val Asn Asp Arg Cys Leu Lys Ile Gly
            180                 185                 190

Ser Gln Leu Asn Phe Leu Pro Ser Lys Cys Trp Thr Thr Glu Gln Tyr
        195                 200                 205

Gln Thr Gly Phe Gln Gly Glu His Leu Tyr Pro Ile Ala Asp Thr Asn
    210                 215                 220

Thr Arg His Ala Asp Asp Val Tyr Arg Gly Tyr Glu Asp Ile Leu Gln
225                 230                 235                 240

Arg Trp Asn Asn Leu Leu Arg Lys Lys Asn Pro Ser Ala Pro Asp Pro
                245                 250                 255

Arg Pro Asp Ser Val Pro Gln Glu Ile Pro Ala Val Thr Lys Lys Ala
            260                 265                 270

Glu Gly Arg Thr Pro Asp Ala Glu Ser Ser Glu Lys Lys Ala Pro Pro
        275                 280                 285

Glu Asp Ser Glu Asp Asp Met Gln Ala Glu Ala Ser Gly Glu Asn Pro
    290                 295                 300

Ala Ala Leu Pro Glu Asp Asp Glu Val Pro Glu Asp Thr Glu His Asp
305                 310                 315                 320

Asp Pro Asn Ser Asp Pro Asp Tyr Tyr Asn Asp Met Pro Ala Val Ile
                325                 330                 335

Pro Val Glu Glu Thr Thr Lys Ser Ser Asn Ala Val Ser Met Pro Ile
            340                 345                 350

Phe Ala Ala Phe Val Ala Cys Ala Val Ala Leu Val Gly Leu Leu Val
        355                 360                 365

Trp Ser Ile Val Lys Cys Ala Arg Ser
    370                 375
```

<210> SEQ ID NO 3
<211> LENGTH: 1089
<212> TYPE: DNA
<213> ORGANISM: Infectious laryngotracheitis virus

<400> SEQUENCE: 3

```
atggcatcgc tacttggaac tctggctctc cttgccgcga cgctcgcacc cttcggcgcg      60

atgggaatcg tgatcactgg aaatcacgtc tccgccagga ttgacgacga tcacatcgtg     120

atcgtcgcgc ctcgccccga agctacaatt caactgcagc tatttttcat gcctggccag     180

agaccccaca aaccctactc aggaaccgtc cgcgtcgcgt ttcggtctga tataacaaac     240

cagtgctacc aggaacttag cgaggagcgc tttgaaaatt gcactcatcg atcgtcttct     300

gtttttgtcg gctgtaaagt gaccgagtac acgttctccg cctcgaacag actaaccgga     360

cctccacacc cgtttaagct cactatacga aatcctcgtc cgaacgacag cgggatgttc     420

tacgtaattg ttcggctaga cgacaccaaa gaacccattg acgtcttcgc gatccaacta     480

tcggtgtatc aattcgcgaa caccgccgcg actcgcggac tctattccaa ggcttcgtgt     540

cgcaccttcg gattacctac cgtccaactt gaggcctatc tcaggaccga ggaaagttgg     600

cgcaactggc aagcgtacgt tgccacggag gccacgacga ccagcgccga ggcgacaacc     660
```

```
ccgacgcccg tcactgcaac cagcgcctcc gaacttgaag cggaacactt tacctttccc    720

tggctagaaa atggcgtgga tcattacgaa ccgacacccg caaacgaaaa ttcaaacgtt    780

actgtccgtc tcgggacaat gagccctacg ctaattgggg taaccgtggc tgccgtcgtg    840

agcgcaacga tcggcctcgt cattgtaatt tccatcgtca ccagaaacat gtgcaccccg    900

caccgaaaat tagacacggt ctcgcaagac gacgaagaac gttcccaaac tagaagggaa    960

tcgcgaaaat ttggacccat ggttgcgtgc gaaataaaca agggggctga ccaggatagt   1020

gaacttgtgg aactggttgc gattgttaac ccgtctgcgc taagctcgcc cgactcaata   1080

aaaatgtga                                                           1089


<210> SEQ ID NO 4
<211> LENGTH: 362
<212> TYPE: PRT
<213> ORGANISM: Infectious laryngotracheitis virus

<400> SEQUENCE: 4

Met Ala Ser Leu Leu Gly Thr Leu Ala Leu Leu Ala Ala Thr Leu Ala
1               5                   10                  15

Pro Phe Gly Ala Met Gly Ile Val Ile Thr Gly Asn His Val Ser Ala
            20                  25                  30

Arg Ile Asp Asp Asp His Ile Val Ile Val Ala Pro Arg Pro Glu Ala
        35                  40                  45

Thr Ile Gln Leu Gln Leu Phe Phe Met Pro Gly Gln Arg Pro His Lys
    50                  55                  60

Pro Tyr Ser Gly Thr Val Arg Val Ala Phe Arg Ser Asp Ile Thr Asn
65                  70                  75                  80

Gln Cys Tyr Gln Glu Leu Ser Glu Glu Arg Phe Glu Asn Cys Thr His
                85                  90                  95

Arg Ser Ser Ser Val Phe Val Gly Cys Lys Val Thr Glu Tyr Thr Phe
            100                 105                 110

Ser Ala Ser Asn Arg Leu Thr Gly Pro Pro His Pro Phe Lys Leu Thr
        115                 120                 125

Ile Arg Asn Pro Arg Pro Asn Asp Ser Gly Met Phe Tyr Val Ile Val
    130                 135                 140

Arg Leu Asp Asp Thr Lys Glu Pro Ile Asp Val Phe Ala Ile Gln Leu
145                 150                 155                 160

Ser Val Tyr Gln Phe Ala Asn Thr Ala Ala Thr Arg Gly Leu Tyr Ser
                165                 170                 175

Lys Ala Ser Cys Arg Thr Phe Gly Leu Pro Thr Val Gln Leu Glu Ala
            180                 185                 190

Tyr Leu Arg Thr Glu Glu Ser Trp Arg Asn Trp Gln Ala Tyr Val Ala
        195                 200                 205

Thr Glu Ala Thr Thr Thr Ser Ala Glu Ala Thr Thr Pro Thr Pro Val
    210                 215                 220

Thr Ala Thr Ser Ala Ser Glu Leu Glu Ala Glu His Phe Thr Phe Pro
225                 230                 235                 240

Trp Leu Glu Asn Gly Val Asp His Tyr Glu Pro Thr Pro Ala Asn Glu
                245                 250                 255

Asn Ser Asn Val Thr Val Arg Leu Gly Thr Met Ser Pro Thr Leu Ile
            260                 265                 270

Gly Val Thr Val Ala Ala Val Val Ser Ala Thr Ile Gly Leu Val Ile
        275                 280                 285

Val Ile Ser Ile Val Thr Arg Asn Met Cys Thr Pro His Arg Lys Leu
```

-continued

```
    290                 295                 300

Asp Thr Val Ser Gln Asp Asp Glu Glu Arg Ser Gln Thr Arg Arg Glu
305                 310                 315                 320

Ser Arg Lys Phe Gly Pro Met Val Ala Cys Glu Ile Asn Lys Gly Ala
                325                 330                 335

Asp Gln Asp Ser Glu Leu Val Glu Leu Val Ala Ile Val Asn Pro Ser
            340                 345                 350

Ala Leu Ser Ser Pro Asp Ser Ile Lys Met
        355                 360


<210> SEQ ID NO 5
<211> LENGTH: 1362
<212> TYPE: DNA
<213> ORGANISM: Infectious bursal disease virus

<400> SEQUENCE: 5

atgacaaacc tgcaagatca aacccaacag attgttccgt tcatacggag ccttctgatg      60

ccaacaaccg gaccggcgtc cattccggac gacaccctgg agaagcacac tctcaggtca     120

gagacctcga cctacaattt gactgtgggg gacacagggt cagggctaat tgtcttttc     180

cctggattcc ctggctcaat tgtgggtgct cactacacac tgcagagcaa tgggaactac     240

aagttcgatc agatgctcct gactgcccag aacctaccgg ccagctacaa ctactgcaga     300

ctagtgagtc ggagtctcac agtgaggtca agcacactcc ctggtggcgt ttatgcacta     360

aacggcacca taaacgccgt gaccttccaa ggaagcctga gtgaactgac agatgttagc     420

tacaatgggt tgatgtctgc aacagccaac atcaacgaca aaattgggaa tgtcctggta     480

ggggaagggg tcactgtcct cagcctaccc acatcatatg atcttgggta tgtgaggctt     540

ggtgacccca ttcccgctat agggcttgac ccaaaaatgg tagctacatg cgacagcagt     600

gacaggccca gagtctacac cataactgca gccgatgatt accaattctc atcacagtac     660

caaccaggtg ggtaacaat cacactgttc tcagccaaca ttgatgctat cacaagcctc     720

agcattgggg gagagctcgt gtttcaaaca agcgtccaag gccttgtact gggcgccacc     780

atctacctta taggctttga tgggactgcg gtaatcacca gagctgtggc cgcagataat     840

gggctgacgg ccggcaccga caatcttatg ccattcaatc ttgtcattcc aaccaatgag     900

ataacccagc caatcacatc catcaaactg gagatagtga cctccaaaag tggtggtcag     960

gcaggggatc agatgtcatg gtcggcaagt gggagcctag cagtgacgat ccatggtggc    1020

aactatccag ggccctccg tcccgtcaca ctagtagcct acgaaagagt ggcaacagga    1080

tccgtcgtta cggtcgctgg ggtgagtaac ttcgagctga ttccaaatcc tgaactagca    1140

aagaacctgg ttacagaata cggccgattt gacccaggag ccatgaacta cacaaaattg    1200

atactgagtg agagggaccg tcttggcatc aagaccgtct ggccaacaag ggagtacact    1260

gattttcgtg agtacttcat ggaggtggcc gacctcaact ctcccctgaa gattgcagga    1320

gcatttggct tcaaagacat aatccgggct ataaggaggt aa                        1362


<210> SEQ ID NO 6
<211> LENGTH: 453
<212> TYPE: PRT
<213> ORGANISM: Infectious bursal disease virus

<400> SEQUENCE: 6

Met Thr Asn Leu Gln Asp Gln Thr Gln Gln Ile Val Pro Phe Ile Arg
1               5                   10                  15
```

-continued

```
Ser Leu Leu Met Pro Thr Thr Gly Pro Ala Ser Ile Pro Asp Asp Thr
            20                  25                  30

Leu Glu Lys His Thr Leu Arg Ser Glu Thr Ser Thr Tyr Asn Leu Thr
        35                  40                  45

Val Gly Asp Thr Gly Ser Gly Leu Ile Val Phe Phe Pro Gly Phe Pro
    50                  55                  60

Gly Ser Ile Val Gly Ala His Tyr Thr Leu Gln Ser Asn Gly Asn Tyr
65                  70                  75                  80

Lys Phe Asp Gln Met Leu Leu Thr Ala Gln Asn Leu Pro Ala Ser Tyr
                85                  90                  95

Asn Tyr Cys Arg Leu Val Ser Arg Ser Leu Thr Val Arg Ser Ser Thr
            100                 105                 110

Leu Pro Gly Gly Val Tyr Ala Leu Asn Gly Thr Ile Asn Ala Val Thr
        115                 120                 125

Phe Gln Gly Ser Leu Ser Glu Leu Thr Asp Val Ser Tyr Asn Gly Leu
    130                 135                 140

Met Ser Ala Thr Ala Asn Ile Asn Asp Lys Ile Gly Asn Val Leu Val
145                 150                 155                 160

Gly Glu Gly Val Thr Val Leu Ser Leu Pro Thr Ser Tyr Asp Leu Gly
                165                 170                 175

Tyr Val Arg Leu Gly Asp Pro Ile Pro Ala Ile Gly Leu Asp Pro Lys
            180                 185                 190

Met Val Ala Thr Cys Asp Ser Ser Asp Arg Pro Arg Val Tyr Thr Ile
        195                 200                 205

Thr Ala Ala Asp Asp Tyr Gln Phe Ser Ser Gln Tyr Gln Pro Gly Gly
    210                 215                 220

Val Thr Ile Thr Leu Phe Ser Ala Asn Ile Asp Ala Ile Thr Ser Leu
225                 230                 235                 240

Ser Ile Gly Gly Glu Leu Val Phe Gln Thr Ser Val Gln Gly Leu Val
                245                 250                 255

Leu Gly Ala Thr Ile Tyr Leu Ile Gly Phe Asp Gly Thr Ala Val Ile
            260                 265                 270

Thr Arg Ala Val Ala Ala Asp Asn Gly Leu Thr Ala Gly Thr Asp Asn
        275                 280                 285

Leu Met Pro Phe Asn Leu Val Ile Pro Thr Asn Glu Ile Thr Gln Pro
    290                 295                 300

Ile Thr Ser Ile Lys Leu Glu Ile Val Thr Ser Lys Ser Gly Gly Gln
305                 310                 315                 320

Ala Gly Asp Gln Met Ser Trp Ser Ala Ser Gly Ser Leu Ala Val Thr
                325                 330                 335

Ile His Gly Gly Asn Tyr Pro Gly Ala Leu Arg Pro Val Thr Leu Val
            340                 345                 350

Ala Tyr Glu Arg Val Ala Thr Gly Ser Val Val Thr Val Ala Gly Val
        355                 360                 365

Ser Asn Phe Glu Leu Ile Pro Asn Pro Glu Leu Ala Lys Asn Leu Val
    370                 375                 380

Thr Glu Tyr Gly Arg Phe Asp Pro Gly Ala Met Asn Tyr Thr Lys Leu
385                 390                 395                 400

Ile Leu Ser Glu Arg Asp Arg Leu Gly Ile Lys Thr Val Trp Pro Thr
                405                 410                 415

Arg Glu Tyr Thr Asp Phe Arg Glu Tyr Phe Met Glu Val Ala Asp Leu
            420                 425                 430

Asn Ser Pro Leu Lys Ile Ala Gly Ala Phe Gly Phe Lys Asp Ile Ile
```

-continued 435 440 445

Arg Ala Ile Arg Arg
450

<210> SEQ ID NO 7
<211> LENGTH: 527
<212> TYPE: DNA
<213> ORGANISM: Infectious laryngotracheitis virus

<400> SEQUENCE: 7
aaacagctgt actacagagt aaccgatgga agaacatcgg tccagctaat gtgcctgtcg 60
tgcacgagcc attctccgga accttactgt cttttcgaca cgtctcttat agcgagggaa 120
aaagatatcg cgccagagtt atactttacc tctgatccgc aaacggcata ctgcacaata 180
actctgccgt ccggcgttgt tccgagattc gaatggagcc ttaataatgt ttcactgccg 240
gaatatttga cggccacgac cgttgtttcg cataccgctg gccaaagtac agtgtggaag 300
agcagcgcga gagcaggcga ggcgtggatt tctggccggg gaggcaatat atacgaatgc 360
accgtcctca tctcagacgg cactcgcgtt actacgcgaa aggagaggtg cttaacaaac 420
acatggattg cggtggaaaa cggtgctgct caggcgcagc tgtattcact cttttctgga 480
cttgtgtcag gattatgcgg gagcatatct gctttgtacg caacgct 527

<210> SEQ ID NO 8
<211> LENGTH: 264
<212> TYPE: DNA
<213> ORGANISM: Infectious laryngotracheitis virus

<400> SEQUENCE: 8
tgactattac aatgacatgc ccgccgtgat cccggtggag gagactacta aaagttctaa 60
tgccgtctcc atgcccatat tcgcggcgtt cgtagcctgc gcggtcgcgc tcgtggggct 120
actggtttgg agcatcgtaa aatgcgcgcg tagctaatcg agcctagaat aggtggtttc 180
ttcctacatg ccacgcctca cgctcataat ataaatcaca tggaatagca taccaatgcc 240
tattcattgg gacgttcgaa aagc 264

<210> SEQ ID NO 9
<211> LENGTH: 3563
<212> TYPE: DNA
<213> ORGANISM: Infectious laryngotracheitis virus

<400> SEQUENCE: 9
tcgacggcag agtcgcagac gcccctattg gacgtcaaaa ttgtagaggt gaagttttca 60
aacgatggcg aagtaacggc gacttgcgtt tccaccgtca aatctcccta tagggtagaa 120
actaattgga aagtagacct cgtagatgta atggatgaaa tttctgggaa cagtcccgcc 180
ggggttttta acagtaatga gaaatggcag aaacagctgt actacagagt aaccgatgga 240
agaacatcgg tccagctaat gtgcctgtcg tgcacgagcc attctccgga accttactgt 300
cttttcgaca cgtctcttat agcgagggaa aaagatatcg cgccagagtt atactttacc 360
tctgatccgc aaacggcata ctgcacaata actctgccgt ccggcgttgt tccgagattc 420
gaatggagcc ttaataatgt ttcactgccg gaatatttga cggccacgac cgttgtttcg 480
cataccgctg gccaaagtac agtgtggaag agcagcgcga gagcaggcga ggcgtggatt 540
tctggccggg gaggcaatat atacgaatgc accgtcctca tctcagacgg cactcgcgtt 600
actacgcgaa aggagaggtg cttaacaaac acatggattg cggtggaaaa cggtgctgct 660

-continued

```
caggcgcagc tgtattcact cttttctgga cttgtgtcag gattatgcgg gagcatatct    720
gctttgtacg caacgctatg gaccgccatt tatttttgag gaatgctttt tggactatcg    780
tactgctttc ttccttcgct agccagagca ccgccgccgt cacgtacgac tacattttag    840
gccgtcgcgc gctcgacgcg ctaaccatac cggcggttgg cccgtataac agatacctca    900
ctagggtatc aagaggctgc gacgttgtcg agctcaaccc gatttctaac gtggacgaca    960
tgatatcggc ggccaaagaa aaagagaagg ggggcccttt cgaggcctcc gtcgtctggt   1020
tctacgtgat taagggcgac gacggcgagg acaagtactg tccaatctat agaaaaagagt   1080
acagggaatg tggcgacgta caactgctat ctgaatgcgc cgttcaatct gcacagatgt   1140
gggcagtgga ctatgttcct agcacccttg tatcgcgaaa tggcgcggga ctgactatat   1200
tctcccccac tgctgcgctc tctggccaat acttgctgac cctgaaaatc gggagatttg   1260
cgcaaacagc tctcgtaact ctagaagtta acgatcgctg tttaaagatc gggtcgcagc   1320
ttaacttttt accgtcgaaa tgctggacaa cagaacagta tcagactgga tttcaaggcg   1380
aacacccttta tccgatcgca gacaccaata cacgacacgc ggacgacgta tatcggggat   1440
acgaagatat tctgcagcgc tggaataatt tgctgaggaa aaagaatcct agcgcgccag   1500
accctcgtcc agatagcgtc ccgcaagaaa ttcccgctgt aaccaagaaa gcggaagggc   1560
gcaccccgga cgcagaaagc agcgaaaaga aggcccctcc agaagactcg gaggacgaca   1620
tgcaggcaga ggcttctgga gaaaatcctg ccgccctccc cgaagacgac gaagtccccg   1680
aggacaccga gcacgatgat ccaaactcgg atcctgacta ttacaatgac atgcccgccg   1740
tgatcccggt ggaggagact actaaaagtt ctaatgccgt ctccatgccc atattcgcgg   1800
cgttcgtagc ctgcgcggtc gcgctcgtgg ggctactggt ttggagcatc gtaaaatgcg   1860
cgcgtagcta atcgagccta gaataggtgg tttcttccta catgccacgc ctcacgctca   1920
taatataaat cacatggaat agcataccaa tgcctattca ttgggacgtt cgaaaagcat   1980
ggcatcgcta cttggaactc tggctctcct tgccgcgacg ctcgcaccct tcggcgcgat   2040
gggaatcgtg atcactggaa atcacgtctc cgccaggatt gacgacgatc acatcgtgat   2100
cgtcgcgcct cgccccgaag ctacaattca actgcagcta tttttcatgc ctggccagag   2160
accccacaaa ccctactcag gaaccgtccg cgtcgcgttt cggtctgata taacaaacca   2220
gtgctaccag gaacttagcg aggagcgctt tgaaaattgc actcatcgat cgtcttctgt   2280
ttttgtcggc tgtaaagtga ccgagtacac gttctccgcc tcgaacagac taaccggacc   2340
tccacacccg tttaagctca ctatacgaaa tcctcgtccg aacgacagcg ggatgttcta   2400
cgtaattgtt cggctagacg acaccaaaga acccattgac gtcttcgcga tccaactatc   2460
ggtgtatcaa ttcgcgaaca ccgccgcgac tcgcggactc tattccaagg cttcgtgtcg   2520
caccttcgga ttacctaccg tccaacttga ggcctatctc aggaccgagg aaagttggcg   2580
caactggcaa gcgtacgttg ccacggaggc cacgacgacc agcgccgagg cgacaacccc   2640
gacgcccgtc actgcaacca gcgcctccga acttgaagcg gaacacttta cctttccctg   2700
gctagaaaat ggcgtggatc attacgaacc gacacccgca aacgaaaatt caaacgttac   2760
tgtccgtctc gggacaatga gccctacgct aattggggta accgtggctg ccgtcgtgag   2820
cgcaacgatc ggcctcgtca ttgtaatttc catcgtcacc agaaacatgt gcaccccgca   2880
ccgaaaatta gacacggtct cgcaagacga cgaagaacgt tcccaaacta gaagggaatc   2940
gcgaaaattt ggacccatgg ttgcgtgcga aataaacaag gggctgacc aggatagtga    3000
acttgtggaa ctggttgcga ttgttaaccc gtctgcgcta agctcgcccg actcaataaa   3060
```

```
aatgtgatta agtctgaatg tggctctcca atcatttcga ttctctaatc tcccaatcct   3120

ctcaaaaggg gcagtatcgg acacggactg ggaggggcgt acacgatagt tatatggtac   3180

agcagaggcc tctgaacact taggaggaga attcagccgg ggagagcccc tgttgagtag   3240

gcttgggagc atattgcagg atgaacatgt tagtgatagt tctcgcctct tgtcttgcgc   3300

gcctaacttt tgcgacgcga cacgtcctct tttggaagg cactcaggct gtcctcgggg   3360

aagatgatcc cagaaacgtt ccggaaggga ctgtaatcaa atggacaaaa gtcctgcgga   3420

acgcgtgcaa gatgaaggcg gccgatgtct gctcttcgcc taactattgc tttcatgatt   3480

taatttacga cggaggaaag aaagactgcc cgcccgcggg acccctgtct gcaaacctgg   3540

taattttact aaagcgcggc gaa                                            3563
```

<210> SEQ ID NO 10
<211> LENGTH: 1391
<212> TYPE: DNA
<213> ORGANISM: Murine cytomegalovirus

<400> SEQUENCE: 10

```
aactccgccc gttttatgac tagaaccaat agtttttaat gccaaatgca ctgaaatccc     60

ctaatttgca aagccaaacg ccccctatgt gagtaatacg ggactttttt acccaatttc    120

ccacgcggaa agccccctaa tacactcata tggcatatga atcagcacgg tcatgcactc    180

taatggcggc ccatagggac tttccacata gggggcgttc accatttccc agcatagggg    240

tggtgactca atggccttta cccaagtaca ttgggtcaat gggaggtaag ccaatgggtt    300

tttcccatta ctggcaagca cactgagtca aatgggactt tccactgggt tttgcccaag    360

tacattgggt caatgggagg tgagccaatg ggaaaaaccc attgctgcca agtacactga    420

ctcaataggg actttccaat gggtttttcc attgttggca agcatataag gtcaatgtgg    480

gtgagtcaat agggactttc cattgtattc tgcccagtac ataaggtcaa tagggggtga    540

atcaacagga aagtcccatt ggagccaagt acactgcgtc aatagggact ttccattggg    600

ttttgcccag tacataaggt caatagggga tgagtcaatg ggaaaaaccc attggagcca    660

agtacactga ctcaataggg actttccatt gggttttgcc cagtacataa ggtcaatagg    720

gggtgagtca acaggaaagt tccattggag ccaagtacat tgagtcaata gggactttcc    780

aatgggtttt gcccagtaca taaggtcaat gggaggtaag ccaatgggtt tttcccatta    840

ctggcacgta tactgagtca ttagggactt tccaatgggt tttgcccagt acataaggtc    900

aataggggtg aatcaacagg aaagtcccat tggagccaag tacactgagt caatagggac    960

tttccattgg gttttgccca gtacaaaagg tcaatagggg gtgagtcaat gggtttttcc   1020

cattattggc acgtacataa ggtcaatagg ggtgagtcat tgggtttttc cagccaattt   1080

aattaaaacg ccatgtactt tcccaccatt gacgtcaatg ggctattgaa actaatgcaa   1140

cgtgaccttt aaacggtact ttcccatagc tgattaatgg gaaagtaccg ttctcgagcc   1200

aatacacgtc aatgggaagt gaaagggcag ccaaaacgta acaccgcccc ggtttccccc   1260

tggaaattcc atattggcac gcattctatt ggctgagctg cgttctacgt gggtataaga   1320

ggcgcgacca gcgtcggtac cgtcgcagtc ttcggtctga ccaccgtaga acgcagagct   1380

cctcgctgca g                                                        1391
```

<210> SEQ ID NO 11
<211> LENGTH: 692
<212> TYPE: DNA

<213> ORGANISM: Gallus gallus
<220> FEATURE:
<221> NAME/KEY: misc_feature
<222> LOCATION: (141)..(143)
<223> OTHER INFORMATION: n is a, c, g, or t

<400> SEQUENCE: 11
cgcgccggat cagatctcca tggtcgaggt gagccccacg ttctgcttca ctctccccat 60
ctcccccccc tccccacccc caattttgta tttatttatt ttttaattat tttgtgcagc 120
gatgggggcg gggggggggg nnncgcgcgc caggcggggc ggggcggggc gaggggcggg 180
gcggggcgag gcggagaggt gcggcggcag ccaatcagag cggcgcgctc cgaaagtttc 240
cttttatggc gaggcggcgg cggcggcggc cctataaaaa gcgaagcgcg cggcgggcgg 300
gagtcgctgc gcgctgcctt cgccccgtgc cccgctccgc cgccgcctcg cgccgcccgc 360
cccggctctg actgaccgcg ttactcccac aggtgagcgg gcgggacggc ccttctcctc 420
cgggctgtaa ttagcggcag gaaggaaatg ggcggggagg gccttcgtgc gtcgccgcgc 480
cgccgtcccc ttctccctct ccagcctcgg ggctgtccgc ggggggacgg ctgccttcgg 540
gggggacggg gcagggcggg gttcggcttc tggcgtgtga ccggcggctc tagagcctct 600
gctaaccatg ttcatgcctt cttctttttc ctacagctcc tgggcaacgt gctggttatt 660
gtgctgtctc atcattttgg caaagaattg ca 692

<210> SEQ ID NO 12
<211> LENGTH: 301
<212> TYPE: DNA
<213> ORGANISM: Human cytomegalovirus

<400> SEQUENCE: 12
ggcagtacat ctacgtatta gtcatcgcta ttaccatggt gatgcggttt tggcagtaca 60
tcaatgggcg tggatagcgg tttgactcac ggggatttcc aagtctccac cccattgacg 120
tcaatgggag tttgttttgg caccaaaatc aacgggactt tccaaaatgt cgtaacaact 180
ccgccccatt gacgcaaatg ggcggtaggc gtgtacggtg ggaggtctat ataagcagag 240
ctcgtttagt gaaccgtcag atcgcctgga gacgccatcc acgctgtttt gacctccata 300
g 301

<210> SEQ ID NO 13
<211> LENGTH: 55
<212> TYPE: DNA
<213> ORGANISM: Feline herpesvirus

<400> SEQUENCE: 13
caataaacat agcatacgtt atgacatggt ctaccgcgtc ttatatgggg acgac 55

<210> SEQ ID NO 14
<211> LENGTH: 370
<212> TYPE: DNA
<213> ORGANISM: Herpes simplex virus

<400> SEQUENCE: 14
gatccataat tgattgacgg gagatggggg aggctaactg aaacacggaa ggagacaata 60
ccggaaggaa cccgcgctat gacggcaata aaaagacaga ataaaacgca cgggtgttgg 120
gtcgtttgtt cataaacgcg gggttcggtc ccagggctgg cactctgtcg ataccccacc 180
gagaccccat tggggccaat acgcccgcgt ttcttccttt tccccacccc accccccaag 240
ttcgggtgaa ggcccagggc tcgcagccaa cgtcggggcg gcaggccctg ccatagccac 300
tggccccgtg ggttagggac ggggtccccc atggggaatg gtttatggtt cgtgggggtt 360
attattttga 370

<210> SEQ ID NO 15
<211> LENGTH: 14113
<212> TYPE: DNA
<213> ORGANISM: Artificial Sequence
<220> FEATURE:
<223> OTHER INFORMATION: Herpesvirus of turkeys, Murine cytomegalovirus, Infectious bursal disease virus, Simian vacuolating virus 40, and Infectious laryngotracheitis virus

<400> SEQUENCE: 15
gaattccaga ctaaatgccc cggcccaatt tgtcaagtgt gcagtcacgg aggcgtcgac 60
cgtgtccccg gcattaaaca ggaaagcgtt aaagtttttg aatgttaggt cacaggtaca 120
aacataaatg tttgtacaaa caggtaacag gtacaaacat aaatgccccg gcataaatgt 180
cccttacggc ggatcgaaac gacattaggc atactcgggt accattttgc attccgatca 240
gcacggatga aattaggcag gaatgcggtt tatattatgc ggcattggac aaacgatatg 300
gcattgattg gcagtttatg aatgtcttca tgttgggcgt aaacggattc ctattggttc 360
agaagacaac gacgatatat ttagagagaa aaagctaccc agcataggat aaacacacat 420
tgagcattga gagacatagg tatcggtatg gatgggaaaa ctacacacgt gaacaccaaa 480
cgacttatat actcgagcgg tgatactact gagcaagaat gcactgcatc tgagccactg 540
aatgaagact gtgatgaaaa tgtgaccatc gatggaattg gagaagaata tgcgcagttc 600
ttcatgtccc cgcaatgggt cccaaatcta catcgcttga gcgaggatac caaaaaggta 660
taccgatgta tggtttccaa cagactcaat tattttccct attatgaggc gttcaggcgg 720
tctttgtttg atatgtatat gctaggtcgg ttggggcgtc gacttaagcg atctgactgg 780
gagactatta tgcatctgtc accaacgcaa agtcggcgtc tacatagaac tttaagattt 840
gtggagcgta gaattatccc atctaacagt tatatacgca catcgggcca cgttccgcct 900
tcgagggcac ttccgacaga tacgaattta aagatggatg aataattaaa ttggaaagag 960
taactacatt aatcgagcgt catgacggcg tcccgtgaaa atgggaattt tctactcgaa 1020
acaccgtgac atttgacaga cctggaattg ttattctgat atatagtggg tgtgtctggc 1080
cggcaacata cataatgtgc atgcgaaacc actttttcag tgtacgctga cattgtgcaa 1140
cacggagggg tagcatctac atacaatata tgttgattaa tgattggaga aaaaactatg 1200
cagctcgccg atcatatggc taactcgcct tcgtctatat ggcggacccc gcgggaaaaa 1260
tcgacgtacc atctgattta caacaccagt aatgaacatg tcgcatccct gcccagatct 1320
gtgcgcccat tggcgcggat cgttgtgaat gccgccgaaa cacttcaggt cggtatgaga 1380
gccgggaggc cgccatcagc aggagtttgg cgagaggtgt ttgatagaat gatgacagcc 1440
ttccgtgacc acgagcctac tgcgacattt aatgctgcaa atcccattag aaaaatggtc 1500
gagacagttc tacagaataa tgaagagccc ccgcggacgc atgctgaaat gggtaatcgc 1560
cttatgaaca ttatgtactg gtgttgcttg ggacacgcag gacaatgctc gatatggcag 1620
ttgtacgaga cgaatcaggc cattttaagt ttattagatg aagtggttat cggcacaaca 1680
aatccctttt gcaccctcga gcaatactgg aagccattat gcaccgcaat cgccaacaag 1740
gggacctcat cgcttgttga ggatgccaaa gtggccgagt acctggttag catgcgcaaa 1800
ttgatataac ataggcacgc tctgatgtta cagaccacaa taccgcatac atttattgta 1860

-continued

```
aggttgttaa taaaggttta ttctatgtaa gactacaata ctttcgacat tgcttgtata   1920
catattaaat actttctcaa gttcctatta cataaaatgg gatctatcat tacattcgtt   1980
aagagtctgg ataattttac tgtttgccag cttcgatctt ggaacgtact gtggatagtg   2040
ccttacttgg aatcgtgaaa atttgaaacg tccattattt ggatatcttc cggttgtccc   2100
atatcccgcc ctggtaccgc tcggatacct tgcccgtatg gattcgtatt gacagtcgcg   2160
caatcgggga ccaacaacgc gtgggtccac actcattcgg aaattttccg atgattctga   2220
atatttattg ccgctcgtta cgagtcgttg gacatatctg taatacattt cttcttctga   2280
aggatcgctg cacatttgat ctatacattg gccaggatgt tcaagtctca gatgttgcat   2340
tctggcacag cacaacttta tggcatttcc gatgtaatcg tccggcagcc ctgggggagt   2400
tctatattcg catattggga tggtaaggac aatagcagat ctcgcaacct ccagggaggc   2460
tataataacg tttttaaagg atggatttct cataaaaatc tgtcgcaaat tacactgaga   2520
atatccttta ctagcgccga ttgagagcat cgtcgtccaa ttttctaaat ggaaagaaaa   2580
caaggcgggc aagagtgttc caaacatttt cattttcggc gaatctctca aatcccatgg   2640
cgtgcaattg attgcaaaat tggcacttcc gttcacgttt gtatctccaa actctaagac   2700
acttttaatt gaaaaactac gttctagtgt ggaaagaaac ctataggcag accatagaac   2760
tatttgacac cacatatctt tttgtatgtc aaactgacca tgatcgtatg ttgctgaatg   2820
cactagggca attcgctcgc gcgactccat acattgaata attccacacg tcagctcatc   2880
ggttagcaag gtccagtagt tgaagtcatt tatttttccc cgcggctggc caaatctacc   2940
tctgggaata tccaagttgt cgaatatgat cgcaccggct ctggtcatgg tgaaggaact   3000
gtagcataaa gacgcaggta tcataggggt aatatttttt tattcactca catactaaaa   3060
gtaacgcata ttagcaccat gtatgggcta tcaattgaca tttgcgtagc actacatcac   3120
gattatgtac aacataatgg gacaacatat ggcaagtaga tgcaatttcc tcacactagt   3180
tgggtttatc tactattgaa ttttccccta tctgtgatac acttgggagc ctctacaagc   3240
atattgccat catgtacgtt tttatctact gtcttaacgc ccatgggaac ggaggcgtcg   3300
tcgtcatgta ttggacggca acataggcag caacacaaat tgcgtttagg tggggtgcat   3360
gtggactcga taccaagccc ctgcagctgg ggaacgtctg gtggagagcc gataatttga   3420
tatacgcacg ccatattact gtcgttgaag tacgccttat cttctatgtt ttcaaattta   3480
ggttcccaag tggacgtgag aagtgtttgt atctcacatg gaatggccca aggcattcca   3540
gcccaggtgc ctggtacttt aatggcaaac aaacgttttg gtagaggtat tgattctatt   3600
gcagttctgc agatatctgc agccccgagt atccacaggc tatacgatac gttatcggag   3660
gcaagctgcg gccgctctag aactagtgga tcccccgggc tgcagcccaa tgtggaattc   3720
gcccttgcac attgttactc ctgcatctta aaaatatatc ctgtagtaat tttcacagca   3780
atgtcataac atcatctcgc taaagaatga cctgggattg gagaagtaat gaatatttgc   3840
aaccaatgca ttgaataaac taacattaaa cgaattcact agtggatccc ccaactccgc   3900
ccgttttatg actagaacca atagttttta atgccaaatg cactgaaatc ccctaatttg   3960
caaagccaaa cgccccctat gtgagtaata cggggacttt ttacccaatt tcccacgcgg   4020
aaagccccct aatacactca tatggcatat gaatcagcac ggtcatgcac tctaatggcg   4080
gcccataggg actttccaca tagggggcgt tcaccatttc ccagcatagg ggtggtgact   4140
caatggcctt tacccaagta cattgggtca atgggaggta agccaatggg tttttcccat   4200
tactggcaag cacactgagt caaatgggac tttccactgg gttttgccca agtacattgg   4260
```

-continued

```
gtcaatggga ggtgagccaa tgggaaaaac ccattgctgc caagtacact gactcaatag   4320
ggactttcca atgggttttt ccattgttgg caagcatata aggtcaatgt gggtgagtca   4380
atagggactt tccattgtat tctgcccagt acataaggtc aataggggt gaatcaacag    4440
gaaagtccca ttggagccaa gtacactgcg tcaatagggga ctttccattg ggttttgccc  4500
agtacataag gtcaataggg gatgagtcaa tgggaaaaac ccattggagc caagtacact   4560
gactcaatag ggactttcca ttgggttttg cccagtacat aaggtcaata gggggtgagt   4620
caacaggaaa gttccattgg agccaagtac attgagtcaa tagggacttt ccaatgggtt   4680
ttgcccagta cataaggtca atgggaggta agccaatggg tttttcccat tactggcacg   4740
tatactgagt cattagggac tttccaatgg gttttgccca gtacataagg tcaatagggg   4800
tgaatcaaca ggaaagtccc attggagcca agtacactga gtcaataggg actttccatt   4860
gggttttgcc cagtacaaaa ggtcaatagg gggtgagtca atgggttttt cccattattg   4920
gcacgtacat aaggtcaata ggggtgagtc attgggtttt tccagccaat ttaattaaaa   4980
cgccatgtac tttcccacca ttgacgtcaa tgggctattg aaactaatgc aacgtgacct   5040
ttaaacggta ctttcccata gctgattaat gggaaagtac cgttctcgag ccaatacacg   5100
tcaatgggaa gtgaaagggc agccaaaacg taacaccgcc ccggttttcc cctggaaatt   5160
ccatattggc acgcattcta ttggctgagc tgcgttctac gtgggtataa gaggcgcgac   5220
cagcgtcggt accgtcgcag tcttcggtct gaccaccgta gaacgcagag ctcctcgctg   5280
caggcggccg ctctagaact cgtcgatcgc agcgatgaca aacctgcaag atcaaaccca   5340
acagattgtt ccgttcatac ggagccttct gatgccaaca accggaccgg cgtccattcc   5400
ggacgacacc ctggagaagc acactctcag gtcagagacc tcgacctaca atttgactgt   5460
gggggacaca gggtcagggc taattgtctt tttccctgga ttccctggct caattgtggg   5520
tgctcactac acactgcaga gcaatgggaa ctacaagttc gatcagatgc tcctgactgc   5580
ccagaaccta ccggccagct acaactactg cagactagtg agtcggagtc tcacagtgag   5640
gtcaagcaca ctccctggtg gcgtttatgc actaaacggc accataaacg ccgtgacctt   5700
ccaaggaagc ctgagtgaac tgacagatgt tagctacaat gggttgatgt ctgcaacagc   5760
caacatcaac gacaaaattg ggaatgtcct ggtaggggaa ggggtcactg tcctcagcct   5820
acccacatca tatgatcttg ggtatgtgag gcttggtgac cccattcccg ctatagggct   5880
tgacccaaaa atggtagcta catgcgacag cagtgacagg cccagagtct acaccataac   5940
tgcagccgat gattaccaat tctcatcaca gtaccaacca ggtggggtaa caatcacact   6000
gttctcagcc aacattgatg ctatcacaag cctcagcatt gggggagagc tcgtgtttca   6060
aacaagcgtc caaggccttg tactgggcgc caccatctac cttataggct ttgatgggac   6120
tgcggtaatc accagagctg tggccgcaga taatgggctg acggccggca ccgacaatct   6180
tatgccattc aatcttgtca ttccaaccaa tgagataacc cagccaatca catccatcaa   6240
actggagata gtgacctcca aaagtggtgg tcaggcaggg gatcagatgt catggtcggc   6300
aagtgggagc ctagcagtga cgatccatgg tggcaactat ccaggggccc tccgtcccgt   6360
cacactagta gcctacgaaa gagtggcaac aggatccgtc gttacggtcg ctggggtgag   6420
taacttcgag ctgattccaa atcctgaact agcaaagaac ctggttacag aatacggccg   6480
atttgaccca ggagccatga actacacaaa attgatactg agtgagaggg accgtcttgg   6540
catcaagacc gtctggccaa caagggagta cactgatttt cgtgagtact tcatggaggt   6600
```

-continued

```
ggccgacctc aactctcccc tgaagattgc aggagcattt ggcttcaaag acataatccg   6660
ggctataagg aggtaagctt cagacatgat aagatacatt gatgagtttg gacaaaccac   6720
aactagaatg cagtgaaaaa aatgctttat ttgtgaaatt tgtgatgcta ttgctttatt   6780
tgtaaccatt ataagctgca ataaacaagt taacaacaac aattgcattc attttatgtt   6840
tcaggttcag ggggaggtgt gggaggtttt ttcggatcct ctagagtcga cggcagagtc   6900
gcagacgccc ctattggacg tcaaaattgt agaggtgaag ttttcaaacg atggcgaagt   6960
aacggcgact tgcgtttcca ccgtcaaatc tccctatagg gtagaaacta attggaaagt   7020
agacctcgta gatgtaatgg atgaaatttc tgggaacagt cccgccgggg tttttaacag   7080
taatgagaaa tggcagaaac agctgtacta cagagtaacc gatggaagaa catcggtcca   7140
gctaatgtgc ctgtcgtgca cgagccattc tccggaacct tactgtcttt tcgacacgtc   7200
tcttatagcg agggaaaaag atatcgcgcc agagttatac tttacctctg atccgcaaac   7260
ggcatactgc acaataactc tgccgtccgg cgttgttccg agattcgaat ggagccttaa   7320
taatgtttca ctgccggaat atttgacggc cacgaccgtt gtttcgcata ccgctggcca   7380
aagtacagtg tggaagagca gcgcgagagc aggcgaggcg tggatttctg gccggggagg   7440
caatatatac gaatgcaccg tcctcatctc agacggcact cgcgttacta cgcgaaagga   7500
gaggtgctta acaaacacat ggattgcggt ggaaaacggt gctgctcagg cgcagctgta   7560
ttcactcttt tctggacttg tgtcaggatt atgcgggagc atatctgctt tgtacgcaac   7620
gctatggacc gccatttatt tttgaggaat gctttttgga ctatcgtact gctttcttcc   7680
ttcgctagcc agagcaccgc cgccgtcacg tacgactaca ttttaggccg tcgcgcgctc   7740
gacgcgctaa ccataccggc ggttggcccg tataacagat acctcactag ggtatcaaga   7800
ggctgcgacg ttgtcgagct caacccgatt tctaacgtgg acgacatgat atcggcggcc   7860
aaagaaaaag agaagggggg ccctttcgag gcctccgtcg tctggttcta cgtgattaag   7920
ggcgacgacg gcgaggacaa gtactgtcca atctatagaa aagagtacag ggaatgtggc   7980
gacgtacaac tgctatctga atgcgccgtt caatctgcac agatgtgggc agtggactat   8040
gttcctagca cccttgtatc gcgaaatggc gcgggactga ctatattctc ccccactgct   8100
gcgctctctg gccaatactt gctgaccctg aaaatcggga gatttgcgca aacagctctc   8160
gtaactctag aagttaacga tcgctgttta aagatcgggt cgcagcttaa ctttttaccg   8220
tcgaaatgct ggacaacaga acagtatcag actggatttc aaggcgaaca cctttatccg   8280
atcgcagaca ccaatacacg acacgcggac gacgtatatc ggggatacga agatattctg   8340
cagcgctgga ataatttgct gaggaaaaag aatcctagcg cgccagaccc tcgtccagat   8400
agcgtcccgc aagaaattcc cgctgtaacc aagaaagcgg aagggcgcac cccggacgca   8460
gaaagcagcg aaaagaaggc ccctccagaa gactcggagg acgacatgca ggcagaggct   8520
tctggagaaa atcctgccgc cctccccgaa gacgacgaag tccccgagga caccgagcac   8580
gatgatccaa actcggatcc tgactattac aatgacatgc ccgccgtgat cccggtggag   8640
gagactacta aaagttctaa tgccgtctcc atgcccatat tcgcggcgtt cgtagcctgc   8700
gcggtcgcgc tcgtggggct actggtttgg agcatcgtaa aatgcgcgcg tagctaatcg   8760
agcctagaat aggtggtttc ttcctacatg ccacgcctca cgctcataat ataaatcaca   8820
tggaatagca taccaatgcc tattcattgg gacgttcgaa aagcatggca tcgctacttg   8880
gaactctggc tctccttgcc gcgacgctcg caccccttcgg cgcgatggga atcgtgatca   8940
ctggaaatca cgtctccgcc aggattgacg acgatcacat cgtgatcgtc gcgcctcgcc   9000
```

-continued

```
ccgaagctac aattcaactg cagctatttt tcatgcctgg ccagagaccc cacaaaccct   9060
actcaggaac cgtccgcgtc gcgtttcggt ctgatataac aaaccagtgc taccaggaac   9120
ttagcgagga gcgctttgaa aattgcactc atcgatcgtc ttctgttttt gtcggctgta   9180
aagtgaccga gtacacgttc tccgcctcga acagactaac cggacctcca cacccgttta   9240
agctcactat acgaaatcct cgtccgaacg acagcgggat gttctacgta attgttcggc   9300
tagacgacac caaagaaccc attgacgtct tcgcgatcca actatcggtg tatcaattcg   9360
cgaacaccgc cgcgactcgc ggactctatt ccaaggcttc gtgtcgcacc ttcggattac   9420
ctaccgtcca acttgaggcc tatctcagga ccgaggaaag ttggcgcaac tggcaagcgt   9480
acgttgccac ggaggccacg acgaccagcg ccgaggcgac aaccccgacg cccgtcactg   9540
caaccagcgc ctccgaactt gaagcggaac actttacctt tccctggcta gaaaatggcg   9600
tggatcatta cgaaccgaca cccgcaaacg aaaattcaaa cgttactgtc cgtctcggga   9660
caatgagccc tacgctaatt ggggtaaccg tggctgccgt cgtgagcgca acgatcggcc   9720
tcgtcattgt aatttccatc gtcaccagaa acatgtgcac cccgcaccga aaattagaca   9780
cggtctcgca agacgacgaa gaacgttccc aaactagaag ggaatcgcga aaatttggac   9840
ccatggttgc gtgcgaaata aacaaggggg ctgaccagga tagtgaactt gtggaactgg   9900
ttgcgattgt taacccgtct gcgctaagct cgcccgactc aataaaaatg tgattaagtc   9960
tgaatgtggc tctccaatca tttcgattct ctaatctccc aatcctctca aaaggggcag  10020
tatcggacac ggactgggag gggcgtacac gatagttata tggtacagca gaggcctctg  10080
aacacttagg aggagaattc agccggggag agcccctgtt gagtaggctt gggagcatat  10140
tgcaggatga acatgttagt gatagttctc gcctcttgtc ttgcgcgcct aacttttgcg  10200
acgcgacacg tcctcttttt ggaaggcact caggctgtcc tcggggaaga tgatcccaga  10260
aacgttccgg aagggactgt aatcaaatgg acaaaagtcc tgcggaacgc gtgcaagatg  10320
aaggcggccg atgtctgctc ttcgcctaac tattgctttc atgatttaat ttacgacgga  10380
ggaaagaaag actgcccgcc cgcgggaccc ctgtctgcaa acctggtaat tttactaaag  10440
cgcggcgaag cttagcttgc ctccgattct agcattacat agccggtcag tagatcctgc  10500
cattcggtag cgcaaccggc tacatcttca aacagtctca cgataaatgc atctctcgtt  10560
cctgccaatc cggaaccggg cataccactc ccgcctgccg atttaattct cacaattggg  10620
cgatgccggc ggggcaaaac gaatgtggat ttggcaaacc gacacaggtc tgctgtacgg  10680
actaatatgg gcacacccac atcattcttc agatgctcca tgcattgttc tatgagaaag  10740
atccataggg tggaggcagc gtcacgagat cgcccaggca atcgatcgca ttcgtctagt  10800
aaagtgacga gagttatcat gcacacaccc atgcccacgc cttccgaata actggagctg  10860
tggaagatcg gaaacgtctt tttgactgcc ggtctcgtac tactttcgca caggtgtata  10920
cccggacgcg tactatatat tttatatcat ccaacgtccg aaattacata cgtggcggcg  10980
atggaagtag atgttgagtc ttcgaaagta agtgcctcga atatgggtat tgtctgtgaa  11040
aatatcgaaa gcggtacgac ggttgcagaa ccgtcgatgt cgccagatac tagtaacaat  11100
agcttcgata acgaagactt ccgtgggcct gaatacgatg tggagataaa taccagaaaa  11160
tctgctaatc ttgatcgtat ggaatcttcg tgccgtgaac aacgagcggc gtgcgaactt  11220
cgaaagtgtt cgtgtcctac gtctgccgtg cgcatgcaat acagtattct ttcatctctc  11280
gctccgggtt cagagggtca tgtatatata tgtactagat acggggacgc ggaccaaaaa  11340
```

-continued aaatgcatag tgaaggcagt cgttggagga aagaatcccg ggagggaagt ggatatttta 11400
aaaaccatct cacataaatc aattataaaa ttaatccatg cctataaatg gaaaaatgtt 11460
gtgtgtatgg caatgcgtgt atatcgttat gatcttttca catatattga cggagtcggc 11520
cctatgcccc ttcaacagat gatctatatt caacgtggac tactagaggc gctagcatac 11580
atacatgaaa ggggcatcat tcaccgagac gtaaagacgg agaatatatt cttggataat 11640
cacgaaaatg cagttttggg tgacttcggt gctgcatgcc aactaggaga ttgtatagat 11700
acgccccaat gttacggttg gagcggaact gtggaaacaa attcgccgga attatctgca 11760
cttgatccgt attgcacaaa aacagatatt tggagtgccg gattggttct atatgagatg 11820
gcaattaaaa atgtaccatt gtttagtaag caggtgaaaa gttcgggatc tcagctgaga 11880
tccataatac ggtgcatgca agtgcatgaa ctggagtttc cccgcaacga ttctaccaac 11940
ctctgtaaac atttcaaaca atatgcggtt cgtgtacgac cgccttatac cattcctcga 12000
gttataagaa atgggggat gccaatggat gttgaatatg tcatttctaa aatgcttacg 12060
tttgaccagg agttcagacc ttctgctaag gaaatattga atatgcccct atttactaag 12120
gcgccgatta acctgcttaa tatcacaccc tctgacagtg tctaacggta tacaggcggg 12180
agcgggtcgt ggcgtcatca tcaccacttg agaatttata ttttgaattg ttgattgata 12240
aattaacctg attcattgag aactgaaacg ccatattggt ttcttggata tgtctacaac 12300
aattagttaa attgctatgt tctactgcga gtaacatttg ataagttgta agagacgggc 12360
gactcatgtc gaagttgacg aatataaagt acataacgtg tttagaatac ccagaatccg 12420
aatagtccgc gggggcgtct tctcgcgtga gtaccaaata ctgagttgaa cttgaaaatg 12480
ctaaatctgt gacactcttt gtgtgatgat tattgtcacc acttcgaaga tggcttcgac 12540
attcatgatg ttctggtgtt tgtttggaat cgtaatagcg cttgtttcgt ccaagtctga 12600
caacaaagaa aatctgaaga attatatcac ggataagtca accaatatta gaatacccac 12660
gccattattt gtatcaacgg aaaactctta tcccacaaaa catgtaatct acgatgaaaa 12720
ctgtggcttc gctgtactca atcctataag tgaccccaaa tatgtccttt tgagccagct 12780
tctaatggga aggcgcaaat atgatgcgac ggtcgcgtgg tttgttctcg gtaaaatgtg 12840
tgccagatta atatatttgc gcgaatttta taactgctcg acaaatgagc cttttggcac 12900
atgttctatg agctctcctg gatggtggga caggcgctac gtctcaacca gtttcatttc 12960
tcgcgacgaa ttacagctgg tttttgcagc gccgtcccga gaattagatg gtttatatac 13020
gcgcgtagta gttgtcaacg gggactttac tacggccgat ataatgttta atgttaaagt 13080
ggcatgtgcc ttttcaaaga ctggaataga agatgataca ttatgcaaac cctttcattt 13140
ctttgccaat gcaacattgc acaatttaac catgattaga tcggtaactc ttcgagcgca 13200
cgaaagccat ttaaaggaat gggtggcacg gagaggtggt aacgtccctg cagtgctact 13260
tgagtctacc atgtatcatg catccaatct gcctagaaat ttcagggatt tctacataaa 13320
gtctccagat gattataagt ataatcacct agatgggcca tctgtaatgc tcatcactga 13380
cagacctagt gaagatttgg atgggaggct cgttcaccaa agtgacattt ttactactac 13440
aagtcctata aaacaggtcc ggtatgaaga gcatcagtca catacaaagc agtatcctgt 13500
aaacaaaata caagctataa ttttttgat agggttaggc tcgttcattg gaagcatatt 13560
cgtagttttg gtagtatgga ttatacgcag atattgcaat ggagcgcgga gtgggggaac 13620
gcccccagt cctcgccggt atgtgtatac caggctatga tcacgtgtga aacttgggcg 13680
gacctgtatc atatgtacac cgtccctatt cgtttatagc cagtacgtgt tatctgcaca 13740

```
tagaggaaca tgtgtcatac tgggatcgca tgcatggtat gtgtgactct aatattattc  13800

tgtatcataa taaaaacaca gtgcatggta tatagaggat cgctggtaag cactacggta  13860

gaccaatcgg ctcagattgc attctttggc atcgataccg ttgttaattt atatggcaaa  13920

gtcttgttca tgggagatca gtatttggag gaaatatact ctggaacgat ggaaatactc  13980

aaatggaatc aagctaaccg ctgctattct attgcgcatg caacatatta cgccgactgt  14040

cctataatca gttctacggt attcagagga tgccgggacg ccgttgttta tactaggccc  14100

cacagcagaa ttc                                                     14113
```

<210> SEQ ID NO 16
<211> LENGTH: 13064
<212> TYPE: DNA
<213> ORGANISM: Artificial Sequence
<220> FEATURE:
<223> OTHER INFORMATION: Herpesvirus of turkeys, Infectious laryngotracheitis virus, Gallus gallus, Infectious bursal disease virus, and Feline Herpesvirus
<220> FEATURE:
<221> NAME/KEY: misc_feature
<222> LOCATION: (7401)..(7403)
<223> OTHER INFORMATION: n is a, c, g, or t

<400> SEQUENCE: 16

```
gaattccaga ctaaatgccc cggcccaatt tgtcaagtgt gcagtcacgg aggcgtcgac     60

cgtgtccccg gcattaaaca ggaaagcgtt aaagtttttg aatgttaggt cacaggtaca    120

aacataaatg tttgtacaaa caggtaacag gtacaaacat aaatgccccg gcataaatgt    180

cccttacggc ggatcgaaac gacattaggc atactcgggt accattttgc attccgatca    240

gcacggatga aattaggcag gaatgcggtt tatattatgc ggcattggac aaacgatatg    300

gcattgattg gcagtttatg aatgtcttca tgttgggcgt aaacggattc ctattggttc    360

agaagacaac gacgatatat ttagagagaa aaagctaccc agcataggat aaacacacat    420

tgagcattga gagacatagg tatcggtatg gatgggaaaa ctacacacgt gaacaccaaa    480

cgacttatat actcgagcgg tgatactact gagcaagaat gcactgcatc tgagccactg    540

aatgaagact gtgatgaaaa tgtgaccatc gatggaattg gagaagaata tgcgcagttc    600

ttcatgtccc cgcaatgggt cccaaatcta catcgcttga gcgaggatac caaaaaggta    660

taccgatgta tggtttccaa cagactcaat tattttccct attatgaggc gttcaggcgg    720

tctttgtttg atatgtatat gctaggtcgg ttggggcgtc gacttaagcg atctgactgg    780

gagactatta tgcatctgtc accaacgcaa agtcggcgtc tacatagaac tttaagattt    840

gtggagcgta gaattatccc atctaacagt tatatacgca catcgggcca cgttccgcct    900

tcgagggcac ttccgacaga tacgaattta aagatggatg aataattaaa ttggaaagag    960

taactacatt aatcgagcgt catgacggcg tcccgtgaaa atgggaattt tctactcgaa   1020

acaccgtgac atttgacaga cctggaattg ttattctgat atatagtggg tgtgtctggc   1080

cggcaacata cataatgtgc atgcgaaacc actttttcag tgtacgctga cattgtgcaa   1140

cacggagggg tagcatctac atacaatata tgttgattaa tgattggaga aaaaactatg   1200

cagctcgccg atcatatggc taactcgcct tcgtctatat ggcggacccc gcgggaaaaa   1260

tcgacgtacc atctgattta caacaccagt aatgaacatg tcgcatccct gcccagatct   1320

gtgcgcccat tggcgcggat cgttgtgaat gccgccgaaa cacttcaggt cggtatgaga   1380

gccgggaggc cgccatcagc aggagtttgg cgagaggtgt ttgatagaat gatgacagcc   1440
```

-continued

```
ttccgtgacc acgagcctac tgcgacattt aatgctgcaa atcccattag aaaaatggtc   1500
gagacagttc tacagaataa tgaagagccc ccgcggacgc atgctgaaat gggtaatcgc   1560
cttatgaaca ttatgtactg gtgttgcttg ggacacgcag gacaatgctc gatatggcag   1620
ttgtacgaga cgaatcaggc cattttaagt ttattagatg aagtggttat cggcacaaca   1680
aatccctttt gcaccctcga gcaatactgg aagccattat gcaccgcaat cgccaacaag   1740
gggacctcat cgcttgttga ggatgccaaa gtggccgagt acctggttag catgcgcaaa   1800
ttgatataac ataggcacgc tctgatgtta cagaccacaa taccgcatac atttattgta   1860
aggttgttaa taaaggttta ttctatgtaa gactacaata ctttcgacat tgcttgtata   1920
catattaaat actttctcaa gttcctatta cataaaatgg gatctatcat tacattcgtt   1980
aagagtctgg ataattttac tgtttgccag cttcgatctt ggaacgtact gtggatagtg   2040
ccttacttgg aatcgtgaaa atttgaaacg tccattattt ggatatcttc cggttgtccc   2100
atatcccgcc ctggtaccgc tcggatacct tgcccgtatg gattcgtatt gacagtcgcg   2160
caatcgggga ccaacaacgc gtgggtccac actcattcgg aaattttccg atgattctga   2220
atatttattg ccgctcgtta cgagtcgttg gacatatctg taatacattt cttcttctga   2280
aggatcgctg cacatttgat ctatacattg gccaggatgt tcaagtctca gatgttgcat   2340
tctggcacag cacaacttta tggcatttcc gatgtaatcg tccggcagcc ctgggggagt   2400
tctatattcg catattggga tggtaaggac aatagcagat ctcgcaacct ccagggaggc   2460
tataataacg tttttaaagg atggatttct cataaaaatc tgtcgcaaat tacactgaga   2520
atatccttta ctagcgccga ttgagagcat cgtcgtccaa ttttctaaat ggaaagaaaa   2580
caaggcgggc aagagtgttc caaacatttt catttcggc gaatctctca aatcccatgg   2640
cgtgcaattg attgcaaaat tggcacttcc gttcacgttt gtatctccaa actctaagac   2700
acttttaatt gaaaaactac gttctagtgt ggaaagaaac ctataggcag accatagaac   2760
tatttgacac cacatatctt tttgtatgtc aaactgacca tgatcgtatg ttgctgaatg   2820
cactagggca attcgctcgc gcgactccat acattgaata attccacacg tcagctcatc   2880
ggttagcaag gtccagtagt tgaagtcatt tatttttccc cgcggctggc caaatctacc   2940
tctgggaata tccaagttgt cgaatatgat cgcaccggct ctggtcatgg tgaaggaact   3000
gtagcataaa gacgcaggta tcataggggt aatattttt tattcactca catactaaaa   3060
gtaacgcata ttagcaccat gtatgggcta tcaattgaca tttgcgtagc actacatcac   3120
gattatgtac aacataatgg gacaacatat ggcaagtaga tgcaatttcc tcacactagt   3180
tgggtttatc tactattgaa ttttccccta tctgtgatac acttgggagc ctctacaagc   3240
atattgccat catgtacgtt tttatctact gtcttaacgc ccatgggaac ggaggcgtcg   3300
tcgtcatgta ttggacggca acataggcag caacacaaat tgcgtttagg tggggtgcat   3360
gtggactcga taccaagccc ctgcagctgg ggaacgtctg gtggagagcc gataatttga   3420
tatacgcacg ccatattact gtcgttgaag tacgccttat cttctatgtt ttcaaattta   3480
ggttcccaag tggacgtgag aagtgtttgt atctcacatg gaatggccca aggcattcca   3540
gcccaggtgc ctggtacttt aatggcaaac aaacgttttg gtagaggtat tgattctatt   3600
gcagttctgc agatatctgc agccccgagt atccacaggc tatacgatac gttatcggag   3660
gcaagcttaa ttaagtaccg agctcgaatt ggcgcgcccg acggcagagt cgcagacgcc   3720
cctattggac gtcaaaattg tagaggtgaa gttttcaaac gatggcgaag taacggcgac   3780
ttgcgtttcc accgtcaaat ctccctatag ggtagaaact aattggaaag tagacctcgt   3840
```

```
agatgtaatg gatgaaattt ctgggaacag tcccgccggg gtttttaaca gtaatgagaa   3900
atggcagaaa cagctgtact acagagtaac cgatggaaga acatcggtcc agctaatgtg   3960
cctgtcgtgc acgagccatt ctccggaacc ttactgtctt ttcgacacgt ctcttatagc   4020
gagggaaaaa gatatcgcgc cagagttata ctttacctct gatccgcaaa cggcatactg   4080
cacaataact ctgccgtccg gcgttgttcc gagattcgaa tggagcctta ataatgtttc   4140
actgccggaa tatttgacgg ccacgaccgt tgtttcgcat accgctggcc aaagtacagt   4200
gtggaagagc agcgcgagag caggcgaggc gtggatttct ggccggggag gcaatatata   4260
cgaatgcacc gtcctcatct cagacggcac tcgcgttact acgcgaaagg agaggtgctt   4320
aacaaacaca tggattgcgg tggaaaacgg tgctgctcag gcgcagctgt attcactctt   4380
ttctggactt gtgtcaggat tatgcgggag catatctgct ttgtacgcaa cgctatggac   4440
cgccatttat ttttgaggaa tgctttttgg actatcgtac tgctttcttc cttcgctagc   4500
cagagcaccg ccgccgtcac gtacgactac attttaggcc gtcgcgcgct cgacgcgcta   4560
accataccgg cggttggccc gtataacaga tacctcacta gggtatcaag aggctgcgac   4620
gttgtcgagc tcaacccgat ttctaacgtg gacgacatga tatcggcggc caaagaaaaa   4680
gagaaggggg gccctttcga ggcctccgtc gtctggttct acgtgattaa gggcgacgac   4740
ggcgaggaca agtactgtcc aatctataga aaagagtaca gggaatgtgg cgacgtacaa   4800
ctgctatctg aatgcgccgt tcaatctgca cagatgtggg cagtggacta tgttcctagc   4860
acccttgtat cgcgaaatgg cgcgggactg actatattct cccccactgc tgcgctctct   4920
ggccaatact tgctgaccct gaaaatcggg agatttgcgc aaacagctct cgtaactcta   4980
gaagttaacg atcgctgttt aaagatcggg tcgcagctta actttttacc gtcgaaatgc   5040
tggacaacag aacagtatca gactggattt caaggcgaac acctttatcc gatcgcagac   5100
accaatacac gacacgcgga cgacgtatat cggggatacg aagatattct gcagcgctgg   5160
aataatttgc tgaggaaaaa gaatcctagc gcgccagacc ctcgtccaga tagcgtcccg   5220
caagaaattc ccgctgtaac caagaaagcg gaagggcgca ccccggacgc agaaagcagc   5280
gaaaagaagg cccctccaga agactcggag gacgacatgc aggcagaggc ttctggagaa   5340
aatcctgccg ccctccccga agacgacgaa gtccccgagg acaccgagca cgatgatcca   5400
aactcggatc ctgactatta caatgacatg cccgccgtga tcccggtgga ggagactact   5460
aaaagttcta atgccgtctc catgcccata ttcgcggcgt tcgtagcctg cgcggtcgcg   5520
ctcgtggggc tactggtttg gagcatcgta aaatgcgcgc gtagctaatc gagcctagaa   5580
taggtggttt cttcctacat gccacgcctc acgctcataa tataaatcac atggaatagc   5640
ataccaatgc ctattcattg ggacgttcga aaagcatggc atcgctactt ggaactctgg   5700
ctctccttgc cgcgacgctc gcacccttcg gcgcgatggg aatcgtgatc actggaaatc   5760
acgtctccgc caggattgac gacgatcaca tcgtgatcgt cgcgcctcgc cccgaagcta   5820
caattcaact gcagctattt ttcatgcctg gccagagacc ccacaaaccc tactcaggaa   5880
ccgtccgcgt cgcgtttcgg tctgatataa caaaccagtg ctaccaggaa cttagcgagg   5940
agcgctttga aaattgcact catcgatcgt cttctgtttt tgtcggctgt aaagtgaccg   6000
agtacacgtt ctccgcctcg aacagactaa ccggacctcc acacccgttt aagctcacta   6060
tacgaaatcc tcgtccgaac gacagcggga tgttctacgt aattgttcgg ctagacgaca   6120
ccaaagaacc cattgacgtc ttcgcgatcc aactatcggt gtatcaattc gcgaacaccg   6180
```

-continued

```
ccgcgactcg cggactctat tccaaggctt cgtgtcgcac cttcggatta cctaccgtcc   6240
aacttgaggc ctatctcagg accgaggaaa gttggcgcaa ctggcaagcg tacgttgcca   6300
cggaggccac gacgaccagc gccgaggcga caaccccgac gcccgtcact gcaaccagcg   6360
cctccgaact tgaagcggaa cactttacct ttccctggct agaaaatggc gtggatcatt   6420
acgaaccgac acccgcaaac gaaaattcaa acgttactgt ccgtctcggg acaatgagcc   6480
ctacgctaat tggggtaacc gtggctgccg tcgtgagcgc aacgatcggc ctcgtcattg   6540
taatttccat cgtcaccaga aacatgtgca ccccgcaccg aaaattagac acggtctcgc   6600
aagacgacga agaacgttcc caaactagaa gggaatcgcg aaaatttgga cccatggttg   6660
cgtgcgaaat aaacaagggg gctgaccagg atagtgaact tgtggaactg gttgcgattg   6720
ttaacccgtc tgcgctaagc tcgcccgact caataaaaat gtgattaagt ctgaatgtgg   6780
ctctccaatc atttcgattc tctaatctcc caatcctctc aaaaggggca gtatcggaca   6840
cggactggga ggggcgtaca cgatagttat atggtacagc agaggcctct gaacacttag   6900
gaggagaatt cagccgggga gagcccctgt tgagtaggct tgggagcata ttgcaggatg   6960
aacatgttag tgatagttct cgcctcttgt cttgcgcgcc taacttttgc gacgcgacac   7020
gtcctctttt tggaaggcac tcaggctgtc ctcggggaag atgatcccag aaacgttccg   7080
gaagggactg taatcaaatg gacaaaagtc ctgcggaacg cgtgcaagat gaaggcggcc   7140
gatgtctgct cttcgcctaa ctattgcttt catgatttaa tttacgacgg aggaaagaaa   7200
gactgcccgc ccgcgggacc cctgtctgca aacctggtaa ttttactaaa gcgcggcggg   7260
cgcgccggat cagatctcca tggtcgaggt gagccccacg ttctgcttca ctctccccat   7320
ctcccccccc tccccacccc caattttgta tttatttatt ttttaattat tttgtgcagc   7380
gatgggggcg gggggggggg nnncgcgcgc caggcggggc ggggcggggc gaggggcggg   7440
gcggggcgag gcggagaggt gcggcggcag ccaatcagag cggcgcgctc cgaaagtttc   7500
cttttatggc gaggcggcgg cggcggcggc cctataaaaa gcgaagcgcg cggcgggcgg   7560
gagtcgctgc gcgctgcctt cgccccgtgc cccgctccgc cgccgcctcg cgccgcccgc   7620
cccggctctg actgaccgcg ttactcccac aggtgagcgg gcgggacggc ccttctcctc   7680
cgggctgtaa ttagcggcag gaaggaaatg ggcggggagg gccttcgtgc gtcgccgcgc   7740
cgccgtcccc ttctccctct ccagcctcgg ggctgtccgc ggggggacgg ctgccttcgg   7800
gggggacggg gcagggcggg gttcggcttc tggcgtgtga ccggcggctc tagagcctct   7860
gctaaccatg ttcatgcctt cttctttttc ctacagctcc tgggcaacgt gctggttatt   7920
gtgctgtctc atcattttgg caaagaattg cagatctgga tctatgacaa acctgcaaga   7980
tcaaacccaa cagattgttc cgttcatacg gagccttctg atgccaacaa ccggaccggc   8040
gtccattccg gacgacaccc tggagaagca cactctcagg tcagagacct cgacctacaa   8100
tttgactgtg ggggacacag ggtcagggct aattgtcttt ttccctggat tccctggctc   8160
aattgtgggt gctcactaca cactgcagag caatgggaac tacaagttcg atcagatgct   8220
cctgactgcc cagaacctac cggccagcta caactactgc agactagtga gtcggagtct   8280
cacagtgagg tcaagcacac tccctggtgg cgtttatgca ctaaacggca ccataaacgc   8340
cgtgaccttc caaggaagcc tgagtgaact gacagatgtt agctacaatg ggttgatgtc   8400
tgcaacagcc aacatcaacg acaaagttgg gaatgtcctg gtaggggaag gggtcactgt   8460
cctcagccta cccacatcat atgatcttgg gtatgtgagg cttggtgacc ccattcccgc   8520
tatagggctt gacccaaaaa tggtagctac atgcgacagc agtgacaggc ccagagtcta   8580
```

-continued

```
caccataact gcagccgatg attaccaatt ctcatcacag taccaaccag gtggggtaac   8640
aatcacactg ttctcagcca acattgatgc tatcacaagc ctcagcattg gggagagct   8700
cgtgtttcaa acaagcgtcc aaggccttgt actgggcgcc accatctacc ttataggctt   8760
tgatgggact gcggtaatca ccagagctgt ggccgcagat aatgggctga cggccggcac   8820
cgacaatctt atgccattca atcttgtcat tccaaccaat gagataaccc agccgatcac   8880
atccatcaaa ctggagatag tgacctccaa aagtggtggt caggcagggg atcagatgtc   8940
atggtcggca agtgggagcc tagcagtgac gatccatggt ggcaactatc caggggccct   9000
ccgtcccgtc acactagtag cctacgaaag agtggcaaca ggatccgtcg ttacggtcgc   9060
tggggtgagt aacttcgagc tgatcccaaa tcctgaacta gcaaagaacc tggttacaga   9120
atacggccga tttgacccag gagccatgaa ctacacaaaa ttgatactga gtgagaggga   9180
ccgtcttggc atcaagaccg tctggccaac aagggagtac actgattttc gtgagtactt   9240
catggaggtg gccgacctca actctcccct gaagattgca ggagcatttg gcttcaaaga   9300
cataatccgg gctataagga ggtaagatcc gatctctcga ttaattaaca ataaacatag   9360
catacgttat gacatggtct accgcgtctt atatggggac gacaagcttg cctccgattc   9420
tagcattaca tagccggtca gtagatcctg ccattcggta gcgcaaccgg ctacatcttc   9480
aaacagtctc acgataaatg catctctcgt tcctgccaat ccggaaccgg gcataccact   9540
cccgcctgcc gatttaattc tcacaattgg gcgatgccgg cggggcaaaa cgaatgtgga   9600
tttggcaaac cgacacaggt ctgctgtacg gactaatatg ggcacaccca catcattctt   9660
cagatgctcc atgcattgtt ctatgagaaa gatccatagg gtggaggcag cgtcacgaga   9720
tcgcccaggc aatcgatcgc attcgtctag taaagtgacg agagttatca tgcacacacc   9780
catgcccacg ccttccgaat aactggagct gtggaagatc ggaaacgtct ttttgactgc   9840
cggtctcgta ctactttcgc acaggtgtat acccggacgc gtactatata ttttatatca   9900
tccaacgtcc gaaattacat acgtggcggc gatggaagta gatgttgagt cttcgaaagt   9960
aagtgcctcg aatatgggta ttgtctgtga aaatatcgaa agcggtacga cggttgcaga  10020
accgtcgatg tcgccagata ctagtaacaa tagcttcgat aacgaagact tccgtgggcc  10080
tgaatacgat gtggagataa ataccagaaa atctgctaat cttgatcgta tggaatcttc  10140
gtgccgtgaa caacgagcgg cgtgcgaact tcgaaagtgt tcgtgtccta cgtctgccgt  10200
gcgcatgcaa tacagtattc tttcatctct cgctccgggt tcagagggtc atgtatatat  10260
atgtactaga tacggggacg cggaccaaaa aaaatgcata gtgaaggcag tcgttggagg  10320
aaagaatccc gggagggaag tggatatttt aaaaaccatc tcacataaat caattataaa  10380
attaatccat gcctataaat ggaaaaatgt tgtgtgtatg gcaatgcgtg tatatcgtta  10440
tgatcttttc acatatattg acggagtcgg ccctatgccc cttcaacaga tgatctatat  10500
tcaacgtgga ctactagagg cgctagcata catacatgaa aggggcatca ttcaccgaga  10560
cgtaaagacg gagaatatat tcttggataa tcacgaaaat gcagttttgg gtgacttcgg  10620
tgctgcatgc caactaggag attgtataga tacgccccaa tgttacggtt ggagcggaac  10680
tgtggaaaca aattcgccgg aattatctgc acttgatccg tattgcacaa aaacagatat  10740
ttggagtgcc ggattggttc tatatgagat ggcaattaaa aatgtaccat tgtttagtaa  10800
gcaggtgaaa agttcgggat ctcagctgag atccataata cggtgcatgc aagtgcatga  10860
actggagttt ccccgcaacg attctaccaa cctctgtaaa catttcaaac aatatgcggt  10920
```

-continued

```
tcgtgtacga ccgccttata ccattcctcg agttataaga aatgggggga tgccaatgga  10980
tgttgaatat gtcatttcta aaatgcttac gtttgaccag gagttcagac cttctgctaa  11040
ggaaatattg aatatgcccc tatttactaa ggcgccgatt aacctgctta atatcacacc  11100
ctctgacagt gtctaacggt atacaggcgg gagcgggtcg tggcgtcatc atcaccactt  11160
gagaatttat attttgaatt gttgattgat aaattaacct gattcattga gaactgaaac  11220
gccatattgg tttcttggat atgtctacaa caattagtta aattgctatg ttctactgcg  11280
agtaacattt gataagttgt aagagacggg cgactcatgt cgaagttgac gaatataaag  11340
tacataacgt gtttagaata cccagaatcc gaatagtccg cgggggcgtc ttctcgcgtg  11400
agtaccaaat actgagttga acttgaaaat gctaaatctg tgacactctt tgtgtgatga  11460
ttattgtcac cacttcgaag atggcttcga cattcatgat gttctggtgt ttgtttggaa  11520
tcgtaatagc gcttgtttcg tccaagtctg acaacaaaga aaatctgaag aattatatca  11580
cggataagtc aaccaatatt agaataccca cgccattatt tgtatcaacg gaaaactctt  11640
atcccacaaa acatgtaatc tacgatgaaa actgtggctt cgctgtactc aatcctataa  11700
gtgaccccaa atatgtcctt ttgagccagc ttctaatggg aaggcgcaaa tatgatgcga  11760
cggtcgcgtg gtttgttctc ggtaaaatgt gtgccagatt aatatatttg cgcgaatttt  11820
ataactgctc gacaaatgag ccttttggca catgttctat gagctctcct ggatggtggg  11880
acaggcgcta cgtctcaacc agtttcattt ctcgcgacga attacagctg gtttttgcag  11940
cgccgtcccg agaattagat ggtttatata cgcgcgtagt agttgtcaac ggggacttta  12000
ctacggccga tataatgttt aatgttaaag tggcatgtgc cttttcaaag actggaatag  12060
aagatgatac attatgcaaa ccctttcatt tctttgccaa tgcaacattg cacaatttaa  12120
ccatgattag atcggtaact cttcgagcgc acgaaagcca tttaaaggaa tgggtggcac  12180
ggagaggtgg taacgtccct gcagtgctac ttgagtctac catgtatcat gcatccaatc  12240
tgcctagaaa tttcagggat ttctacataa agtctccaga tgattataag tataatcacc  12300
tagatgggcc atctgtaatg ctcatcactg acagacctag tgaagatttg gatgggaggc  12360
tcgttcacca aagtgacatt tttactacta caagtcctat aaaacaggtc cggtatgaag  12420
agcatcagtc acatacaaag cagtatcctg taaacaaaat acaagctata atttttttga  12480
tagggttagg ctcgttcatt ggaagcatat tcgtagtttt ggtagtatgg attatacgca  12540
gatattgcaa tggagcgcgg agtgggggaa cgccccccag tcctcgccgg tatgtgtata  12600
ccaggctatg atcacgtgtg aaacttgggc ggacctgtat catatgtaca ccgtccctat  12660
tcgtttatag ccagtacgtg ttatctgcac atagaggaac atgtgtcata ctgggatcgc  12720
atgcatggta tgtgtgactc taatattatt ctgtatcata ataaaaacac agtgcatggt  12780
atatagagga tcgctggtaa gcactacggt agaccaatcg gctcagattg cattctttgg  12840
catcgatacc gttgttaatt tatatggcaa agtcttgttc atgggagatc agtatttgga  12900
ggaaatatac tctggaacga tggaaatact caaatggaat caagctaacc gctgctattc  12960
tattgcgcat gcaacatatt acgccgactg tcctataatc agttctacgg tattcagagg  13020
atgccgggac gccgttgttt atactaggcc ccacagcaga attc                   13064
```

<210> SEQ ID NO 17
<211> LENGTH: 13017
<212> TYPE: DNA
<213> ORGANISM: Artificial Sequence
<220> FEATURE:
<223> OTHER INFORMATION: Herpesvirus of turkeys, Infectious laryngotracheitis virus, human cytomegalovirus, Infectious bursal disease virus, and Herpes simplex virus

<400> SEQUENCE: 17

```
gaattccaga ctaaatgccc cggcccaatt tgtcaagtgt gcagtcacgg aggcgtcgac     60
cgtgtccccg gcattaaaca ggaaagcgtt aaagtttttg aatgttaggt cacaggtaca    120
aacataaatg tttgtacaaa caggtaacag gtacaaacat aaatgccccg gcataaatgt    180
cccttacggc ggatcgaaac gacattaggc atactcgggt accattttgc attccgatca    240
gcacggatga aattaggcag gaatgcggtt tatattatgc ggcattggac aaacgatatg    300
gcattgattg gcagtttatg aatgtcttca tgttgggcgt aaacggattc ctattggttc    360
agaagacaac gacgatatat ttagagagaa aaagctaccc agcataggat aaacacacat    420
tgagcattga gagacatagg tatcggtatg gatgggaaaa ctacacacgt gaacaccaaa    480
cgacttatat actcgagcgg tgatactact gagcaagaat gcactgcatc tgagccactg    540
aatgaagact gtgatgaaaa tgtgaccatc gatggaattg gagaagaata tgcgcagttc    600
ttcatgtccc cgcaatgggt cccaaatcta catcgcttga gcgaggatac caaaaaggta    660
taccgatgta tggtttccaa cagactcaat tattttccct attatgaggc gttcaggcgg    720
tctttgtttg atatgtatat gctaggtcgg ttggggcgtc gacttaagcg atctgactgg    780
gagactatta tgcatctgtc accaacgcaa agtcggcgtc tacatagaac tttaagattt    840
gtggagcgta gaattatccc atctaacagt tatatacgca catcgggcca cgttccgcct    900
tcgagggcac ttccgacaga tacgaattta aagatggatg aataattaaa ttggaaagag    960
taactacatt aatcgagcgt catgacggcg tcccgtgaaa atgggaattt tctactcgaa   1020
acaccgtgac atttgacaga cctggaattg ttattctgat atatagtggg tgtgtctggc   1080
cggcaacata cataatgtgc atgcgaaacc actttttcag tgtacgctga cattgtgcaa   1140
cacggagggg tagcatctac atacaatata tgttgattaa tgattggaga aaaaactatg   1200
cagctcgccg atcatatggc taactcgcct tcgtctatat ggcggacccc gcgggaaaaa   1260
tcgacgtacc atctgattta caacaccagt aatgaacatg tcgcatccct gcccagatct   1320
gtgcgcccat tggcgcggat cgttgtgaat gccgccgaaa cacttcaggt cggtatgaga   1380
gccgggaggc cgccatcagc aggagtttgg cgagaggtgt ttgatagaat gatgacagcc   1440
ttccgtgacc acgagcctac tgcgacattt aatgctgcaa atcccattag aaaaatggtc   1500
gagacagttc tacagaataa tgaagagccc ccgcggacgc atgctgaaat gggtaatcgc   1560
cttatgaaca ttatgtactg gtgttgcttg ggacacgcag gacaatgctc gatatggcag   1620
ttgtacgaga cgaatcaggc cattttaagt ttattagatg aagtggttat cggcacaaca   1680
aatccctttt gcaccctcga gcaatactgg aagccattat gcaccgcaat cgccaacaag   1740
gggacctcat cgcttgttga ggatgccaaa gtggccgagt acctggttag catgcgcaaa   1800
ttgatataac ataggcacgc tctgatgtta cagaccacaa taccgcatac atttattgta   1860
aggttgttaa taaaggttta ttctatgtaa gactacaata ctttcgacat tgcttgtata   1920
catattaaat actttctcaa gttcctatta cataaaatgg gatctatcat tacattcgtt   1980
aagagtctgg ataattttac tgtttgccag cttcgatctt ggaacgtact gtggatagtg   2040
ccttacttgg aatcgtgaaa atttgaaacg tccattattt ggatatcttc cggttgtccc   2100
atatcccgcc ctggtaccgc tcggatacct tgcccgtatg gattcgtatt gacagtcgcg   2160
caatcgggga ccaacaacgc gtgggtccac actcattcgg aaattttccg atgattctga   2220
```

-continued

```
atatttattg ccgctcgtta cgagtcgttg gacatatctg taatacattt cttcttctga   2280
aggatcgctg cacatttgat ctatacattg gccaggatgt tcaagtctca gatgttgcat   2340
tctggcacag cacaacttta tggcatttcc gatgtaatcg tccggcagcc ctgggggagt   2400
tctatattcg catattggga tggtaaggac aatagcagat ctcgcaacct ccagggaggc   2460
tataataacg tttttaaagg atggatttct cataaaaatc tgtcgcaaat tacactgaga   2520
atatccttta ctagcgccga ttgagagcat cgtcgtccaa ttttctaaat ggaaagaaaa   2580
caaggcgggc aagagtgttc caaacatttt cattttcggc gaatctctca aatcccatgg   2640
cgtgcaattg attgcaaaat tggcacttcc gttcacgttt gtatctccaa actctaagac   2700
acttttaatt gaaaaactac gttctagtgt ggaaagaaac ctataggcag accatagaac   2760
tatttgacac cacatatctt tttgtatgtc aaactgacca tgatcgtatg ttgctgaatg   2820
cactagggca attcgctcgc gcgactccat acattgaata attccacacg tcagctcatc   2880
ggttagcaag gtccagtagt tgaagtcatt tatttttccc cgcggctggc caaatctacc   2940
tctgggaata tccaagttgt cgaatatgat cgcaccggct ctggtcatgg tgaaggaact   3000
gtagcataaa gacgcaggta tcataggggt aatattttt tattcactca catactaaaa   3060
gtaacgcata ttagcaccat gtatgggcta tcaattgaca tttgcgtagc actacatcac   3120
gattatgtac aacataatgg gacaacatat ggcaagtaga tgcaatttcc tcacactagt   3180
tgggtttatc tactattgaa ttttccccta tctgtgatac acttgggagc ctctacaagc   3240
atattgccat catgtacgtt tttatctact gtcttaacgc ccatgggaac ggaggcgtcg   3300
tcgtcatgta ttggacggca acataggcag caacacaaat tgcgtttagg tggggtgcat   3360
gtggactcga taccaagccc ctgcagctgg ggaacgtctg gtggagagcc gataatttga   3420
tatacgcacg ccatattact gtcgttgaag tacgccttat cttctatgtt ttcaaattta   3480
ggttcccaag tggacgtgag aagtgtttgt atctcacatg gaatggccca aggcattcca   3540
gcccaggtgc ctggtacttt aatggcaaac aaacgttttg gtagaggtat tgattctatt   3600
gcagttctgc agatatctgc agccccgagt atccacaggc tatacgatac gttatcggag   3660
gcaagcttgt taattaagtc gacggcagag tcgcagacgc ccctattgga cgtcaaaatt   3720
gtagaggtga agttttcaaa cgatggcgaa gtaacggcga cttgcgtttc caccgtcaaa   3780
tctccctata gggtagaaac taattggaaa gtagacctcg tagatgtaat ggatgaaatt   3840
tctgggaaca gtcccgccgg ggtttttaac agtaatgaga aatggcagaa acagctgtac   3900
tacagagtaa ccgatggaag aacatcggtc cagctaatgt gcctgtcgtg cacgagccat   3960
tctccggaac cttactgtct tttcgacacg tctcttatag cgagggaaaa agatatcgcg   4020
ccagagttat actttacctc tgatccgcaa acggcatact gcacaataac tctgccgtcc   4080
ggcgttgttc cgagattcga atggagcctt aataatgttt cactgccgga atatttgacg   4140
gccacgaccg ttgtttcgca taccgctggc caaagtacag tgtggaagag cagcgcgaga   4200
gcaggcgagg cgtggatttc tggccgggga ggcaatatat acgaatgcac cgtcctcatc   4260
tcagacggca ctcgcgttac tacgcgaaag gagaggtgct taacaaacac atggattgcg   4320
gtggaaaacg gtgctgctca ggcgcagctg tattcactct tttctggact tgtgtcagga   4380
ttatgcggga gcatatctgc tttgtacgca acgctatgga ccgccattta tttttgagga   4440
atgcttttg gactatcgta ctgctttctt ccttcgctag ccagagcacc gccgccgtca   4500
cgtacgacta cattttaggc cgtcgcgcgc tcgacgcgct aaccataccg gcggttggcc   4560
cgtataacag atacctcact agggtatcaa gaggctgcga cgttgtcgag ctcaacccga   4620
```

-continued

```
tttctaacgt ggacgacatg atatcggcgg ccaaagaaaa agagaagggg ggccctttcg   4680
aggcctccgt cgtctggttc tacgtgatta agggcgacga cggcgaggac aagtactgtc   4740
caatctatag aaaagagtac agggaatgtg gcgacgtaca actgctatct gaatgcgccg   4800
ttcaatctgc acagatgtgg gcagtggact atgttcctag caccccttgta tcgcgaaatg   4860
gcgcgggact gactatattc tcccccactg ctgcgctctc tggccaatac ttgctgaccc   4920
tgaaaatcgg gagatttgcg caaacagctc tcgtaactct agaagttaac gatcgctgtt   4980
taaagatcgg gtcgcagctt aactttttac cgtcgaaatg ctggacaaca gaacagtatc   5040
agactggatt tcaaggcgaa cacctttatc cgatcgcaga caccaataca cgacacgcgg   5100
acgacgtata tcggggatac gaagatattc tgcagcgctg gaataatttg ctgaggaaaa   5160
agaatcctag cgcgccagac cctcgtccag atagcgtccc gcaagaaatt cccgctgtaa   5220
ccaagaaagc ggaagggcgc accccggacg cagaaagcag cgaaaagaag gcccctccag   5280
aagactcgga ggacgacatg caggcagagg cttctggaga aaatcctgcc gccctccccg   5340
aagacgacga agtccccgag gacaccgagc acgatgatcc aaactcggat cctgactatt   5400
acaatgacat gcccgccgtg atcccggtgg aggagactac taaaagttct aatgccgtct   5460
ccatgcccat attcgcggcg ttcgtagcct gcgcggtcgc gctcgtgggg ctactggttt   5520
ggagcatcgt aaaatgcgcg cgtagctaat cgagcctaga ataggtggtt tcttcctaca   5580
tgccacgcct cacgctcata atataaatca catggaatag cataccaatg cctattcatt   5640
gggacgttcg aaaagcatgg catcgctact tggaactctg gctctccttg ccgcgacgct   5700
cgcacccttc ggcgcgatgg gaatcgtgat cactggaaat cacgtctccg ccaggattga   5760
cgacgatcac atcgtgatcg tcgcgcctcg ccccgaagct acaattcaac tgcagctatt   5820
tttcatgcct ggccagagac cccacaaacc ctactcagga accgtccgcg tcgcgtttcg   5880
gtctgatata acaaaccagt gctaccagga acttagcgag gagcgctttg aaaattgcac   5940
tcatcgatcg tcttctgttt ttgtcggctg taaagtgacc gagtacacgt tctccgcctc   6000
gaacagacta accggacctc cacacccgtt taagctcact atacgaaatc ctcgtccgaa   6060
cgacagcggg atgttctacg taattgttcg gctagacgac accaaagaac ccattgacgt   6120
cttcgcgatc caactatcgg tgtatcaatt cgcgaacacc gccgcgactc gcggactcta   6180
ttccaaggct tcgtgtcgca ccttcggatt acctaccgtc caacttgagg cctatctcag   6240
gaccgaggaa agttggcgca actggcaagc gtacgttgcc acggaggcca cgacgaccag   6300
cgccgaggcg acaaccccga cgcccgtcac tgcaaccagc gcctccgaac ttgaagcgga   6360
acactttacc tttccctggc tagaaaatgg cgtggatcat tacgaaccga cacccgcaaa   6420
cgaaaattca aacgttactg tccgtctcgg gacaatgagc cctacgctaa ttggggtaac   6480
cgtggctgcc gtcgtgagcg caacgatcgg cctcgtcatt gtaatttcca tcgtcaccag   6540
aaacatgtgc accccgcacc gaaaattaga cacggtctcg caagacgacg aagaacgttc   6600
ccaaactaga agggaatcgc gaaaatttgg acccatggtt gcgtgcgaaa taaacaaggg   6660
ggctgaccag gatagtgaac ttgtggaact ggttgcgatt gttaacccgt ctgcgctaag   6720
ctcgcccgac tcaataaaaa tgtgattaag tctgaatgtg gctctccaat catttcgatt   6780
ctctaatctc ccaatcctct caaaaggggc agtatcggac acggactggg aggggcgtac   6840
acgatagtta tatggtacag cagaggcctc tgaacactta ggaggagaat tcagccgggg   6900
agagcccctg ttgagtaggc ttgggagcat attgcaggat gaacatgtta gtgatagttc   6960
```

-continued

```
tcgcctcttg tcttgcgcgc ctaacttttg cgacgcgaca cgtcctcttt ttggaaggca   7020
ctcaggctgt cctcggggaa gatgatccca gaaacgttcc ggaagggact gtaatcaaat   7080
ggacaaaagt cctgcggaac gcgtgcaaga tgaaggcggc cgatgtctgc tcttcgccta   7140
actattgctt tcatgattta atttacgacg gaggaaagaa agactgcccg cccgcgggac   7200
ccctgtctgc aaacctggta attttactaa agcgcggcga aagcttaggt caattccctg   7260
gcattatgcc cagtacatga ccttatggga ctttcctact tggcagtaca tctacgtatt   7320
agtcatcgct attaccatgg tgatgcggtt ttggcagtac atcaatgggc gtggatagcg   7380
gtttgactca cggggatttc caagtctcca ccccattgac gtcaatggga gtttgttttg   7440
gcaccaaaat caacgggact ttccaaaatg tcgtaacaac tccgccccat tgacgcaaat   7500
gggcggtagg cgtgtacggt gggaggtcta tataagcaga gctcgtttag tgaaccgtca   7560
gatcgcctgg agacgccatc cacgctgttt tgacctccat agaagacacc gggcgcgccg   7620
gatctatgac aaacctgcaa gatcaaaccc aacagattgt tccgttcata cggagccttc   7680
tgatgccaac aaccggaccg gcgtccattc cggacgacac cctggagaag cacactctca   7740
ggtcagagac ctcgacctac aatttgactg tgggggacac agggtcaggg ctaattgtct   7800
ttttccctgg attccctggc tcaattgtgg gtgctcacta cacactgcag agcaatggga   7860
actacaagtt cgatcagatg ctcctgactg cccagaacct accggccagc tacaactact   7920
gcagactagt gagtcggagt ctcacagtga ggtcaagcac actccctggt ggcgtttatg   7980
cactaaacgg caccataaac gccgtgacct tccaaggaag cctgagtgaa ctgacagatg   8040
ttagctacaa tgggttgatg tctgcaacag ccaacatcaa cgacaaagtt gggaatgtcc   8100
tggtagggga aggggtcact gtcctcagcc tacccacatc atatgatctt gggtatgtga   8160
ggcttggtga ccccattccc gctatagggc ttgacccaaa aatggtagct acatgcgaca   8220
gcagtgacag gcccagagtc tacaccataa ctgcagccga tgattaccaa ttctcatcac   8280
agtaccaacc aggtggggta acaatcacac tgttctcagc caacattgat gctatcacaa   8340
gcctcagcat tgggggagag ctcgtgtttc aaacaagcgt ccaaggcctt gtactgggcg   8400
ccaccatcta ccttataggc tttgatggga ctgcggtaat caccagagct gtggccgcag   8460
ataatgggct gacggccggc accgacaatc ttatgccatt caatcttgtc attccaacca   8520
atgagataac ccagccgatc acatccatca aactggagat agtgacctcc aaaagtggtg   8580
gtcaggcagg ggatcagatg tcatggtcgg caagtgggag cctagcagtg acgatccatg   8640
gtggcaacta tccaggggcc ctccgtcccg tcacactagt agcctacgaa agagtggcaa   8700
caggatccgt cgttacggtc gctggggtga gtaacttcga gctgatccca aatcctgaac   8760
tagcaaagaa cctggttaca gaatacggcc gatttgaccc aggagccatg aactacacaa   8820
aattgatact gagtgagagg gaccgtcttg gcatcaagac cgtctggcca acaagggagt   8880
acactgattt tcgtgagtac ttcatggagg tggccgacct caactctccc ctgaagattg   8940
caggagcatt tggcttcaaa gacataatcc gggctataag gaggtaagat ccataattga   9000
ttgacgggag atgggggagg ctaactgaaa cacggaagga gacaataccg gaaggaaccc   9060
gcgctatgac ggcaataaaa agacagaata aaacgcacgg gtgttgggtc gtttgttcat   9120
aaacgcgggg ttcggtccca gggctggcac tctgtcgata ccccaccgag accccattgg   9180
ggccaatacg cccgcgtttc ttccttttcc ccaccccacc ccccaagttc gggtgaaggc   9240
ccagggctcg cagccaacgt cggggcggca ggccctgcca tagccactgg ccccgtgggt   9300
tagggacggg gtcccccatg gggaatggtt tatggttcgt gggggttatt attttgaagc   9360
```

-continued

```
ttgcctccga ttctagcatt acatagccgg tcagtagatc ctgccattcg gtagcgcaac   9420
cggctacatc ttcaaacagt ctcacaataa atgcatctct cgttcctgcc aatccggaac   9480
cgggcatacc actcccgcct gccgatttaa ttctcacaat tgggcgatgc cggcggggca   9540
aaacgaatgt ggatttggca aaccgacaca ggtctgctgt acggactaat atgggcacac   9600
ccacatcatt cttcagatgc tccatgcatt gttctatgag aaagatccat agggtggagg   9660
cagcgtcacg agatcgccca ggcaatcgat cgcattcgtc tagtaaagtg acgagagtta   9720
tcatgcacac acccatgccc acgccttccg aataactgga gctgtggaag atcggaaacg   9780
tctttttgac tgccggtctc gtactacttt cgcacaggtg tatacccgga cgcgtactat   9840
atattttata tcatccaacg tccgaaatta catacgtggc ggcgatggaa gtagatgttg   9900
agtcttcgaa agtaagtgcc tcgaatatgg gtattgtctg tgaaaatatc gaaagcggta   9960
cgacggttgc agaaccgtcg atgtcgccag atactagtaa caatagcttc gataacgaag  10020
acttccgtgg gcctgaatac gatgtggaga taaataccag aaaatctgct aatcttgatc  10080
gtatggaatc ttcgtgccgt gaacaacgag cggcgtgcga acttcgaaag tgttcgtgtc  10140
ctacgtctgc cgtgcgcatg caatacagta ttctttcatc tctcgctccg ggttcagagg  10200
gtcatgtata tatatgtact agatacgggg acgcggacca aaaaaaatgc atagtgaagg  10260
cagtcgttgg aggaaagaat cccgggaggg aagtggatat tttaaaaacc atctcacata  10320
aatcaattat aaaattaatc catgcctata aatggaaaaa tgttgtgtgt atggcaatgc  10380
gtgtatatcg ttatgatctt ttcacatata ttgacggagt cggccctatg ccccttcaac  10440
agatgatcta tattcaacgt ggactactag aggcgctagc atacatacat gaaaggggca  10500
tcattcaccg agacgtaaag acggagaata tattcttgga taatcacgaa aatgcagttt  10560
tgggtgactt cggtgctgca tgccaactag gagattgtat agatacgccc caatgttacg  10620
gttggagcgg aactgtggaa acaaattcgc cggaattatc tgcacttgat ccgtattgca  10680
caaaaacaga tatttggagt gccggattgg ttctatatga gatggcaatt aaaaatgtac  10740
cattgtttag taagcaggtg aaaagttcgg gatctcagct gagatccata atacggtgca  10800
tgcaagtgca tgaactggag tttccccgca acgattctac caacctctgt aaacatttca  10860
aacaatatgc ggttcgtgta cgaccgcctt ataccattcc tcgagttata agaaatgggg  10920
ggatgccaat ggatgttgaa tatgtcattt ctaaaatgct tacgtttgac caggagttca  10980
gaccttctgc taaggaaata ttgaatatgc ccctatttac taaggcgccg attaacctgc  11040
ttaatatcac accctctgac agtgtctaac ggtatacagg cgggagcggg tcgtggcgtc  11100
atcatcacca cttgagaatt tatattttga attgttgatt gataaattaa cctgattcat  11160
tgagaactga aacgccatat tggtttcttg gatatgtcta caacaattag ttaaattgct  11220
atgttctact gcgagtaaca tttgataagt tgtaagagac gggcgactca tgtcgaagtt  11280
gacgaatata aagtacataa cgtgtttaga atacccagaa tccgaatagt ccgcgggggc  11340
gtcttctcgc gtgagtacca aatactgagt tgaacttgaa aatgctaaat ctgtgacact  11400
ctttgtgtga tgattattgt caccacttcg aagatggctt cgacattcat gatgttctgg  11460
tgtttgtttg gaatcgtaat agcgcttgtt tcgtccaagt ctgacaacaa agaaaatctg  11520
aagaattata tcacggataa gtcaaccaat attagaatac ccacgccatt atttgtatca  11580
acggaaaact cttatcccac aaaacatgta atctacgatg aaaactgtgg cttcgctgta  11640
ctcaatccta taagtgaccc caaatatgtc cttttgagcc agcttctaat gggaaggcgc  11700
```

aaatatgatg cgacggtcgc gtggtttgtt ctcggtaaaa tgtgtgccag attaatatat 11760
ttgcgcgaat tttataactg ctcgacaaat gagccttttg gcacatgttc tatgagctct 11820
cctggatggt gggacaggcg ctacgtctca accagtttca tttctcgcga cgaattacag 11880
ctggtttttg cagcgccgtc ccgagaatta gatggtttat atacgcgcgt agtagttgtc 11940
aacggggact ttactacggc cgatataatg tttaatgtta aagtggcatg tgccttttca 12000
aagactggaa tagaagatga tacattatgc aaaccctttc atttctttgc caatgcaaca 12060
ttgcacaatt taaccatgat tagatcggta actcttcgag cgcacgaaag ccatttaaag 12120
gaatgggtgg cacggagagg tggtaacgtc cctgcagtgc tacttgagtc taccatgtat 12180
catgcatcca atctgcctag aaatttcagg gatttctaca taaagtctcc agatgattat 12240
aagtataatc acctagatgg gccatctgta atgctcatca ctgacagacc tagtgaagat 12300
ttggatggga ggctcgttca ccaaagtgac atttttacta ctacaagtcc tataaaacag 12360
gtccggtatg aagagcatca gtcacataca aagcagtatc ctgtaaacaa aatacaagct 12420
ataatttttt tgatagggtt aggctcgttc attggaagca tattcgtagt tttggtagta 12480
tggattatac gcagatattg caatggagcg cggagtgggg gaacgccccc cagtcctcgc 12540
cggtatgtgt ataccaggct atgatcacgt gtgaaacttg ggcggacctg tatcatatgt 12600
acaccgtccc tattcgttta tagccagtac gtgttatctg cacatagagg aacatgtgtc 12660
atactgggat cgcatgcatg gtatgtgtga ctctaatatt attctgtatc ataataaaaa 12720
cacagtgcat ggtatataga ggatcgctgg taagcactac ggtagaccaa tcggctcaga 12780
ttgcattctt tggcatcgat accgttgtta atttatatgg caaagtcttg ttcatgggag 12840
atcagtattt ggaggaaata tactctggaa cgatggaaat actcaaatgg aatcaagcta 12900
accgctgcta ttctattgcg catgcaacat attacgccga ctgtcctata atcagttcta 12960
cggtattcag aggatgccgg gacgccgttg tttatactag gccccacagc agaattc 13017

<210> SEQ ID NO 18
<211> LENGTH: 15252
<212> TYPE: DNA
<213> ORGANISM: Artificial Sequence
<220> FEATURE:
<223> OTHER INFORMATION: Herpesvirus of turkeys, murine cytomegalovirus, Infectious bursal disease virus, Simian vacuolating virus 40, and Infectious laryngotracheitis virus

<400> SEQUENCE: 18
ggcgcgccac tggagaacgg catgaccgca aaaggcgttg tagagatcga tcccacgaac 60
tctcaggcga tcgtgtcagt cgccataaac agcgacgatc gtctccagga tctgaacggt 120
tttcttctca acgatcatca gtatatgagg aactgaacct gatatttagc cgagggaaac 180
gcaggttaaa aaccctatca agcgattgcg attttcgcgt atctagtaaa aatagatggg 240
cttcggtact agccttcgcc gccaactctg aatatgccct tcgtggacct catataacat 300
ggcattgttt gttggatgcg gggccggaat taagaagaac attcgaaata cgagcaaaaa 360
tttcggccct ggcatgtgct gcgcgagaat cggtacttcg gggagaaagt tttatcggag 420
ctttgggtag tgcagaggaa actctatctt ggttgaaaat gcatgcgacc ctgcacttga 480
ttctggttaa ccacgatcca atttttaaga cggctggcgc ggtcctagat aacctccgct 540
taaaactagc cccaatattg atgtgcagat ataacacaga aaaacgatca atggaagaca 600
tgctacggcg gtcatctccc gaagacatca ccgattccct aacaatgtgc ctgattatgt 660
tatcgcgcat tcgtcgtacc atgcgcaccg caggaaataa atatagctat atgatagatc 720
caatgaatcg tatgtctaat tacactccag gcgaatgtat gacaggtata ttgcgatata 780
ttgacgaaca tgctagaagg tgtcctgatc acatatgtaa tttgtatatc acatgtacac 840
ttatgccgat gtatgtgcac gggcgatatt tctattgtaa ttcatttttt tgttagtaaa 900
ctaccacagg ctgtccggaa atctaagtta atgaataaag tagatggtta atactcattg 960
cttagaattg gactactttt aattctcttt aatgttcgta ttaaataaaa acatctttaa 1020
taaacttcag cctcttcgct tattgtagaa attgagtatt caaaatcatg ttcaaagccg 1080
tcttcggaga gtgtactcgc cacggtggtt ggaacatcac tatgtctaca cgtcaaattt 1140
aagcacgtca ggtctgtcga ggacaagaaa tggttaacta gtgtttcaat tattcttata 1200
aacgttaagc attgtaagcc ccccggccgt ccgcagcaac aatttactag tatgccgtgg 1260
gctccgggac tatcacggat gtccaattcg cacatgcata taatttttct agggtctctc 1320
atttcgagaa atcttcgggg atccatcagc aatgcgggct gtagtcccga ttcccgtttc 1380
aaatgaaggt gctccaacac ggtcttcaaa gcaaccggca taccagcaaa cacagactgc 1440
aactccccgc tgcaatgatt ggttataaac agtaatctgt cttctggaag tatatttcgc 1500
ccgacaatcc acggcgcccc caaagttaaa aaccatccat gtgtatttgc gtcttctctg 1560
ttaaaagaat attgactggc attttcccgt tgaccgccag atatccaaag tacagcacga 1620
tgttgcacgg acgactttgc agtcaccagc cttcctttcc acccccccac caacaaaatg 1680
tttatcgtag gacccatatc cgtaataagg atgggtctgg cagcaacccc ataggcgcct 1740
cggcgtggta gttctcgagg ccttaagctt aaggatcccc caactccgcc cgttttatga 1800
ctagaaccaa tagtttttaa tgccaaatgc actgaaatcc cctaatttgc aaagccaaac 1860
gcccccctatg tgagtaatac ggggactttt tacccaattt cccacgcgga aagcccccta 1920
atacactcat atggcatatg aatcagcacg gtcatgcact ctaatggcgg cccataggga 1980
ctttccacat agggggcgtt caccatttcc cagcataggg gtggtgactc aatggccttt 2040
acccaagtac attgggtcaa tgggaggtaa gccaatgggt ttttcccatt actggcaagc 2100
acactgagtc aaatgggact ttccactggg ttttgcccaa gtacattggg tcaatgggag 2160
gtgagccaat gggaaaaacc cattgctgcc aagtacactg actcaatagg gactttccaa 2220
tgggtttttc cattgttggc aagcatataa ggtcaatgtg ggtgagtcaa tagggacttt 2280
ccattgtatt ctgcccagta cataaggtca atagggggtg aatcaacagg aaagtcccat 2340
tggagccaag tacactgcgt caatagggac tttccattgg gttttgccca gtacataagg 2400
tcaatagggg atgagtcaat gggaaaaacc cattggagcc aagtacactg actcaatagg 2460
gactttccat tgggttttgc ccagtacata aggtcaatag ggggtgagtc aacaggaaag 2520
ttccattgga gccaagtaca ttgagtcaat agggactttc caatgggttt tgcccagtac 2580
ataaggtcaa tgggaggtaa gccaatgggt ttttcccatt actggcacgt atactgagtc 2640
attagggact ttccaatggg ttttgcccag tacataaggt caataggggt gaatcaacag 2700
gaaagtccca ttggagccaa gtacactgag tcaataggga ctttccattg ggttttgccc 2760
agtacaaaag gtcaataggg ggtgagtcaa tgggtttttc ccattattgg cacgtacata 2820
aggtcaatag ggtgagtca ttgggttttt ccagccaatt taattaaaac gccatgtact 2880
ttcccaccat tgacgtcaat gggctattga aactaatgca acgtgacctt taaacggtac 2940
tttcccatag ctgattaatg ggaaagtacc gttctcgagc caatacacgt caatgggaag 3000
tgaaagggca gccaaaacgt aacaccgccc cggttttccc ctggaaattc catattggca 3060

-continued

```
cgcattctat tggctgagct gcgttctacg tgggtataag aggcgcgacc agcgtcggta   3120
ccgtcgcagt cttcggtctg accaccgtag aacgcagagc tcctcgctgc aggcggccgc   3180
tctagaactc gtcgatcgca gcgatgacaa acctgcaaga tcaaacccaa cagattgttc   3240
cgttcatacg gagccttctg atgccaacaa ccggaccggc gtccattccg gacgacaccc   3300
tggagaagca cactctcagg tcagagacct cgacctacaa tttgactgtg ggggacacag   3360
ggtcagggct aattgtcttt ttccctggat tccctggctc aattgtgggt gctcactaca   3420
cactgcagag caatgggaac tacaagttcg atcagatgct cctgactgcc cagaacctac   3480
cggccagcta caactactgc agactagtga gtcggagtct cacagtgagg tcaagcacac   3540
tccctggtgg cgtttatgca ctaaacggca ccataaacgc cgtgaccttc caaggaagcc   3600
tgagtgaact gacagatgtt agctacaatg ggttgatgtc tgcaacagcc aacatcaacg   3660
acaaaattgg gaatgtcctg gtaggggaag ggtcactgt cctcagccta cccacatcat    3720
atgatcttgg gtatgtgagg cttggtgacc ccattcccgc tatagggctt gacccaaaaa   3780
tggtagctac atgcgacagc agtgacaggc ccagagtcta caccataact gcagccgatg   3840
attaccaatt ctcatcacag taccaaccag gtggggtaac aatcacactg ttctcagcca   3900
acattgatgc tatcacaagc ctcagcattg gggagagct cgtgtttcaa acaagcgtcc    3960
aaggccttgt actgggcgcc accatctacc ttataggctt tgatgggact gcggtaatca   4020
ccagagctgt ggccgcagat aatgggctga cggccggcac cgacaatctt atgccattca   4080
atcttgtcat tccaaccaat gagataaccc agccaatcac atccatcaaa ctggagatag   4140
tgacctccaa aagtggtggt caggcagggg atcagatgtc atggtcggca agtgggagcc   4200
tagcagtgac gatccatggt ggcaactatc caggggccct ccgtcccgtc acactagtag   4260
cctacgaaag agtggcaaca ggatccgtcg ttacggtcgc tggggtgagt aacttcgagc   4320
tgattccaaa tcctgaacta gcaaagaacc tggttacaga atacggccga tttgacccag   4380
gagccatgaa ctacacaaaa ttgatactga gtgagaggga ccgtcttggc atcaagaccg   4440
tctggccaac aagggagtac actgattttc gtgagtactt catggaggtg gccgacctca   4500
actctcccct gaagattgca ggagcatttg gcttcaaaga cataatccgg gctataagga   4560
ggtagatcca gacatgataa gatacattga tgagtttgga caaaccacaa ctagaatgca   4620
gtgaaaaaaa tgctttattt gtgaaatttg tgatgctatt gctttatttg taaccattat   4680
aagctgcaat aaacaagtta acaacaacaa ttgcattcat tttatgtttc aggttcaggg   4740
ggaggtgtgg gaggtttttt cggatcctct agagtcgacg gcagagtcgc agacgcccct   4800
attggacgtc aaaattgtag aggtgaagtt ttcaaacgat ggcgaagtaa cggcgacttg   4860
cgtttccacc gtcaaatctc cctatagggt agaaactaat tggaaagtag acctcgtaga   4920
tgtaatggat gaaatttctg ggaacagtcc cgccggggtt tttaacagta atgagaaatg   4980
gcagaaacag ctgtactaca gagtaaccga tggaagaaca tcggtccagc taatgtgcct   5040
gtcgtgcacg agccattctc cggaacctta ctgtcttttc gacacgtctc ttatagcgag   5100
ggaaaaagat atcgcgccag agttatactt tacctctgat ccgcaaacgg catactgcac   5160
aataactctg ccgtccggcg ttgttccgag attcgaatgg agccttaata atgtttcact   5220
gccggaatat ttgacggcca cgaccgttgt ttcgcatacc gctggccaaa gtacagtgtg   5280
gaagagcagc gcgagagcag gcgaggcgtg gatttctggc cggggaggca atatatacga   5340
atgcaccgtc ctcatctcag acggcactcg cgttactacg cgaaaggaga ggtgcttaac   5400
aaacacatgg attgcggtgg aaaacggtgc tgctcaggcg cagctgtatt cactcttttc   5460
```

-continued tggacttgtg tcaggattat gcgggagcat atctgctttg tacgcaacgc tatggaccgc 5520
catttatttt tgaggaatgc tttttggact atcgtactgc tttcttcctt cgctagccag 5580
agcaccgccg ccgtcacgta cgactacatt ttaggccgtc gcgcgctcga cgcgctaacc 5640
ataccggcgg ttggcccgta taacagatac ctcactaggg tatcaagagg ctgcgacgtt 5700
gtcgagctca acccgatttc taacgtggac gacatgatat cggcggccaa agaaaaagag 5760
aaggggggcc ctttcgaggc ctccgtcgtc tggttctacg tgattaaggg cgacgacggc 5820
gaggacaagt actgtccaat ctatagaaaa gagtacaggg aatgtggcga cgtacaactg 5880
ctatctgaat gcgccgttca atctgcacag atgtgggcag tggactatgt tcctagcacc 5940
cttgtatcgc gaaatggcgc gggactgact atattctccc ccactgctgc gctctctggc 6000
caatacttgc tgaccctgaa aatcgggaga tttgcgcaaa cagctctcgt aactctagaa 6060
gttaacgatc gctgtttaaa gatcgggtcg cagcttaact ttttaccgtc gaaatgctgg 6120
acaacagaac agtatcagac tggatttcaa ggcgaacacc tttatccgat cgcagacacc 6180
aatacacgac acgcggacga cgtatatcgg ggatacgaag atattctgca gcgctggaat 6240
aatttgctga ggaaaaagaa tcctagcgcg ccagaccctc gtccagatag cgtcccgcaa 6300
gaaattcccg ctgtaaccaa gaaagcggaa gggcgcaccc cggacgcaga aagcagcgaa 6360
aagaaggccc ctccagaaga ctcggaggac gacatgcagg cagaggcttc tggagaaaat 6420
cctgccgccc tccccgaaga cgacgaagtc cccgaggaca ccgagcacga tgatccaaac 6480
tcggatcctg actattacaa tgacatgccc gccgtgatcc cggtggagga gactactaaa 6540
agttctaatg ccgtctccat gcccatattc gcggcgttcg tagcctgcgc ggtcgcgctc 6600
gtggggctac tggtttggag catcgtaaaa tgcgcgcgta gctaatcgag cctagaatag 6660
gtggtttctt cctacatgcc acgcctcacg ctcataatat aaatcacatg gaatagcata 6720
ccaatgccta ttcattggga cgttcgaaaa gcatggcatc gctacttgga actctggctc 6780
tccttgccgc gacgctcgca cccttcggcg cgatgggaat cgtgatcact ggaaatcacg 6840
tctccgccag gattgacgac gatcacatcg tgatcgtcgc gcctcgcccc gaagctacaa 6900
ttcaactgca gctatttttc atgcctggcc agagacccca caaaccctac tcaggaaccg 6960
tccgcgtcgc gtttcggtct gatataacaa accagtgcta ccaggaactt agcgaggagc 7020
gctttgaaaa ttgcactcat cgatcgtctt ctgtttttgt cggctgtaaa gtgaccgagt 7080
acacgttctc cgcctcgaac agactaaccg gacctccaca cccgtttaag ctcactatac 7140
gaaatcctcg tccgaacgac agcgggatgt tctacgtaat tgttcggcta gacgacacca 7200
aagaacccat tgacgtcttc gcgatccaac tatcggtgta tcaattcgcg aacaccgccg 7260
cgactcgcgg actctattcc aaggcttcgt gtcgcacctt cggattacct accgtccaac 7320
ttgaggccta tctcaggacc gaggaaagtt ggcgcaactg gcaagcgtac gttgccacgg 7380
aggccacgac gaccagcgcc gaggcgacaa ccccgacgcc cgtcactgca accagcgcct 7440
ccgaacttga agcggaacac tttacctttc cctggctaga aaatggcgtg gatcattacg 7500
aaccgacacc cgcaaacgaa aattcaaacg ttactgtccg tctcgggaca atgagcccta 7560
cgctaattgg ggtaaccgtg gctgccgtcg tgagcgcaac gatcggcctc gtcattgtaa 7620
tttccatcgt caccagaaac atgtgcaccc cgcaccgaaa attagacacg gtctcgcaag 7680
acgacgaaga acgttcccaa actagaaggg aatcgcgaaa atttggaccc atggttgcgt 7740
gcgaaataaa caagggggct gaccaggata gtgaacttgt ggaactggtt gcgattgtta 7800

-continued

```
acccgtctgc gctaagctcg cccgactcaa taaaaatgtg attaagtctg aatgtggctc   7860
tccaatcatt tcgattctct aatctcccaa tcctctcaaa aggggcagta tcggacacgg   7920
actgggaggg gcgtacacga tagttatatg gtacagcaga ggcctctgaa cacttaggag   7980
gagaattcag ccggggagag cccctgttga gtaggcttgg gagcatattg caggatgaac   8040
atgttagtga tagttctcgc ctcttgtctt gcgcgcctaa cttttgcgac gcgacacgtc   8100
ctctttttgg aaggcactca ggctgtcctc ggggaagatg atcccagaaa cgttccggaa   8160
gggactgtaa tcaaatggac aaaagtcctg cggaacgcgt gcaagatgaa ggcggccgat   8220
gtctgctctt cgcctaacta ttgctttcat gatttaattt acgacggagg aaagaaagac   8280
tgcccgcccg cgggacccct gtctgcaaac ctggtaattt tactaaagcg cggcgaaagc   8340
ttcccgggtt aattaaggcc ctcgaggata catccaaaga ggttgagtat tctctctaca   8400
cttcttgtta aatggaaagt gcatttgctt gttcttacaa tcggcccgag tctcgttcac   8460
agcgcctcgt tcacacttaa accacaaata gtctacaggc tatatgggag ccagactgaa   8520
actcacatat gactaatatt cgggggtgtt agtcacgtgt agcccattgt gtgcatataa   8580
cgatgttgga cgcgtcctta ttcgcggtgt acttgatact atggcagcga gcatgggata   8640
ttcatcctcg tcatcgttaa catctctacg ggttcagaat gtttggcatg tcgtcgatcc   8700
tttgcccatc gttgcaaatt acaagtccga tcgccatgac cgcgataagc ctgtaccatg   8760
tggcattagg gtgacatctc gatcatacat tataagacca acgtgcgagt cttccaaaga   8820
cctgcacgcc ttcttcttcg gattgtcaac gggttcttca gaatctatgc ccatatctgg   8880
cgttgagacc attgtgcgtt taatgaacaa taaagcggca tgccatggaa aggagggctg   8940
cagatctcca ttttctcacg ccactatcct ggacgctgta gacgataatt ataccatgaa   9000
tatagagggg gtatgtttcc actgccactg tgatgataag ttttctccag attgttggat   9060
atctgcattt tctgctgccg aacaaacttc atcgctatgc aaagagatgc gtgtgtacac   9120
gcgccggtgg agtatacggg aaactaaatg ttcatagagg tctttgggct atatgttatt   9180
aaataaaata attgaccagt gaacaatttg tttaatgtta gtttattcaa tgcattggtt   9240
gcaaatattc attacttctc caatcccagg tcattcttta gcgagatgat gttatgacat   9300
tgctgtgaaa attactacag gatatatttt taagatgcag gagtaacaat gtgcatagta   9360
ggcgtagtta tcgcagacgt gcaacgcttc gcatttgagt taccgaagtg cccaacagtg   9420
ctgcggttat ggtttatgcg cacagaatcc atgcatgtcc taattgaacc atccgatttt   9480
tcttttaatc gcgatcgatg tttgggcaac tgcgttattt cagatctaaa aaatttaccc   9540
tttatgacca tcacatctct ctggctcata ccccgcttgg ataagatatc atgtagattc   9600
cgccctaaga aatgcaaact aacattattg tcggttccat atacacttcc atcttgtcct   9660
tcgaaaataa caaactcgcg caatagaccg tccgtacatg catggccgat gtgtgtcaac   9720
atcattggtc tgctagatcc cgatgggacg aatcgtacag tcgtcgctcc agcattggca   9780
aaaatcccca gataccctcc atgcggcaaa tctaaattgc gaccccgaag agactgcacc   9840
aaagtcttat cgacgcacgc tgattttttt gaacagcggg agcccattat cttcagtgga   9900
gcgtagacgg gcgaggctaa ttatgtgaca tagcaacact gcatgtatgt ttttataaat   9960
caataagagt acataattta ttacgtatca tttccgtttg taatatactg tatacatcat  10020
ccacactatt agtcagcact agcgcgcggg cgcacgttac aatagcagcg tgcccgttat  10080
ctatattgtc cgatatttac acataacatt tcatcgacat gattaaatac ctaagtactg  10140
cacacagatg tttaatgtat atcgtcatat aaattatatc gctaggacag acccaaacga  10200
```

cctttatccc aaacagtcag atcctcttct caagtgtcga tttctgttat ggaatatgca 10260
taccctggcc cagaaattgc acgcacgagc gtagtgaatg cgtcattggt tttacattta 10320
aaggctaaat gcacaaattc tttagacgac agcacatcgt taaatagcat ctctagcgtt 10380
cttatgaatg ctaagcattg gagtcctcct ggtcggccac aataacagct gagtatcata 10440
ccctgagctc cggggttgtc gcacatagcg gattcgtata aacataggat tttccgcgaa 10500
tccatcagtt gcaaaaatct gttaggctcc atcaacaacg ctggatttac ttcagatcca 10560
cgcgtaaagt aatggtgctc gaataccgtt tttagagttg tcggcatttc aaggaacaaa 10620
gaattcattt cttcattgca acgacgcgcc agaaatccca agacctcttt gggtagtatg 10680
ttcttgccta taaaacacgg cgttccaagt gccaggaacc acgcatgtgt tactgttggg 10740
gcgtattcag aaataaagcg gggtttatgc ggcttttgaa gctcggatat ccaaagtatc 10800
gcttgctgat gaacgagcga tgtagctgtt acaaaacctc ctttccatcc tccagtcaac 10860
ataatattta tcggcctacc tatgtccgta ataagtattg gtcgggcaat tattccgtat 10920
gaggtcttgc aggaataagc tcttagggac agccagcttg gatatggtgc gaaacagacc 10980
ttctcggctt cagaatgtcg ctccgcagtc tcttcgtgtc ggtgcatctt agatccacca 11040
tcaatgtgtg cagcattgac tcccgcccgt cgaatattcc ttttgttacg atgcagtaat 11100
gagcacgatc atgggcgggg cgatgacgtt ctatttgcat gtctgcgaac aatttgcgtc 11160
agtcatacag ctatggagtg ggccatttct ggccgtcaac ttaaaaacgc gaaccgcaga 11220
catatgtatt tgcatgcaaa gacgtatctt cgtatttctg ggcatcttca aatgctctgg 11280
ccaatatggc aatgaatttg gattcgtttg acgccgatgg tatgcagtgc aaatgtgcca 11340
atagcccaca tccgaaaaag ttatttgtca tacaagcagg tgttaagtag caatcacata 11400
aaggcaccag acgcctcatg gcatcataat gaatagctcc ttctccccac tggaaccact 11460
gacaaaatct gcgagtatat tccgcaaacc acattttatt tctcatagaa actaccctaa 11520
atccttttaa cgggaagaag aatcctagat agtgcttgaa gtcatgactg ttactgctgc 11580
aataacactg tatattattt ataaattccg tttgtctagg tatctgatgt aggcattccg 11640
atccctttac tattgcgtct tcacgaccaa atgggaatgc gccaaaatcc ccacacctca 11700
tcaccctgga ggcagattgt gtattattaa tatccgccga ttgaagcaca aaacggtacg 11760
gtactgttcc taattctggt atagattcta tggtcaaaag tctgcatatc cccgacattg 11820
ccatgagatc acacagtcca agtagcatgt ttattgagtc actcagactg tcaacgtccc 11880
tcgccgcacc accaatcgaa aataaagtat ctacgcaagt tatagctccg cattttctat 11940
cgctagcagc aatcgcgacg caaaacataa aggccatgtt gggatttgaa ctctctgggg 12000
ggcttgttat cttctgcacc gtcgcagtcg cagttttccg aaatttatgt ctaatatatt 12060
ttccggccgt gctccaatcg gccgaaaaga atctgcgtat taccagactc attgacgggc 12120
cgataaagac cataaaacaa aattcctgtg cactccctcc tccagttttg ccatcgtcca 12180
agtcccgtaa cttttttttgc gtttcgagga gcaagcgttc gttatcccta cccacacttg 12240
ttttccaccg ttttcttatt ataagcggtt gtatcgccaa cgcgtcaccg caggttgtca 12300
catacagtga tggcatactt gaacgtgcaa caacgcgctc gctttgcaaa tctaagtcat 12360
tgaccatcaa atcgcgttga gaggatagcc aggcatcttt tttcctagta tggtgacggt 12420
gcagccaccc caactcagtt cttgtaaaaa aagctattgg cgggaattta tgttctgagg 12480
tgcattctat atttatgagt ccatcaaatg ccattaacca gattcgtatt ttttcgctcg 12540

```
acccggcatc actatggata caataccttt ctatggccca tttcagctct cgaaccaacc  12600
acacggacaa ttgactaaca taagtatgat ctttatcaca gtcgcaccca tctgagttat  12660
atttatggca tccgagcgct cttactgtac ggtcggatac acccatggtt tttcctttat  12720
atagtcgggt tatagtctgt cgggtttggc ggtagcacgg agtagtttga tttttaagaa  12780
tcgaaaaccg gcttggagag accactgtcg aatatttgtc cgtatactct acacgtgagt  12840
gttgtccatt cctaggtata ttcatctgtt cggatacctt caattgctgt tcaggcataa  12900
ccttaaagca tatgttatgt tgtacatcaa aacttggtga gttatgttcg attgccgcgc  12960
ataaagaatc gtacatgagc gtttctgcta acatactatc tatattctca cacgcccctg  13020
catatactgt tcctattcca aattcacgtt ttgccccatc ggctatctgc tcccaaaaag  13080
ttgtaatata ggtgccgctg ggtgcgaaat tttcatcagt tgtattcctg ataaactgaa  13140
tcactttaca taatttttgc cacatatctg cgtgcagcca tagtatcgaa cccgtgggct  13200
cggagacgac agtgcgtaca atgggtattt tacctttccc caacaaaata atggtataca  13260
agttaggtcc gtacctagac cttaatgttt ccaattcttc tgaatcactg cactctcgta  13320
ggggagtaac ggtaataatt tcgtctctga gccccgtttt gcgttgaaaa ctaatcacat  13380
tagataatgt gcaatcggtt tcttttatcc ggatacatct aagtattatg acatcggtgg  13440
tcattgtttc catcaacgac catcttttac gatcgcccat actactcatg gacgttgtcg  13500
gtgttgaaaa atcaccagaa ttgcaacgga tctctgggta ccatgctgct gatggaattg  13560
gcggttttaa ttgttgtttc agtctattat tgctatcttt ggcggggttg aataatgtgg  13620
ggggagagtg attgcaggaa tccgaatggg tcaataaaac gaccgtgctc cgttctgccg  13680
gcgccgatcc gattgaagct atatacttcg cttctctccc cacttttcca atttgatccg  13740
gaaataaaac ggccccggac aacagtatcg tacgatccgg atccggatcc tgcttgccta  13800
cagaagaatc aacatctcgc cccaatattc tggtcaaaac tggctcgctc atggcaacgc  13860
ggacgtttcc cccggtggcc agtcttaatg gttaatgttc ttttcggcaa tcttatacat  13920
cagcgggttg cgtgaatact ggtcacagtt cagtcattta ctacacacca gcaatacgac  13980
gacggacagt accgtcccga cgaacgcgac gcccaaaatt gctatcgcga ccgcgtccga  14040
ggcgatgtcg tacgggcggt gcggggttgg atcctcggca aagagatcct cgtaattcgg  14100
cggtgggagc ggagggtaaa gacgcgggtg gggatctccc tccggaccgc gcgccgggcg  14160
cggttcgaaa atgctttccg cctcgctcag tgtcaacgcc aagtattcgg gcgggctggg  14220
ggccggaata tctcccgcga cttcttctat cggcgcggaa ttggagtcgc ggtcgtggcg  14280
cgcttctagc gtcgtcaacg gaagtccatt ttcggggtct cccggtgggc gttcagcgtc  14340
catcgtcgta tatgctctaa cacacgtctc gctatattaa aaaaaagaag agtatcggtc  14400
agtgtcgagt gtcgccgaca atgtcgcgag ttctcggcga tttaattttt ggaactgctc  14460
cctatgaatc ccgtaactgt agcgcccgcg cagaaagccg ccatcagacc aactacgtgt  14520
ctgttcgatg tttgcccgcc gatcgcttta ccgattaagg ttccggcgag aaatgacatg  14580
ctcgatccaa gaacaaagtt tttcgcggta aacaacaaca tagttaccgt gcgagatgga  14640
gaaaccacat ctcccgaatt agtagaggaa agcccgcgct gtcggtttgg ggacatatcg  14700
atctttttg tgtttttcct aggacccttt tgccagatcg tacaaagtcg cgtcttatga  14760
gcggacgttc ttactgcagc tcggtaggag tggggcaggg ttagatttcg tcggcgtttc  14820
ggcccccgta tgcgccgcgc caccctcttc gccgagctct ttatgcgcgg tgggggtgag  14880
cgcttccgga gttgcgatct ccgatctcga gccgcagccc ggcggtgtct ctttcagtgg  14940
```

-continued

```
agcgttagcg ccatcatgtg gttcgtggcg gtggaaaggc tattatgtgt taggggagag    15000

accacgtgat cggcatgcaa atgagcaagg cgaacgcgtc agcgttcgca ctgcgaacca    15060

ataatatata tattatacta ttggctttag gtgcgaacgt ccggctagtc caatagcggg    15120

gtcgcgtttc gtaccacgtg ttatagaccg ccctaaactc gcactcgggg gtccggccgc    15180

gcccagacag ggcggagacg tgccacaggg gctttaaaac accgcttcgg gcaccgttca    15240

tctcggcgcg cc                                                        15252

<210> SEQ ID NO 19
<211> LENGTH: 199
<212> TYPE: DNA
<213> ORGANISM: Simian virus 40

<400> SEQUENCE: 19

agcttcagac atgataagat acattgatga gtttggacaa accacaacta gaatgcagtg       60

aaaaaaatgc tttatttgtg aaatttgtga tgctattgct ttatttgtaa ccattataag      120

ctgcaataaa caagttaaca acaacaattg cattcatttt atgtttcagg ttcaggggga     180

ggtgtgggag gttttttcg                                                  199
```

RECOMBINANT NON-PATHOGENIC MAREK'S DISEASE VIRUS CONSTRUCTS ENCODING INFECTIOUS LARYNGOTRACHEITIS VIRUS AND INFECTIOUS BURSAL DISEASE VIRUS ANTIGENS

CROSS-REFERENCE TO RELATED APPLICATIONS

This application is a national stage entry under 35 U.S.C. § 371 of PCT/EP2017/064662, filed on Jun. 15, 2017, which claims priority to U.S. Application No. 62/351,471, filed on Jun. 17, 2016, the content of PCT/EP2017/064662 is hereby incorporated by reference in its entirety.

FIELD OF THE INVENTION

The present invention relates to novel recombinant multivalent non-pathogenic Marek's Disease virus constructs encoding and expressing Infectious Laryngotracheitis Virus and Infectious Bursal Disease Virus protein antigens, and methods of their use in poultry vaccines.

BACKGROUND OF THE INVENTION

Pathogenic poultry viruses are not only debilitating to chickens, but they also are costly to chicken breeders because most of the resulting diseases are contagious and the poultry industry relies heavily on confined, large-scale breeding facilities. Vaccinating young chicks is often the only viable means to combat these viruses. Although attenuated or killed poultry viral vaccines remain important in the market place, in recent years significant resources have been expended on developing vaccines containing recombinant viral constructs which express pathogenic viral protein antigens. Furthermore, substantial efforts have been made to construct stable and efficacious multivalent recombinant non-pathogenic Marek's Disease virus (abbreviated as $rMDV_{np}$) vectors that express foreign genes from multiple viral pathogens. Such multivalent vaccines would serve to minimize the number of injections given to the chicks and thereby, reduce discomfort and stress on the vaccinated chick, as well as significantly reduce costs in labor and materials. Vaccinating with such single multivalent constructs also would be preferable to alternative multivalent $rMDV_{np}$ vaccines that contain multiple recombinant monovalent $rMDV_{np}$ constructs, because these alternative vaccines have, at least to date, resulted in protection against only a single viral pathogen. The failure of such alternative vaccines is presumably due to one of the monovalent $rMDV_{np}$ constructs overgrowing the other monovalent $rMDV_{np}$ constructs thereby, preventing these other monovalent $rMDV_{np}$ constructs from inducing a significant immune response. In any case, despite substantial efforts in the past to construct stable and efficacious multivalent $rMDV_{np}$ vectors that express foreign genes from multiple viral pathogens indeed, such vaccines had been suggested more than twenty years ago [see e.g., U.S. Pat. No. 5,965,138], it has been only recently that a multivalent vaccine that comprises a recombinant herpesvirus of turkeys (abbreviated as rHVT) encoding antigens from more than one other pathogen has been shown to be both stable and efficacious.

One poultry virus disease that can be controlled through vaccination is Marek's disease. Marek's disease is a pathogenic disease that adversely affects chickens worldwide. Marek's disease occurs predominantly in young chickens between 2 and 5 months of age. Clinical signs include: progressive paralysis of one or more of the extremities, incoordination due to paralysis of legs, drooping of the limb due to wing involvement, and a lowered head position due to involvement of the neck muscles. In acute cases, severe depression may result. Bursal and thymic atrophy may also develop.

The etiological agent for Marek's disease is Marek's disease virus serotype 1 (abbreviated as MDV1), a cell-associated virus having a double-standed DNA genome. MDV1 is a lymphotropic avian alphaherpesvirus that both: (i) infects B cells, which can result in cytolysis, and (ii) latently infects T cells, which can induce T-cell lymphoma. Closely related to the virulent MDV1 strain, Marek's disease virus serotype 2 (abbreviated as MDV2), previously known as Gallid herpes virus 3, is a naturally attenuated MDV strain that has been shown to have little to no pathogenicity in chickens [Petherbridge et al., *J. Virological Methods* 158:11-17 (2009)]. SB-1 is a specific MDV2 strain that has been shown to be useful in vaccines against MDV1 [see e.g., Murthy and Calnek, Infection and Immunity 26(2) 547-553 (1979)].

Another closely related alphaherpesvirus, Marek's disease virus serotype 3 (abbreviated as MDV3), more widely known as herpesvirus of turkeys (abbreviated as HVT), is a nonpathogenic virus of domestic turkeys [see e.g., Kingham et al., *J. of General Virology* 82:1123-1135 (2001)]. Two commonly used strains of HVT are the PB1 strain and the FC126 strain. Whereas, HVT is also nonpathogenic in chickens, it does induce a long-lasting protective immune response in chickens against MDV1. Accordingly, HVT has been used in poultry vaccines against virulent MDV1 for many years, generally in combination with SB-1, which is more viraemic than HVT, but considered less safe. Alternatively, when flocks are challenged with particularly virulent MDV1 strains, HVT can be combined with the Rispen's vaccine. The Rispen's vaccine is an isolate that originated from a mildly virulent MDV1 strain that was subsequently further weakened by cell passaging. The Rispen's strain however, retains some virulence towards highly susceptible lines of chickens.

The sequence of the complete genome of HVT has been disclosed [Afonso et al., *J. Virology* 75(2):971-978 (2001)], and as most alphaherpesviruses, HVT possesses a significant number of potential nonessential insertion sites [see e.g., U.S. Pat. Nos. 5,187,087; 5,830,745; 5,834,305; 5,853,733; 5,928,648; 5,961,982; 6,121,043; 6,299,882 B1]. HVT also has been shown to be amenable to genetic modification and thus, has been used as a recombinant vector for many years [WO 87/04463]. Accordingly, recombinant HVT vectors have been reported to express foreign genes that encode antigens from e.g., Newcastle Disease Virus (NDV), [Sondermeijer et al., *Vaccine,* 11:349-358 (1993); Reddy et al., *Vaccine,* 14:469-477 (1996)], Infectious Bursal Disease Virus (IBDV), [Darteil et al., *Virology,* 211:481-490 (1995); Tsukamoto et al., *J. of Virology* 76(11):5637-5645 (2002)], and Infectious Laryngotracheitis Virus (ILTV) [Johnson et al., *Avian Disease,* 54(4):1251-1259 (2010); WO 92/03554; U.S. Pat. No. 6,875,856]. The entire genomic sequence of MDV2 is also known [see, GenBank acc. nr: AB049735.1, and Petherbridge et al., supra]. The genomic organization of the MDV2 is very similar to that of HVT, with the US region in particular, being identical to that of HVT [see, Kingham et al., supra].

In addition a recombinant chimeric virus, known as the novel avian herpesvirus (NAHV), has been constructed in which specific regions of the HVT genome have been replaced by the corresponding regions of the MDV1 genome. The NAHV also has been used to express foreign genes that encode antigens from other poultry viruses [U.S. Pat. Nos. 5,965,138; 6,913,751].

Like MDV, infectious laryngotracheitis virus (abbreviated as ILTV or ILT) is an alphaherpesvirus that adversely affects chickens, worldwide [Fuchs et al., *Veterinary Research* 38:261-279 (2007)]. ILTV causes acute respiratory disease in chickens, which is characterized by respiratory depression, gasping, and expectoration of bloody exudate. Viral replication is limited to cells of the respiratory tract, where in the trachea the infection gives rise to tissue erosion and hemorrhage.

Infectious bursal disease virus (abbreviated as IBDV or IBD), also called Gumboro disease virus, is the causative agent of infectious bursal disease. IBDV causes an acute, highly-contagious, viral infection of a chicken's lymphoid tissue, with its primary target being the bird's essential immunological organ: the bursa of Fabricius. The morbidity rate in susceptible flocks is high, with rapid weight loss and moderate to high mortality rates. Chicks that recover from the disease may have immune deficiencies because of destruction of (or parts of) the bursa of Fabricius. This makes them particularly vulnerable to secondary infections.

IBDV is a member of the Birnaviridae family. The viruses in this family have a genome consisting of two segments (A and B) of double-stranded RNA. Two serotypes of IBDV exist, serotype 1 and 2, which can be differentiated by virus neutralization (VN) tests. Serotype 1 viruses have been shown to be pathogenic to chickens, while serotype 2 viruses cause only sub-acute disease in turkeys. Historically, IBDV serotype 1 viruses consisted of only one type that is now known as "classic" IBD virus. More recently, so-called "variant" IBDV strains have emerged. Classic and variant strains of IBDV can be identified and distinguished by a virus neutralization test using a panel of monoclonal antibodies, or by RT-PCR [Wu et al., *Avian Diseases,* 51:515-526(2007)]. Well-known classic IBDV strains include, D78, Faragher 52/70, and STC, whereas 89/03 is a well-known variant strain. Many live or inactivated IBDV vaccines are commercially available, e.g. a live vaccine such as NOBI-LIS® Gumboro D78 (MSD Animal Health).

As indicated above, because HVT can act as both an antigen that provides significant protection against Marek's Disease and as a recombinant vector, it is presently used as a platform vector for such multivalent vaccines as Innovax®-ILT (sold by Merck Animal Health), which protects against ILTV; Innovax®-ND-SB (sold by Merck Animal Health) Vectormune® HVT-NDV (sold by Ceva), both of which protect against NDV; and Vaxxitek® HVT+IBD (Merial; previously named: Gallivac™ HVT-IBD), and Vectormune™ HVT-IBD (Ceva) both of which protect against IBDV. Notably, Innovax®-ILT comprises two foreign genes, i.e., ILTV gD and ILTV gI, which has proved to be safe, effective, and stable. However, these two foreign genes are from the same pathogen and moreover, they naturally overlap and need to be co-expressed in order to allow proper immunization against ILTV. More recently, a recombinant safe, effective, and stable multivalent vaccine comprising HVT-ILTV-NDV has been disclosed [U.S. Pat. No. 8,932,604 B2 and U.S. Pat. No. 9,409,954 B2, the contents of which are hereby incorporated by reference in their entireties]. An early HVT-NDV-IBDV also has been disclosed, though upon prolonged testing during the development of the corresponding product one of the main constructs, HVP309, was found neither to display adequate genetic stability nor sustained expression of the heterologous inserts [WO 2013/057,235]. Subsequently, a more stable and efficacious construct was developed [WO 2016/102647].

Therefore, despite the clear advantages of stable, multivalent, recombinant $MDV_{np}$ constructs that can efficaciously express heterologous antigens from two or more different pathogens, and the substantial efforts to design them, heretofore, few have been forthcoming and even one of those few proved to be incapable of achieving all of the requisite requirements. Accordingly, the suitability of any given multivalent recombinant $MDV_{np}$ as a vaccine remains unpredictable when the recombinant $MDV_{np}$ comprises a combination of heterologous antigens that are obtained from a unique set of two or more poultry viruses. Therefore, there is a clear need to overcome the collective industry failures, by constructing novel, stable, recombinant $MDV_{np}$ vectors that can be used in multivalent vaccines as the sole active to protect against two or more different non-MDV1 poultry virus pathogens.

The citation of any reference herein should not be construed as an admission that such reference is available as "prior art" to the instant application.

SUMMARY OF THE INVENTION

Accordingly, the present invention provides a novel, stable, and efficacious multivalent recombinant nonpathogenic Marek's Disease virus ($rMDV_{np}$) for use as a vector to express foreign genes from multiple viral pathogens. In particular embodiments, the $rMDV_{np}$ is a recombinant herpesvirus of turkeys (rHVT). In alternative embodiments, the $rMDV_{np}$ is a recombinant Marek's disease virus serotype 2 (rMDV2). An $rMDV_{np}$, e.g., an rHVT or an rMDV2, can be used in vaccines against pathogenic pouty viruses.

In particular embodiments, an $rMDV_{np}$ comprises a first heterologous nucleic acid located in a first nonessential site in the $rMDV_{np}$ genome and a second heterologous nucleic acid located in a second nonessential site in the $rMDV_{np}$ genome. The first heterologous nucleic acid comprises both a nucleotide sequence that encodes an Infectious Laryngotracheitis Virus (I LTV) gD protein and a nucleotide sequence that encodes an Infectious Laryngotracheitis Virus (I LTV) gI protein. The second heterologous nucleic acid comprises a nucleotide sequence that encodes an Infectious Bursal Disease Virus (IBDV) viral protein 2 (VP2). In specific embodiments of this type, the first heterologous nucleic acid comprises the nucleotide sequence of SEQ ID NO: 9 and the second heterologous nucleic acid comprises the nucleotide sequence of SEQ ID NO: 5. In specific embodiments, the $rMDV_{np}$ is an rHVT. In alternative embodiments, the $rMDV_{np}$ is an rMDV2.

In certain embodiments, the first nonessential site of the $rMDV_{np}$ is the US2 site, while the second nonessential site is a nonessential site of the $rMDV_{np}$ other than the US2 site. In related embodiments, the first nonessential site of the $rMDV_{np}$ is the US2 site and the second nonessential site of the $rMDV_{np}$ is the UL7/8 site. In yet other embodiments, the first nonessential site of the $rMDV_{np}$ is the US2 site and the second nonessential site of the $rMDV_{np}$ is the US10 site. In still other embodiments, the first nonessential site of the $rMDV_{np}$ is the US2 site and the second nonessential site of the $rMDV_{np}$ is the UL 54.5 site. In specific embodiments, the $rMDV_{np}$ is an rHVT. In alternative embodiments, the $rMDV_{np}$ is an rMDV2.

In other embodiments, the second nonessential site of the $rMDV_{np}$ is the US2 site, while the first nonessential site is a nonessential site of the $rMDV_{np}$ other than the US2 site. In related embodiments, the second nonessential site of the $rMDV_{np}$ is the US2 site and the first nonessential site of the $rMDV_{np}$ is the UL7/8 site. In yet other embodiments, the second nonessential site of the $rMDV_{np}$ is the US2 site and the first nonessential site of the $rMDV_{np}$ is the US10 site. In still other embodiments, the second nonessential site of the $rMDV_{np}$ is the US2 site and the first nonessential site of the $rMDV_{np}$ is the UL 54.5 site. In specific embodiments, the $rMDV_{np}$ is an rHVT. In alternative embodiments, the $rMDV_{np}$ is an rMDV2.

In other embodiments, the first nonessential site and the second nonessential site of the $rMDV_{np}$ are the same. In specific embodiments of this type, the first heterologous nucleic acid and the second heterologous nucleic acid are actually constructed as part of the same DNA molecule, which is inserted into a nonessential site of the $rMDV_{np}$. Such a DNA molecule can be an expression cassette that encodes an Infectious Laryngotracheitis Virus (ILTV) gD protein, an Infectious Laryngotracheitis Virus (ILTV) gI protein, and an Infectious bursal disease virus (IBDV) VP2. In particular embodiments of this type, the DNA molecule comprises the nucleotide sequence of SEQ ID NO: 15. In other embodiments of this type, the DNA molecule comprises the nucleotide sequence of SEQ ID NO: 16. In still other embodiments of this type, the DNA molecule comprises the nucleotide sequence of SEQ ID NO: 17. In yet other embodiments of this type, the DNA molecule comprises the nucleotide sequence of SEQ ID NO: 18. In specific embodiments, the $rMDV_{np}$ is an rHVT. In alternative embodiments, the $rMDV_{np}$ is an rMDV2.

Accordingly, in particular embodiments, the first nonessential site and the second nonessential site of the $rMDV_{np}$ are the US2 site. In other embodiments, the first nonessential site and the second nonessential site of the $rMDV_{np}$ are the UL54.5 site. In yet other embodiments, the first nonessential site and the second nonessential site of the $rMDV_{np}$ are the UL7/8 site. In still other embodiments, the first nonessential site and the second nonessential site of the $rMDV_{np}$ are the US10 site. In specific embodiments, the $rMDV_{np}$ is an rHVT. In alternative embodiments, the $rMDV_{np}$ is an rMDV2.

The nucleotide sequences encoding the ILTV gD protein, the ILTV gI protein, and the IBDV VP2 protein can be operatively under the control of exogenous promoters, i.e., promoters that are not naturally found in the $MDV_{np}$. In certain embodiments, these three nucleotide sequences are operatively under the control of different promoters, i.e., the nucleotide sequence encoding the ILTV gD protein is operatively under the control of a first promoter, the nucleotide sequence encoding the ILTV gI protein is operatively under the control of a second promoter, and the nucleotide sequence encoding the IBDV VP2 protein is operatively under the control of a third promoter, with the first promoter, the second promoter, and the third promoter all being different. In particular embodiments, the promoter for the nucleotide sequence encoding the ILTV gD protein is the endogenous ILTV gD promoter. In certain embodiments, the promoter for the nucleotide sequence encoding the ILTV gI protein is the endogenous ILTV gI promoter. In particular embodiments of this type, the promoter for the nucleotide sequence encoding the ILTV gD protein is the endogenous ILTV gD promoter and the promoter for the nucleotide sequence encoding the ILTV gI protein is the endogenous ILTV gI promoter. In specific embodiments, the $rMDV_{np}$ is an rHVT. In alternative embodiments, the $rMDV_{np}$ is an rMDV2.

In certain embodiments, at least one of the promoters operably linked to a nucleotide sequence encoding the ILTV gD protein, the ILTV gI protein, or the IBDV VP2 protein is the murine cytomegalovirus immediate early (mCMV IE) promoter. In related embodiments, at least one of the promoters operably linked to a nucleotide sequence encoding the ILTV gD protein, the ILTV gI protein, or the IBDV VP2 protein is the human cytomegalovirus immediate early (hCMV IE) promoter or a derivative thereof (e.g., from strain AD169). In other embodiments, at least one of the promoters operably linked to a nucleotide sequence encoding the ILTV gD protein, the ILTV gI protein, or the IBDV VP2 protein is the chicken β-actin promoter. In still other embodiments, at least one of the promoters operably linked to a nucleotide sequence encoding the ILTV gD protein, the ILTV gI protein or the IBDV VP2 protein is the pseudorabies virus (PRV) gpX promoter.

In particular embodiments, the promoter for the nucleotide sequence encoding the IBDV VP2 protein is the mCMV IE promoter. In related embodiments, the promoter for the nucleotide sequence encoding the IBDV VP2 protein is the human cytomegalovirus immediate early (hCMV IE) promoter or a derivative thereof (e.g., from strain AD169). In other embodiments, the promoter for the nucleotide sequence encoding the IBDV VP2 protein is the chicken beta-actin gene promoter. In specific embodiments, the promoter for the nucleotide sequence encoding the IBDV VP2 protein is the mCMV IE promoter, the promoter for the nucleotide sequence encoding the ILTV gD protein is the endogenous ILTV gD promoter, and the promoter for the nucleotide sequence encoding the ILTV gI protein is the endogenous ILTV gI promoter. In other specific embodiments, the promoter for the nucleotide sequence encoding the IBDV VP2 protein is the hCMV IE promoter (or a derivative thereof), the promoter for the nucleotide sequence encoding the ILTV gD protein is the endogenous ILTV gD promoter, and the promoter for the nucleotide sequence encoding the ILTV gI protein is the endogenous ILTV gI promoter. In yet other specific embodiments, the promoter for the nucleotide sequence encoding the IBDV VP2 protein is the chicken β-actin promoter, the promoter for the nucleotide sequence encoding the ILTV gD protein is the endogenous ILTV gD promoter, and the promoter for the nucleotide sequence encoding the ILTV gI protein is the endogenous ILTV gI promoter.

In certain embodiments, an $rMDV_{np}$ of the present invention that includes insertions of nucleotide sequences encoding the ILTV gD protein, the ILTV gI protein, and the IBDV VP2 protein also includes one or more exogenous transcription terminator sequences. In specific embodiments of this type, a transcription terminator sequence is downstream from the nucleotide sequence encoding the IBDV VP2 protein. In particular embodiments, the nucleotide sequences encoding the ILTV gD protein and the ILTV gI protein share one transcription terminator sequence and the nucleotide sequence encoding the IBDV VP2 protein has another. In particular embodiments, at least one of the transcription terminator sequences comprises a feline herpesvirus US-9 (FHV US-9) polyadenylation sequence. In related embodiments at least one of the transcription terminator sequences comprises a Herpes Simplex Virus thymidine kinase (HSV TK) polyadenylation sequence. In specific embodiments, the $rMDV_{np}$ is an rHVT. In alternative embodiments, the $rMDV_{np}$ is an rMDV2.

The present invention provides a recombinant nucleic acid comprising in 5' to 3' direction in the following order, (i) a murine cytomegalovirus immediate early (mCMV IE) promoter, (ii) a coding sequence for the IBDV VP2 protein, (iii) a transcription terminator sequence (iv) an ILTV gD promoter, (v) a coding sequence for the ILTV gD protein, (vi) an ILTV gI promoter, and (vii) a coding sequence for the ILTV gI protein. In a particular embodiment of this type, the recombinant nucleic acid comprises the nucleotide sequence of SEQ ID NO: 15. The present invention further provides a recombinant nucleic acid comprising in 5' to 3' direction in the following order, (i) a human cytomegalovirus immediate early (hCMV IE) promoter or derivative thereof, (ii) a coding sequence for the IBDV VP2 protein, (iii) a transcription terminator sequence (iv) an ILTV gD promoter, (v) a coding sequence for the ILTV gD protein, (vi) an ILTV gI promoter, and (vii) a coding sequence for the ILTV gI protein. The present invention also provides a recombinant nucleic acid comprising in 5' to 3' direction in the following order, (i) a chicken β-actin promoter, (ii) a coding sequence for the IBDV VP2 protein, (iii) a transcription terminator sequence (iv) an ILTV gD promoter, (v) a coding sequence for the ILTV gD protein, (vi) an ILTV gI promoter, and (vii) a coding sequence for the ILTV gI protein.

The present invention further provides a recombinant nucleic acid comprising in 5' to 3' direction in the following order, (i) an Infectious Laryngotracheitis Virus (ILTV) gD promoter, (ii) a coding sequence for the ILTV gD protein, (iii) an ILTV gI promoter, (iv) a coding sequence for the ILTV gI protein, (v) a human cytomegalovirus immediate early (hCMV IE), a derivative thereof (e.g., from strain AD169), or an mCMV IE promoter, (vi) a coding sequence for the IBDV VP2 protein, and (vii) a transcription terminator sequence. In a specific embodiment of this type, the recombinant nucleic acid comprises the nucleotide sequence of SEQ ID NO: 17.

The present invention further provides an $rMDV_{np}$ in which a recombinant nucleic acid of the present invention has been inserted into a nonessential insertion site of the $rMDV_{np}$. In certain embodiments of this type, the $rMDV_{np}$ includes an insert in a nonessential site that comprises a recombinant nucleic acid comprising in 5' to 3' direction in the following order (i) a murine cytomegalovirus immediate early (mCMV IE) promoter, (ii) a coding sequence for the IBDV VP2 protein, (iii) a transcription terminator sequence (iv) an ILTV gD promoter, (v) a coding sequence for the ILTV gD protein, (vi) an ILTV gI promoter, and (vii) a coding sequence for the ILTV gI protein. In specific embodiments, intervening nucleotide sequences, such as linkers, spacer sequences, and/or extraneous coding sequences, can also be included, see Example 1 below. In a particular embodiment, the rHVT comprises the nucleotide sequence of SEQ ID NO: 15 inserted into a nonessential site. In particular embodiments of these types, the nonessential site is the US2 site. In other such embodiments, the nonessential site is the UL54.5 site. In still other such embodiments, the nonessential site is the UL7/8 site. In yet other such embodiments, the nonessential site is the US10 site. In specific embodiments, the $rMDV_{np}$ is an rHVT. In alternative embodiments, the $rMDV_{np}$ is an rMDV2.

The present invention also provides methods of making an $rMDV_{np}$ of the present invention. In certain embodiments, a heterologous nucleic acid is constructed that comprises a nucleotide sequence that encodes an ILTV gD protein, a nucleotide sequence that encodes an ILTV gI protein, and a nucleotide sequence that encodes an IBDV VP2 protein. The heterologous nucleic acid is then inserted into a nonessential site of an $rMDV_{np}$ of the present invention. In certain embodiments, the heterologous nucleic acid is an expression cassette. In particular embodiments of this type, the expression cassette comprises the nucleotide sequence of SEQ ID NO: 15. In other embodiments, a first heterologous nucleic acid is constructed that comprises a nucleotide sequence that encodes an ILTV gD protein and a nucleotide sequence that encodes an ILTV gI protein; and a second heterologous nucleic acid is constructed that comprises a nucleotide sequence that encodes an IBDV VP2 protein. The first heterologous nucleic acid is inserted into a US2 site of an $rMDV_{np}$ and the second heterologous nucleic acid is inserted into an alternative nonessential site of the $rMDV_{np}$. In certain embodiments, such heterologous nucleic acids are expression cassettes. In particular embodiments of this type, the first heterologous nucleic acid comprises the nucleotide sequence of SEQ ID NO: 9, and the second heterologous nucleic acid comprises the nucleotide sequence of SEQ ID NO: 5. In other embodiments of this type, the first heterologous nucleic acid comprises the nucleotide sequence of SEQ ID NO: 5, and the second heterologous nucleic acid comprises the nucleotide sequence of SEQ ID NO: 9. In specific embodiments, the method of making an $rMDV_{np}$ is a method of making an rHVT. In alternative embodiments, the method of making an $rMDV_{np}$ is a method of making an rMDV2.

The present invention further provides immunogenic compositions and/or vaccines that comprise any $rMDV_{np}$ of the present invention. In specific embodiments, the $rMDV_{np}$ is an rHVT. In alternative embodiments, the $rMDV_{np}$ is an rMDV2. In addition, the present invention provides methods for aiding in the protection of poultry against a disease caused by ILTV and/or IBDV and/or MDV1 by administering such a vaccine and/or immunogenic composition of the present invention. In specific embodiments, such methods aid in the protection of a chicken. In particular embodiments of this type, a vaccine of the present invention is administered subcutaneously. In other embodiments, a vaccine of the present invention is administered in ovo.

Accordingly in one aspect, the present invention provides immunogenic compositions and/or vaccines that comprise an $rMDV_{np}$ of the present invention. In particular embodiments these immunogenic compositions and/or vaccines are stable, safe, and have relatively strong antigen expression and/or efficacy. Alternatively, or in addition, the immunogenic compositions and/or vaccines that comprise an $rMDV_{np}$ of the present invention aid in the protection of a chicken against a disease caused by ILTV and/or IBDV and/or MDV1, following the administration of the immunogenic compositions and/or vaccines to the chicken.

The present invention also provides immunogenic compositions and/or vaccines that comprise any $rMDV_{np}$ of the present invention that is further combined with an additional IBDV, ILTV, and/or MDV antigen to improve and expand the immunogenicity provided. In addition, the present invention also provides immunogenic compositions and/or vaccines that comprise any $rMDV_{np}$ of the present invention that is further combined with an antigen for a pathogen other than MDV, ILTV, or NDV. In a particular embodiment of this type, the antigen is an attenuated or mild live variant IBDV (e.g., IBDV 89/03). In another particular embodiment of this type, the antigen is an attenuated (or mild live) Newcastle Disease Virus (NDV), e.g., NDV C2. The present invention also provides methods for aiding in the protection of poultry against a disease caused by ILTV and/or IBDV and/or MDV1 and/or NDV by administering such a vaccine and/or immunogenic composition to the poultry (e.g., chicken). In particular embodiments of this type, a vaccine of the present invention is administered subcutaneously. In other embodiments, a vaccine of the present invention is administered in ovo.

In certain embodiments the immunogenic compositions and/or vaccines of the present invention comprise an rHVT that comprises as an insertion into its US2 site of a recombinant nucleic acid comprising 5' to 3': (i) an Infectious Laryngotracheitis Virus (ILTV) gD promoter; (ii) a coding sequence for the ILTV gD protein; (iii) an ILTV gI promoter; (iv) a coding sequence for the ILTV gI protein; (v) a murine cytomegalovirus immediate early (mCMV IE) promoter; (vi) a coding sequence for the Infectious bursal disease virus VP2 protein (IBDV V2); and (vii) a transcription terminator sequence. In even more particular embodiments of this type, the recombinant nucleic acid has the nucleotide sequence of SEQ ID NO: 17. In specific embodiments of this type the immunogenic compositions and/or vaccines further comprise an attenuated (or mild live) variant infectious bursal disease virus (IBDV), e.g., IBDV is 89/03.

The present invention further provides immunogenic compositions and/or vaccines that comprise any $rMDV_{np}$ of the present invention combined with an additional IBDV, ILTV, and/or MDV antigen, and a pathogen other than MDV, ILTV, or IBDV.

These and other aspects of the present invention will be better appreciated by reference to the following Figures and the Detailed Description.

DETAILED DESCRIPTION OF THE INVENTION

Figure 1:
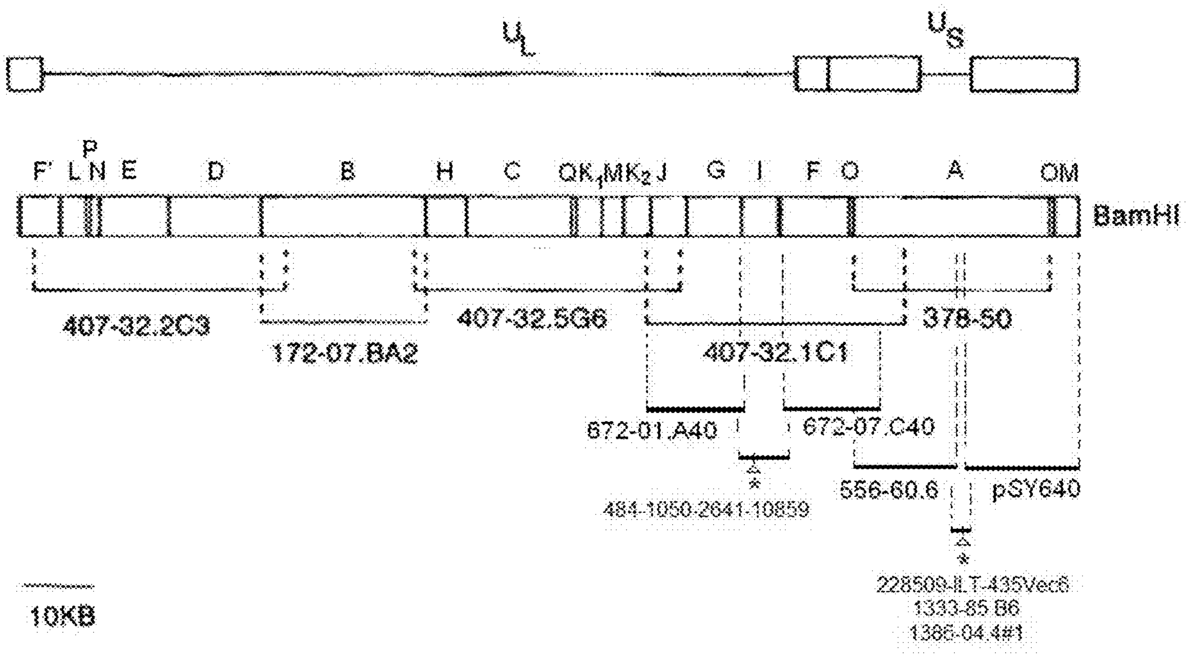
FIG. 1 is a schematic drawing of the HVT (FC126) genome, consisting of a unique long (UL) region, and a unique short (US) region, each denoted by straight lines, and flanked by repeat regions, denoted as boxes. Below the genome schematic, is a bar indicating the location of BamHI restriction enzyme digestion fragments, relative to their genome position, and the lettering nomenclature associated with each fragment. (The largest fragment was given the letter "A", the next largest given the letter "B", and so forth and so on). The positions of each cloned subgenomic fragment (and their designation) used to reconstruct either HVT (FC126) or the rHVT/ILT/IBDV viruses are indicated below the BamHI restriction map. The asterisk (*) indicates the position of the insertion sites: UL54.5 in 484-1050-2641-10859; US2 in 228509-ILT-435Vec6, 1333-85.66 or 1386-04.4#1.

The present invention overcomes the prior failure to be able to construct a single $rMDV_{np}$ vector that encodes and expresses antigens from both ILTV and IBDV. In particular embodiments, an $rMDV_{np}$ of the present invention encodes and expresses foreign antigens from only ILTV and IBDV, and are designed to aid in the protection against Mareks disease, Infectious Bursal Disease (Gumboro disease), and Infectious Laryngotraceitis virus. In specific embodiments, the $rMDV_{np}$ is an rHVT. In alternative embodiments, the $rMDV_{np}$ is an rMDV2. In a completely different aspect, the recombinant vector that encodes and expresses the foreign antigens from ILTV and IBDV is not an $rMDV_{np}$, but rather a chimeric Marek's Disease virus that contains specified genomic sequences from MDV1 replacing their counterparts in an HVT vector, e.g., the novel avian herpes virus (NAHV) [see e.g., U.S. Pat. No. 6,913,751].

Prior to the present invention, an HVT vector already had been constructed containing an NDV gene inserted into the US10 region. This HVT-NDV vector was shown to be stable and to express sufficient levels of the corresponding NDV gene product, the NDV F protein, to protect vaccinated chickens against a virulent NDV challenge. In addition, an HVT vector already had been constructed containing a pair of ILTV genes inserted in the HVT UL54.5 region. This HVT-ILTV vector was shown to be stable and to express sufficient levels of the corresponding ILTV gene products, the ILTV gI and gD proteins, to protect vaccinated chickens against a virulent ILTV challenge virus.

Previously, a multivalent HVT construct to protect against both NDV and ILTV was designed based on the successful constructs above, i.e., inserting the NDV-F gene in the US10 site and inserting the ILTV gD and gI genes in UL54.5 site [see, U.S. Pat. No. 8,932,604 B2]. Unexpectedly however, following the passaging of this construct in tissue culture the recombinant virus lost its ability to express the ILTVgD, ILTVgI, and NDV F proteins. This proved to be true with a number of duplicate recombinant HVT constructs. Indeed, these recombinant viruses were unstable and unsuitable for further development as vaccines. These findings demonstrate that the design of a single multivalent rHVT vector that can stably express both the NDV F protein and the ILTVgD and ILTVgI proteins was not a simple process that can be extrapolated from existing information. Indeed, if such stable and efficacious multivalent rHVT vectors were possible at all, their design needed to be premised on an unpredictable set of complex interactions minimally involving the relationship between the insertion sites used and the foreign nucleotide sequences to be inserted. Accordingly, the design of rHVT constructs remains unpredictable from the known art.

The present invention therefore, provides recombinant $MDV_{np}$ vectors in which two genes from ILTV and one gene from IBDV have been inserted. In a particular embodiment of the present invention all three genes were inserted in the US2 region of the HVT genome. In another embodiment of the present invention all three genes were inserted in the UL54.5 site of the HVT genome. Accordingly, such $rMDV_{np}$ vectors should be capable to be used to provide protection against both IBDV and ILTV infections. Previously, two separate rHVT vectors were necessary to protect against these two viruses, namely one for protection against ILTV and the other for protection against IBDV.

The present invention therefore, is advantageous over current methods because it should be able to provide simultaneous protection against ILTV and IBDV by inoculation of poultry and/or poultry eggs with only a single recombinant $MDV_{np}$. In particular, this allows for additonal vaccines to be administered via the in ovo route, because there is a limit on how much volume can be injected into an egg, and further saves on manufacturing costs because only one rather than two vectors is needed. Moreover, this can allow an additional antigen to be included in the vaccine such as an attenuated and/or mild live NDV, e.g., strain C2.

Furthermore, the present invention includes embodiments that comprise different $rMDV_{np}$ constructs in the same vaccine and/or immunogenic compositions. In certain embodiments of this type, the vaccine and/or immunogenic composition comprise both an rMDV2 and an rHVT, each of which encode one or more foreign antigens. Indeed, unlike the combination of two rHVTs, which inevitably lead to one construct significantly overgrowing the other, combining an rHVT with an rMDV2 leads to no such significant overgrowth. Therefore, in specific embodiments, a vaccine of the present invention comprises an rHVT that encodes an ILTVgD protein, an ILTVgI protein, and an IBDV VP2 protein with an rMDV2 that encodes yet another poultry viral antigen, e.g., the NDV F protein.

In order to more fully appreciate the instant invention, the following definitions are provided.

The use of singular terms for convenience in description is in no way intended to be so limiting. Thus, for example, reference to a composition comprising "a polypeptide" includes reference to one or more of such polypeptides.

As used herein a "nonpathogenic Marek's Disease Virus" or "$MDV_{np}$" or "npMDV" is a virus in the MDV family that shows little to no pathogenicity in poultry. The term "$MDV_{np}$" includes naturally occurring MDVs that have been passaged or otherwise similarly manipulated, but does not include viral constructs in which a specific region of the genome of one MDV serotype is replaced by the corresponding region of a different MDV serotype to form a chimeric virus, such as the novel avian herpesvirus (NAHV). In certain embodiments, the $MDV_{np}$ is an HVT. In other embodiments, the $MDV_{np}$ is an MDV2. In particular embodiments of this type, the MDV2 is SB1.

As used herein, an $MDV_{np}$ that has been genetically modified to encode a heterologous nucleotide sequence (e.g., a foreign gene) is defined as a "recombinant $MDV_{np}$" or "$rMDV_{np}$". The term "$rMDV_{np}$" includes naturally occurring $MDV_{np}$'s that have been genetically modified to encode a heterologous nucleotide sequence, but does not include viral constructs in which a specific region of the genome of one MDV serotype is replaced by the corresponding region of a different MDV serotype to form a chimeric virus, such as the novel avian herpesvirus (NAHV).

As used herein a "novel avian herpesvirus" ("NAHV") is a recombinant chimeric virus comprising a unique long viral genomic region which naturally occurs in herpesvirus of turkeys virus (HVT) and a unique short viral genomic region which naturally occurs in Marek's disease 1 (MDV1) [see, U.S. Pat. Nos. 5,965,138, 6,183,753, 6,913,751 B2]. In a preferred emdodiment the NAHV comprises a unique long viral genomic region which naturally occurs in herpesvirus of turkeys virus (HVT), a unique short viral genomic region which naturally occurs in Marek's disease 1 (MDV1), and the repeat viral regions of the HVT [see, U.S. Pat. No. 6,913,751 B2].

As used herein, a "nonessential site" is a site in the $MDV_{np}$ genome (or alternatively in the NAVH genome) in which an insertion of a heterologous nucleotide sequence into that site does not prevent the $MDV_{np}$ (or NAVH) from replicating in a host cell. Nonessential sites are generally identified by the gene in which they reside, e.g., the US2 site, or a region between two genes, e.g., the UL7/8 site. The use of the term "nonessential site" is in no way intended to even suggest that there is only a single unique nucleotide position in the nucleotide sequence of a given gene (or in the region between two genes) where an insertion of a heterologous nucleic acid must be made in order for the $MDV_{np}$ (or NAVH) to maintain its ability to replicate in a host cell.

As used herein, when an $rMDV_{np}$ (or NAHV) is said to comprise a given nucleic acid "inserted" in a nonessential site in the $rMDV_{np}$ genome (or NAHV genome), it means that the given nucleic acid is a heterologous nucleic acid that is located in that nonessential site of the $MDV_{np}$ (or NAHV). Accordingly, an $rMDV_{np}$ comprising a first nucleic acid inserted in a first nonessential site in the $rMDV_{np}$ genome and a second nucleic acid inserted in a second nonessential site in the $rMDV_{np}$ genome is equivalent to an $rMDV_{np}$ comprising a first heterologous nucleic acid located in a first nonessential site in the $rMDV_{np}$ genome and a second heterologous nucleic acid located in a second nonessential site in the $rMDV_{np}$ genome, and vice versa.

As used herein the term "poultry" can include chickens, turkeys, ducks, geese, quail, and pheasants.

As used herein, a "vaccine" is a composition that is suitable for application to an animal (including, in certain embodiments, humans, while in other embodiments being specifically not for humans) comprising one or more antigens typically combined with a pharmaceutically acceptable carrier such as a liquid containing water, which upon administration to the animal induces an immune response strong enough to minimally aid in the protection from a clinical disease arising from an infection with a wild-type microorganism, i.e., strong enough for aiding in the prevention of the clinical disease, and/or preventing, ameliorating or curing the clinical disease. As established by the USDA and codified in the Title 9 Code of Federal Regulations, part 113 (9CFR 113) «Standard requirements for Animal Products» live virus vaccines must provide at least 90% protection, in the case of NDV, IBDV and ILTV, and at least 80% in the case of MDV, from clinical signs or lesions associated with the disease to obtain a license.

As used herein, a "multivalent vaccine" is a vaccine that comprises two or more different antigens. In a particular embodiment of this type, the multivalent vaccine stimulates the immune system of the recipient against two or more different pathogens.

As used herein, the term "aids in the protection" does not require complete protection from any indication of infection. For example, "aids in the protection" can mean that the protection is sufficient such that, after challenge, symptoms of the underlying infection are at least reduced, and/or that one or more of the underlying cellular, physiological, or biochemical causes or mechanisms causing the symptoms are reduced and/or eliminated. It is understood that "reduced," as used in this context, means relative to the state of the infection, including the molecular state of the infection, not just the physiological state of the infection.

As used herein, an "adjuvant" is a substance that is able to favor or amplify the cascade of immunological events, ultimately leading to a better immunological response, i.e., the integrated bodily response to an antigen. An adjuvant is in general not required for the immunological response to occur, but favors or amplifies this response.

As used herein, the term "pharmaceutically acceptable" is used adjectivally to mean that the modified noun is appropriate for use in a pharmaceutical product. When it is used, for example, to describe an excipient in a pharmaceutical vaccine, it characterizes the excipient as being compatible with the other ingredients of the composition and not disadvantageously deleterious to the intended recipient.

As used herein, "systemic administration" is administration into the circulatory system of the body (comprising the cardiovascular and lymphatic system), thus affecting the body as a whole rather than a specific locus such as the gastro-intestinal tract (via e.g., oral or rectal administration) and the respiratory system (via e.g., intranasal administration). Systemic administration can be performed e.g., by administering into muscle tissue (intramuscular), into the dermis (intradermal or transdermal), underneath the skin (subcutaneous), underneath the mucosa (submucosal), in the veins (intravenous) etc.

As used herein the term "parenteral administration" includes subcutaneous injections, submucosal injections, intravenous injections, intramuscular injections, intradermal injections, and infusion.

The term "approximately" is used interchangeably with the term "about" and signifies that a value is within twenty-five percent of the indicated value i.e., a peptide containing "approximately" 100 amino acid residues can contain between 75 and 125 amino acid residues.

As used herein, the term, "polypeptide" is used interchangeably with the terms "protein" and "peptide" and denotes a polymer comprising two or more amino acids connected by peptide bonds. The term "polypeptide" as used herein includes a significant fragment or segment, and encompasses a stretch of amino acid residues of at least about 8 amino acids, generally at least about 12 amino acids, typically at least about 16 amino acids, preferably at least about 20 amino acids, and, in particularly preferred embodiments, at least about 30 or more amino acids, e.g., 35, 40, 45, 50, etc. Such fragments may have ends which begin and/or end at virtually all positions, e.g., beginning at residues 1, 2, 3, etc., and ending at, e.g., 155, 154, 153, etc., in all practical combinations.

Optionally, a polypeptide may lack certain amino acid residues that are encoded by a gene or by an mRNA. For example, a gene or mRNA molecule may encode a sequence of amino acid residues on the N-terminus of a polypeptide (i.e., a signal sequence) that is cleaved from, and therefore, may not be part of the final protein.

As used herein the term "antigenic fragment" in regard to a particular protein (e.g., a protein antigen) is a fragment of that protein (including large fragments that are missing as little as a single amino acid from the full-length protein) that is antigenic, i.e., capable of specifically interacting with an antigen recognition molecule of the immune system, such as an immunoglobulin (antibody) or T cell antigen receptor. For example, an antigenic fragment of an IBDV VP2 protein is a fragment of the VP2 protein that is antigenic. Preferably, an antigenic fragment of the present invention is immunodominant for antibody and/or T cell receptor recognition.

As used herein an amino acid sequence is 100% "homologous" to a second amino acid sequence if the two amino acid sequences are identical, and/or differ only by neutral or conservative substitutions as defined below. Accordingly, an amino acid sequence is about 80% "homologous" to a second amino acid sequence if about 80% of the two amino acid sequences are identical, and/or differ only by neutral or conservative substitutions.

Functionally equivalent amino acid residues often can be substituted for residues within the sequence resulting in a conservative amino acid substitution. Such alterations define the term "a conservative substitution" as used herein. For example, one or more amino acid residues within the sequence can be substituted by another amino acid of a similar polarity, which acts as a functional equivalent, resulting in a silent alteration. Substitutions for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to affect apparent molecular weight as determined by polyacrylamide gel electrophoresis, or isoelectric point.

Particularly preferred conservative substitutions are: Lys for Arg and vice versa such that a positive charge may be maintained; Glu for Asp and vice versa such that a negative charge may be maintained; Ser for Thr such that a free —OH can be maintained; and Gln for Asn such that a free $NH_2$ can be maintained. The amino acids also can be placed in the following similarity groups: (1) proline, alanine, glycine, serine, and threonine; (2) glutamine, asparagine, glutamic acid, and aspartic acid; (3) histidine, lysine, and arginine; (4) cysteine; (5) valine, leucine, isoleucine, methionine; and (6) phenylalanine, tyrosine, and tryptophan.

In a related embodiment, two highly homologous DNA sequences can be identified by their own homology, or the homology of the amino acids they encode. Such comparison of the sequences can be performed using standard software available in sequence data banks. In a particular embodiment two highly homologous DNA sequences encode amino acid sequences having about 80% identity, more preferably about 90% identity and even more preferably about 95% identity. More particularly, two highly homologous amino acid sequences have about 80% identity, even more preferably about 90% identity and even more preferably about 95% identity.

As used herein, protein and DNA sequence percent identity can be determined using software such as MacVector v9, commercially available from Accelrys (Burlington, Mass.) and the Clustal W algorithm with the alignment default parameters, and default parameters for identity. See, e.g., Thompson, et al., 1994. *Nucleic Acids Res.* 22:4673-4680. ClustalW is freely downloadable for Dos, Macintosh and Unix platforms from, e.g., EMBLI, the European Bioinformatics Institute. The present download link is found at http://www.ebi.ac.uk/clustalw/. These and other available programs can also be used to determine sequence similarity using the same or analogous default parameters.

As used herein the terms "polynucleotide", or a "nucleic acid" or a "nucleic acid molecule" are used interchangeably and denote a molecule comprising nucleotides including, but is not limited to, RNA, cDNA, genomic DNA and even synthetic DNA sequences. The terms are also contemplated to encompass nucleic acid molecules that include any of the art-known base analogs of DNA and RNA.

A nucleic acid "coding sequence" or a "sequence encoding" a particular protein or peptide, is a nucleotide sequence which is transcribed and translated into a polypeptide in vitro or in vivo when placed under the control of appropriate regulatory elements.

The boundaries of the coding sequence are determined by a start codon at the 5'-terminus and a translation stop codon at the 3'-terminus. A coding sequence can include, but is not limited to, prokaryotic sequences, cDNA from eukaryotic mRNA, genomic DNA sequences from eukaryotic (e.g., avian) DNA, and even synthetic DNA sequences. A transcription termination sequence can be located 3' to the coding sequence.

"Operably linked" refers to an arrangement of elements wherein the components so described are configured so as to perform their usual function. Thus, control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter and the coding sequence and the promoter can still be considered "operably linked" to the coding sequence.

As used herein, the term "transcription terminator sequence" is used interchangeably with the term "polyadenylation regulatory element" and is a sequence that is generally downstream from a DNA coding region and that may be required for the complete termination of the transcription of that DNA coding sequence. A transcription terminator is a regulatory DNA element involved in the termination of the transcription of a coding region into RNA. Generally, such an element encodes a section, e.g. a hairpin structure, which has a secondary structure that can cause the RNA polymerase complex to stop transcription. A transcription terminator is therefore always situated downstream of the stop codon from the region to be translated, the 3' untranslated region.

As used herein an "expression cassette" is a recombinant nucleic acid that minimally comprises a promoter and a heterologous coding sequence operably linked to that promoter. In many such embodiments, the expression cassette further comprises a transcription terminator sequence. Accordingly, the insertion of an expression cassette into a nonessential site of the $rMDV_{np}$ genome can lead to the expression of the heterologous coding sequence by the $rMDV_{np}$. In specific embodiments, the $rMDV_{np}$ is an rHVT. In alternative embodiments, the $rMDV_{np}$ is an rMDV2.

A "heterologous nucleotide sequence" as used herein is a nucleotide sequence that is added to a nucleotide sequence of the present invention by recombinant methods to form a nucleic acid that is not naturally formed in nature. In specific embodiments, a "heterologous nucleotide sequence" of the present invention can encode a protein antigen such as the IBDV VP2 protein, the ILTV gI protein, and/or the ILTV gD protein. Heterologous nucleotide sequences can also encode fusion (e.g., chimeric) proteins. In addition, a heterologous nucleotide sequence can encode peptides and/or proteins that contain regulatory and/or structural properties. In other such embodiments, a heterologous nucleotide sequence can encode a protein or peptide that functions as a means of detecting the protein or peptide encoded by the nucleotide sequence of the present invention after the recombinant nucleic acid is expressed. In still another embodiment, the heterologous nucleotide sequence can function as a means of detecting a nucleotide sequence of the present invention. A heterologous nucleotide sequence can comprise non-coding sequences including restriction sites, regulatory sites, promoters and the like. A "heterologous nucleic acid" comprises a heterologous nucleotide sequence.

Insertion of a nucleic acid encoding an antigen of the present invention into an $rMDV_{np}$ vector is easily accomplished when the termini of both the nucleic acid and the vector comprise compatible restriction sites. If this cannot be done, it may be necessary to modify the termini of the nucleotide sequence and/or vector by digesting back single-stranded nucleic acid overhangs (e.g., DNA overhangs) generated by restriction endonuclease cleavage to produce blunt ends, or to achieve the same result by filling in the single-stranded termini with an appropriate polymerase. Alternatively, desired sites may be produced, e.g., by ligating nucleotide sequences (linkers) onto the termini. Such linkers may comprise specific oligonucleotide sequences that define desired restriction sites. Restriction sites can also be generated through the use of the polymerase chain reaction (PCR). [See, e.g., Saiki et al., *Science* 239:487-491 (1988)]. The cleaved vector and the DNA fragments may also be modified, if required, by homopolymeric tailing.

Protein Antigens and Nucleic Acids Encoding the Protein Antigens

The ILTV gD gene appears to encode a glycoprotein of 434 amino acids in length having a molecular weight of 48,477 daltons, although others have suggested that a downstream start codon, which leads to an ILTV gD protein comprising only 377 amino acid residues, is the actual start codon [Wild et al., *Virus Genes* 12:104-116 (1996)]. The ILTV gI gene encodes a glycoprotein of 362 amino acids in length having a molecular weight of 39,753 daltons [U.S. Pat. No. 6,875,856, hereby incorporated by reference]. Nucleic acids encoding natural and/or laboratory derived variants of the ILTV gD and ILTV gI may be substituted for those presently exemplified.

In particular embodiments of the present invention, an $rMDV_{np}$ comprises a recombinant nucleic acid (e.g., an expression cassette) that encodes an ILTV gD protein comprising the amino acid sequence of SEQ ID NO: 2 or an antigenic fragment thereof. In related embodiments the $rMDV_{np}$ comprises a recombinant nucleic acid that encodes an ILTV gD protein comprising an amino acid sequence that has greater than 90%, and/or greater than 95%, and/or greater than 98%, and/or greater than 99% identity to the amino acid sequence of SEQ ID NO: 2. In particular embodiments, the ILTV gD protein is encoded by the nucleotide sequence of SEQ ID NO: 1. In specific embodiments, the $rMDV_{np}$ is an rHVT. In alternative embodiments, the $rMDV_{np}$ is an rMDV2.

In certain embodiments of the present invention, an $rMDV_{np}$ comprises a recombinant nucleic acid (e.g., an expression cassette) that encodes an ILTV gI protein comprising the amino acid sequence of SEQ ID NO: 4 or an antigenic fragment thereof. In related embodiments, the $rMDV_{np}$ comprises a recombinant nucleic acid that encodes an ILTV gI protein comprising an amino acid sequence that has greater than 90%, and/or greater than 95%, and/or greater than 98%, and/or greater than 99% identity to the amino acid sequence of SEQ ID NO: 4. In particular embodiments, the ILTV gI protein is encoded by the nucleotide sequence of SEQ ID NO: 3. In specific embodiments, the $rMDV_{np}$ is an rHVT. In alternative embodiments, the $rMDV_{np}$ is an rMDV2.

As mentioned earlier, IBDV is a member of the Birnaviridae family, which has a genome consisting of two segments (A and B) of double-stranded RNA. The larger segment A encodes a polyprotein of 110 kDa, which is subsequently cleaved by autoproteolysis to form mature viral proteins VP2, VP3 and VP4. Of these, VP2 and VP3 are the structural capsid proteins for the virion, with VP2 protein being the major host-protective immunogen. In the case of IBDV, two serotypes exist, serotype 1 and 2 which can be distinguished by virus neutralization (VN) tests. Serotype 1 viruses have been shown to be pathogenic to chickens, while serotype 2 IBDV only causes sub-acute disease in turkeys. Historically, IBDV serotype 1 viruses consisted of only one type that is known as "classic" IBD virus, but subsequently, so-called "variant" IBDV strains have emerged. In particular embodiments of the present invention the IBDV VP2 gene encodes a VP2 protein from an IBDV that is of the classic type. Such genes are well known and their sequence information is readily available,[ see e.g., GenBank acc.nr: D00869 (F52/70), D00499 (STC), or AF499929 (D78)]. Alternatively, this gene can be obtained from the genome of a classic IBDV isolated from nature, using routine techniques for manipulating a Birnavirus. Classic type IBDV's can be readily identified using serology, or molecular biology.

In particular embodiments of the present invention, an $rMDV_{np}$ comprises a recombinant nucleic acid (e.g., an expression cassette) that encodes an IBDV VP2 protein comprising the amino acid sequence of SEQ ID NO: 6 or an antigenic fragment thereof. In related embodiments, the $rMDV_{np}$ comprises a recombinant nucleic acid that encodes an IBDV VP2 protein comprising an amino acid sequence that has greater than 90%, and/or greater than 95%, and/or greater than 98%, and/or greater than 99% identity to the amino acid sequence of SEQ ID NO: 6. In specific embodiments, the IBDV VP2 protein is encoded by the nucleotide sequence of SEQ ID NO: 5. In specific embodiments, the $rMDV_{np}$ is an rHVT. In alternative embodiments, the $rMDV_{np}$ is an rMDV2.

Routine vaccinations against IBDV are performed as early as possible in the life of poultry using attenuated IBDV strains, but these can only be applied when the level of MDA against IBDV has decreased enough, which commonly is somewhere between 15 and 20 days post hatch. Many 'live' or inactivated IBDV vaccines are commercially available, e.g., a 'live' vaccine such as Nobilis™ Gumboro D78 (Merck Animal Health).

NDV has a non-segmented, negative sense, single stranded RNA genome, which is about 15 kb in size, and contains six genes, amongst which is the NDV F protein gene which encodes the so-called "fusion" glycoprotein (F protein). The F protein is involved in NDV's attachment of and entry into host cells, and as the immunodominant protein it can be the basis of an effective immune response against NDV. The NDV F protein is expressed as a native FO protein, which is activated upon cleavage by extra-cellular peptidases.

An NDV F protein gene, for example, can be derived from NDV Clone 30, a common lentogenic NDV vaccine strain. Nucleic acids encoding natural and/or laboratory derived variants of the F protein gene would equally be applicable, either from lentogenic, mesogenic or velogenic NDV, as the F protein gene sequence itself is highly conserved in these different NDV pathotypes.

Promoters and Polyadenylation Regulatory Elements

A promoter is a functional region on the genome of an organism that directs the transcription of a downstream coding region. A promoter is therefore situated upstream of the coding region of a gene. The mRNA synthesis directed by the promoter starts from the 'transcription start site' (TSS). The mRNA produced is in turn translated into protein starting from the gene's start codon, which is the first ATG sequence in the open reading frame (the first AUG in the mRNA). Typically the TSS is located at 30-40 nucleotides upstream of the start codon. A TSS can be determined by sequencing the 5' end of the mRNA of a gene, e.g. by the RACE technique. In general promoters are comprised within about 1000 nucleotides upstream of the position of the A of the start codon, which is generally denoted as A+1, and most promoters are situated between nucleotides −500 and A+1.

The nomenclature for a promoter is commonly based on the name of gene that it controls the expression of. For example, the murine cytomegalovirus immediate early 1 gene (mCMV-IE1) promoter "mCMV-IE1 gene promoter", refers to the promoter that naturally drives the expression of the early 1 gene (1E1 gene) for mCMV and accordingly, is situated immediately upstream of that gene. Because the IE1-gene is such a well-documented and clearly recognizable gene, and because the genomes of several mCMVs have been sequenced (in whole or in part), such a promoter readily can be identified by routine techniques. For example, in a basic protocol a promoter can be obtained by roughly sub-cloning the region in between two consecutive genes, e.g. from the poly A signal of an upstream gene to the TSS of a downstream gene. The promoter then can be identified by standard tests, e.g., by the expression of a marker gene by progressively smaller sections of a suspected promoter.

Generally, promoters contain a number of recognizable regulatory regions, such as an enhancer region, which is involved in binding regulatory factors that influence the time, the duration, the conditions, and the level of transcription. Whereas the enhancer region is normally situated upstream, a promoter also contains a region more downstream that is involved in the binding of transcription factors and directing RNA polymerase itself. This downstream region generally contains a number of conserved promoter sequence elements such as the TATA box, the CAAT box, and the GC box.

A promoter comprising both the enhancer—and the downstream region is termed a "complete" promoter, whereas a promoter comprising only the downstream region, is termed a "core" promoter.

A promoter for the expression of a (heterologous) gene in a (virus) vector needs to be able to effectively drive the transcription of that downstream coding sequence. This is generally referred to as the promoter being "operatively linked" to the coding sequence, such that the gene is 'under the control' of the promoter, or is 'driven by' the promoter. This generally means that in an expression cassette the promoter and the coding sequence of the gene are found on the same nucleic acid, in effective proximity, and with no signals or sequences between them that would intervene with effective transcription of the coding sequence.

The mCMV-IE1 gene promoter is well known in the art, and can be readily obtained from a variety of commercial sources, such as from suppliers of commercial plasmids for cloning and expression. The 1E1 gene is also called the 'major IE gene'. The mCMV-IE1 protein has also been referred to as pp89. Dörsch-Häsler et al. [*Proc. Nat. Acad. Sci.,* 82:8325-8329 (1985)] described the mCMV IE1 gene promoter in 1985, and the use of this promoter in heterologous expression is also described in WO 87/03.905 and EP 728,842. The nucleotide sequence of the complete mCMV IE locus is available from GenBank under acc. nr. L06816.1 (from March 2004). The mCMV itself is available from the ATCC: initially under acc. nr. VR-194, and more recently this has been continued under acc. nr. VR-1399.

In one embodiment of the invention, the mCMV-IE1 gene promoter is a complete promoter, comprising both the core promoter region, as well as the enhancer region for the mCMV-IE1 gene. The complete mCMV-IE1 gene promoter is about 1.4 kb in size. However, the present invention also allows for some variance in length of not only the mCMV IE1-gene promoter, but also of the other elements that make up the recombinant DNA expression cassette employed in the present invention. This can result from differences in the exact conditions that are used for cloning and construction. For example, this variance may arise from using different restriction enzyme sites, PCR cloning primers, or different conditions for adapting the ends of the cloning molecules used. Consequently, some variation in length—smaller or larger— of the constituting elements may occur, without affecting the stability, and relatively strong antigen expression and/or efficacy of the overall expression cassette. In that case these length differences are immaterial, and are within the scope of the invention. Therefore, an mCMV-IE1 gene promoter of "about 1.4 kb" is: 1.4 kb±about 25%. In particular embodiments the promoter is 1.4 kb±about 20%. In still other embodiments the variance can be 1.4 kb±about 15%, 1.4 kb±about 12%, 1.4 kb±about 10%, 1.4 kb±about 8%, 1.4 kb±about 6%, 1.4 kb±about 5%, 1.4 kb±about 4%, 1.4 kb±about 3%, 1.4 kb±about 2%, or even 1.4 kb±about 1%.

Similarly, homologs or variants of the promoter element may be used that are equally effective and stable. Therefore, in certain embodiments the mCMV-IE1 gene promoter of the present invention can be a DNA molecule of about 1.4 kb that comprises a nucleotide sequence with at least 95%, 96%, 97%, 98%, or even 99% nucleotide sequence identity to the nucleotide sequence of SEQ ID NO: 10. In a particular embodiment the mCMV-IE1 gene promoter consists of nucleotide sequence of SEQ ID NO: 10.

Many alternative promoters can be used to drive the expression of a heterologous gene encoding a protein antigen or antigenic fragment thereof in an $rMDV_{np}$ of the present invention. Examples include the pseudorabies virus (PRV) gpX promoter [see, WO 87/04463], the Rous sarcoma virus LTR promoter, the SV40 early gene promoter, the chicken beta-actin gene promoter comprising the nucleotide sequence of SEQ ID NO: 11, the Towne Strain hCMV IE promoter, a derivative of the hCMV IE promoter (from strain AD169) comprising the nucleotide sequence of SEQ ID NO: 12, an ILTV gD promoter comprising the nucleotide sequence of SEQ ID NO: 7, and an ILTV gI promoter comprising the nucleotide sequence of SEQ ID NO: 8, [see e.g., U.S. Pat. No. 6,183,753 B1], the human cytomegalovirus immediate early1 (hCMV IE1) gene promoter [U.S. Pat. Nos. 5,830,745; 5,980,906], and the chicken beta-actin gene promoter [EP 1 298 139 B1]. A particular heterologous promoter for the IBDV VP2 gene is the murine (mCMV IE1) cytomegalovirus promoter. In a particular embodiment of this type the mCMV 1E1 comprises the nucleotide sequence of SEQ ID NO: 10 [see e.g., EP 728,842; PCT/EP2015/081121].

The inclusion of a polyadenylation regulatory element downstream from a DNA coding region is oftentimes required to terminate the transcription of the coding DNA sequence. Accordingly, many genes comprise a polyadenylation regulatory element at the downstream end of their coding sequence. Many such regulatory elements have been identified and can be used in an $rMDV_{np}$ of the present invention. Specific examples of polyadenylation regulatory elements as exemplified herein, include a FHV US-9 polyadenylation signal comprising the nucleotide sequence of SEQ ID NO: 13, and the HSV thymidine kinase polyadenylation signal comprising the nucleotide sequence of SEQ ID NO: 14.

Vaccines and Immunogenic Compositions

The present invention relates to the use of the recombinant $MDV_{np}$, the nucleic acid molecules used to construct the $MDV_{np}$, or the host cells to grow them, or any combination thereof, all according to the present invention for the manufacture of a vaccine for poultry. Accordingly, the present invention provides vaccines and/or immunogenic compositions that include a multivalent recombinant $MDV_{np}$ of the present invention. Such vaccines can be used to aid in the prevention and/or prevent Infectious Bursal Disease (Gumboro disease), and/or Marek's disease, and/or maladies associated with ILTV infections. A vaccine according to the present invention can be used for prophylactic and/or for therapeutic treatment, and thus can interfere with the establishment and/or with the progression of an infection and/or its clinical symptoms of disease.

A recombinant $MDV_{np}$ of the present invention can be grown by any number of means currently practiced in the field. For example, a recombinant $MDV_{np}$ of the present invention can be grown through the use of in vitro cultures of primary chicken cells, see e.g., the Examples below where chicken embryo fibroblast cells (CEFs) were used. The CEFs can be prepared by trypsinization of chicken embryos. The CEFs also can be plated in monolayers and then infected with the $MDV_{np}$. This particular process can be readily scaled up to industrial-sized production.

Therefore, a further aspect of the invention relates to a method for the preparation of the vaccine according to the invention comprising the steps of infecting host cells with a recombinant $MDV_{np}$ of the present invention, harvesting the infected host cells, and then admixing the harvested infected host cells with a pharmaceutically acceptable carrier.

Suitable methods for infection, culture and harvesting are well known in the art and are described and exemplified herein.

Typically, the infected host cells are harvested while still intact to obtain the recombinant $MDV_{np}$ in its cell-associated form. These cells can be taken up in an appropriate carrier composition to provide stabilization for storage and freezing. The infected cells can be filled into glass ampoules, which are sealed, frozen and stored in liquid nitrogen. Accordingly, in certain embodiments of the present invention, the vaccines and/or immunogenic compositions of the present invention are stored frozen and accordingly, comprise a cryropreservative, such as dimethyl sulfoxide (DMSO), to preserve the frozen infected cells.

Alternatively, when the recombinant $MDV_{np}$ is a recombinant HVT, it can be isolated from its host cell, for instance through sonication at the end of culturing, and then taken up into a stabilizer, and freeze-dried (lyophilized) for stable storage or otherwise reduced in liquid volume, for storage, and then reconstituted in a liquid diluent before or at the time of administration. Such reconstitution may be achieved using, for example, vaccine-grade water. In certain embodiments, a lyophilized portion of a multivalent vaccine can comprise one or more antigens and the diluent can comprise one or more other antigens.

In particular embodiments a vaccine of the present invention (or a portion thereof) can be in a freeze-dried form, e.g., as tablets and/or spheres that are produced by a method described in WO 2010/125084, hereby incorporated by reference in its entirety. In particular, reference is made to the examples, from page 15, line 28 to page 27, line 9 of WO 2010/125084, describing a method to produce such fast disintegrating tablets/spheres. Such freeze-dried forms can be readily dissolved in a diluent, to enable systemic administration of the vaccine.

Vaccines and immunogenic compositions can, but do not necessarily include, physiologically compatible buffers and saline and the like, as well as pharmaceutically acceptable adjuvants. Adjuvants can be useful for improving the immune response and/or increasing the stability of vaccine preparations. Adjuvants are typically described as non-specific stimulators of the immune system, but also can be useful for targeting specific arms of the immune system. One or more compounds which have this activity may be added to the vaccine. Therefore, particular vaccines of the present invention can further comprise an adjuvant. Examples of chemical compounds that can be used as adjuvants include, but are not limited to aluminum compounds (e.g., aluminum hydroxide), metabolizable and non-metabolizable oils, mineral oils including mannide oleate derivatives in mineral oil solution (e.g., MONTANIDE ISA 70 from Seppic SA, France), and light mineral oils such as DRAKEOL 6VR, block polymers, ISCOM's (immune stimulating complexes), vitamins and minerals (including but not limited to: vitamin E, vitamin A, selenium, and vitamin B12) and CARBOPOL®.

Other suitable adjuvants, which sometimes have been referred to as immune stimulants, include, but are not limited to: cytokines, growth factors, chemokines, supernatants from cell cultures of lymphocytes, monocytes, cells from lymphoid organs, cell preparations and/or extracts from plants, bacteria or parasites (*Staphylococcus aureus* or lipopolysaccharide preparations) or mitogens. Generally, an adjuvant is administered at the same time as an antigen of the present invention. However, adjuvants can also or alternatively be administered within a two-week period prior to the vaccination, and/or for a period of time after vaccination, i.e., so long as the antigen, e.g., a recombinant $MDV_{np}$ of the present invention persists in the tissues.

The vaccines and/or immunogenic compositions of the present invention may be administered by any route such as in ovo, by parenteral administration, including intramuscular injection, subcutaneous injection, intravenous injection, intradermal injection, by scarification, by oral administration, or by any combination thereof.

Furthermore, the multivalent recombinant $MDV_{np}$ of the present invention can be used and/or combined with additional IBDV, ILTV, and/or MDV antigens to improve and expand the immunogenicity provided, and/or antigens for other pathogens (e.g., NDV) in order to provide immune protection against such other pathogens. These additional antigens can be either live or killed whole microorganisms, other recombinant vectors, cell homogenates, extracts, proteins, or any other such derivative, provided that they do not negatively interfere with the safety, and stability with relatively strong antigen expression and/or efficacy of the vaccine according to the present invention.

The combination of a multivalent recombinant $MDV_{np}$ of the present invention with an additional MDV, IBDV, and/or ILTV antigen can be advantageous in those cases in which very virulent field strains of MDV, IBDV, or ILTV are prevalent, e.g., in a particular geographic region. In this regard, the combination of a multivalent recombinant $MDV_{np}$ of the present invention with an MDV1, MDV2, or HVT includes the Rispens (MDV1) strain, the SB1 (MDV2) strain, the FC-126 (HVT) strain and/or PB1 (HVT) strain. To improve the response against IBDV, multivalent recombinant $MDV_{np}$ may be combined with an IBDV vaccine strain, such as a mild live IBDV vaccine strain, e.g., D78 (cloned intermediate strain), PBG98, Cu-1, ST-12 (an intermediate strain), or 89/03 (a live Delaware variant strain) in a multivalent vaccine.

Examples of other microorganisms that can be used as antigens together with the multivalent recombinant $MDV_{np}$ of the present invention include: (i) viruses such as infectious bronchitis virus, adenovirus, egg drop syndrome virus, infectious bursal disease virus, chicken anaemia virus, avian encephalo-myelitis virus, fowl pox virus, turkey rhinotracheitis virus, duck plague virus (duck viral enteritis), pigeon pox virus, avian leucosis virus, avian pneumovirus, and reovirus, (ii) bacteria, such as *Escherichia coli, Salmonella* spec., Ornitobacterium *rhinotracheale*, Haemophilis *paragallinarum, Pasteurella multocida, Erysipelothrix rhusiopathiae*, Erysipelas spec., *Mycoplasma* spec., and *Clostridium* spec., (iii) parasites such as Eimeria spec., and (iv) fungi, such as *Aspergillus* spec. In particular embodiments of the present invention, a recombinant $MDV_{np}$ of the present invention can be combined with a mild live NDV vaccine strain such as vaccine strain C2. Many of such strains are used in commercial vaccines.

The combination vaccine can be made in a variety of ways including by combining the recombinant $MDV_{np}$ of the present invention with preparations of virus, or bacteria, or fungi, or parasites, or host cells, or a mixture of any and/or all of these. In particular embodiments, the components for such a combination vaccine are conveniently produced separately and then combined and filled into the same vaccine container.

As described above, a vaccine according to the invention can be used advantageously to provide safe and effective immune protection in poultry to a multiple diseases, by a single inoculation at very young age or in ovo. Alternatively, as would be apparent to anyone skilled in the art of poultry vaccines the combinations described above also could include vaccination schedules in which the multivalent recombinant $MDV_{np}$ of the present invention and the additional antigen are not applied simultaneously; e.g., the recombinant $MDV_{np}$ may be applied in ovo, and the NDV C2 and/or the IBDV strain (e.g., 89/03) could be applied at a subsequent time/date.

Accordingly, the vaccines of the present invention can be administered to the avian subject in a single dose or in multiple doses. For example, a vaccine of the present invention may be applied at the day of hatch and/or in ovo at day 16-18 (Embryonation Day) ED. When multiple doses are administered, they may be given either at the same time or sequentially, in a manner and time compatible with the formulation of the vaccine, and in such an amount as will be immunologically effective. Therefore, a vaccine of the present invention may effectively serve as a priming vaccination, which later can be followed and amplified by a booster vaccination of the identical vaccine, or with a different vaccine preparation e.g., a classical inactivated, adjuvanted whole-virus vaccine.

The volume per dose of a vaccine of the present invention can be optimized according to the intended route of application: in ovo inoculation is commonly applied with a volume between 0.05 and 0.5 ml/egg, and parenteral injection is commonly done with a volume between 0.1 and 1 ml/avian. In any case, optimization of the vaccine dose volume is well within the capabilities of the skilled artisan.

SEQUENCE TABLE

| SEQ ID NO: | Description | Type |
|---|---|---|
| 1 | ILTV gD Glycoprotein | nucleic acid |
| 2 | ILTV gD Glycoprotein | amino acid |
| 3 | ILTV gI Glycoprotein | nucleic acid |
| 4 | ILTV gI Glycoprotein | amino acid |
| 5 | IBDV VP2 | nucleic acid |

-continued

| SEQUENCE TABLE | | |
|---|---|---|
| SEQ ID NO: | Description | Type |
| 6 | IBDV VP2 | amino acid |
| 7 | ILTV gD promoter | nucleic acid |
| 8 | ILTV gI promoter | nucleic acid |
| 9 | ILTV insert | nucleic acid |
| 10 | mCMV IE promoter | nucleic acid |
| 11 | chicken β-actin promoter | nucleic acid |
| 12 | hCMV IE promoter (from strain AD169) | nucleic acid |
| 13 | FHV US-9 polyadenylation signal | nucleic acid |
| 14 | HSV TK polyadenylation signal | nucleic acid |
| 15 | 228509-ILT-435Vec6 (HVT/IBDV/ILT 1386-134) mCMV IEpro-VP2-SV40pA/ILT/HVT | nucleic acid |
| 16 | 1333-85.B6 (HVT/ILT/IBDV 1386-48.1.1.1) ILT/Chicken β-actin pro-VP2-FHV US9pA/HVT | nucleic acid |
| 17 | 1386-04.4#1 (HVT/ILT/IBDV 1386-48.3.1.7) ILT/hCMV IEpro-VP2-HSV TKpA/HVT | nucleic acid |
| 18 | 484-1050-2641-10859 (HVT/IBDV/ILT 484) mCMV IEpro-VP2-SV40pA/ILT/HVT | nucleic acid |
| 19 | SV40 polyadenylation signal | nucleic acid |

The present invention may be better understood by reference to the following non-limiting examples, which are provided as exemplary of the invention. The following examples are presented in order to more fully illustrate embodiments of the invention and should in no way be construed as limiting the broad scope of the invention.

EXAMPLES

Example 1

Construction of Recombinant HVT/ILTV/IBDV Virus Vectors

Recombinant multivalent non-pathogenic Marek's Disease virus constructs were prepared that encode and express both Infectious Laryngotracheitis Virus and Infectious Bursal Disease Virus protein antigens. The present invention overcomes the problem of vaccine interference encountered when two recombinant HVT vaccines, such as Innovax®-ILT (sold by Merck Animal Health) and Vaxxitek® (sold by Merial) are given to the same animal.

Recombinant virus constructs were created in which antigenic donor material from two poultry pathogens, Infectious Laryngotracheitis Virus (ILTV) and Infectious Bursal Disease virus (IBDV) are inserted into a Herpesvirus of Turkey (HVT) vector [see also, U.S. Pat. No. 8,932,604 B2, WO 2013/057,235, and WO 2016/102647, the contents of all of which are hereby incorporated by reference in its entireties]. The donor materials include a 3.563 kb SalI-HindIII fragment from ILTV, NVSL Challenge Strain, Lot #83-2 [pos. 10532-14094; Wild et al., *Virus Genes* 12:104-116(1996): Acc. #U28832], encoding the full length genes for glycoprotein D (gD) and glycoprotein I (gI), plus partial coding regions from glycoprotein E (amino acids 1-101), and ORF5 (amino acids 734-985); and an expression cassette consisting of the coding region for IBDV, Faragher, type F52/70 strain, viral protein 2 (vp2) gene, driven by a eukaryotic or viral promoter and followed by a terminator sequence. In the present embodiment, the promoter driving VP2 expression may come from the immediate early (IE) gene of human cytomegalovirus (hCMV), strain AD 169, from chicken beta-actin (cβ-act) gene or from the IE gene of mouse cytomegalovirus (mCMV) strain ATCC VR-194. The terminator and polyadenylation sequence may come from human Herpes Simplex Virus (HSV), thymidine kinase (TK) gene, from the glycoprotein B (gB) gene of Feline Herpesvirus (FHV), from the immediate early (IE) gene of human cytomegalovirus (hCMV), strain AD 169 or from simian virus 40 (SV40). The donor material may be inserted into one of two non-essential sites in the HVT vector, the US2 site [pos. 140540/140541, Afonso et al., *J. Virology* 75(2): 971-978 (2001); Acc. #AF291866, between amino acids residues 124 and 125], or in the UL54.5 site [pos. 111240/111241, Afonso et al., 2001, supra; Acc. #AF291866, between amino acids residues 21 and 22], or one insert in each site.

Genetic and phenotypic stability is a major component of the safety and relatively strong antigen expression and/or efficacy profile of any new recombinant viral vaccine candidate. The IBDV and ILTV expression cassettes inserted into the HVT backbone are not intrinsically required for viral replication and therefore may be lost due to mutation during amplification of the virus stock in tissue culture passages. A satisfactory vaccine candidate must not easily mutate to lose expression of the foreign gene insert. A vaccine candidate is considered stable if it can be demonstrated that at least 90% of the viral plaques express the inserted foreign antigenic protein following greater than or equal to 10 passages in tissue culture.

Example 2

Construction of Recombinant HVT/ILTV/IBDV Virus Vectors

The ability to generate herpesviruses by this method has previously been demonstrated for pseudorabies virus [van Zijl et al., *J. Virology* 62:2191-2195 (1988)]. This procedure subsequently was employed to construct recombinant HVT vectors [see, U.S. Pat. No. 5,853,733, hereby incorporated by references with respect to the methodology disclosed regarding the construction of recombinant HVT vectors] and was used to construct the recombinant HVT/ILTV/IBDV vectors of the present invention. In this method, the entire HVT genome is cloned into bacterial vectors as several large overlapping subgenomic fragments constructed utilizing standard recombinant DNA techniques [Maniatis et al., (1982) Molecular Cloning, Cold Spring Harbor Laboratory press, Cold Spring Harbor, N.Y. (1982); and Sambrook et al., Molecular Cloning, Cold Spring Harbor Laboratory press, Cold Spring Harbor, N.Y. (1989)]. An HVT strain FC126 cosmid library was derived from sheared viral DNA cloned into the cosmid vector pWE15 (Stratagene, now Agilent Technologies of Santa Clara, Calif.). In addition, several large genomic DNA fragments were isolated by restriction digestion with the enzyme, BamHI, and cloned into either pWE15 or the plasmid vector pSP64 (Promega, Madison Wis.). As described in U.S. Pat. No. 5,853,733, cotransfection of these fragments into chicken embryo fibroblast (CEF) cells results in the regeneration of HVT genome mediated by homologous recombination across the overlapping regions of the fragments. If an insertion is engineered directly into one or more of the subgenomic fragments prior to the cotransfection, this procedure results in a high frequency of viruses containing the insertion. Five overlapping subgenomic clones are required to generate HVT/FC126 HVT, and served as the basis for creating all HVT/ILTV/IBDV recombinant viruses.

Figure 2:
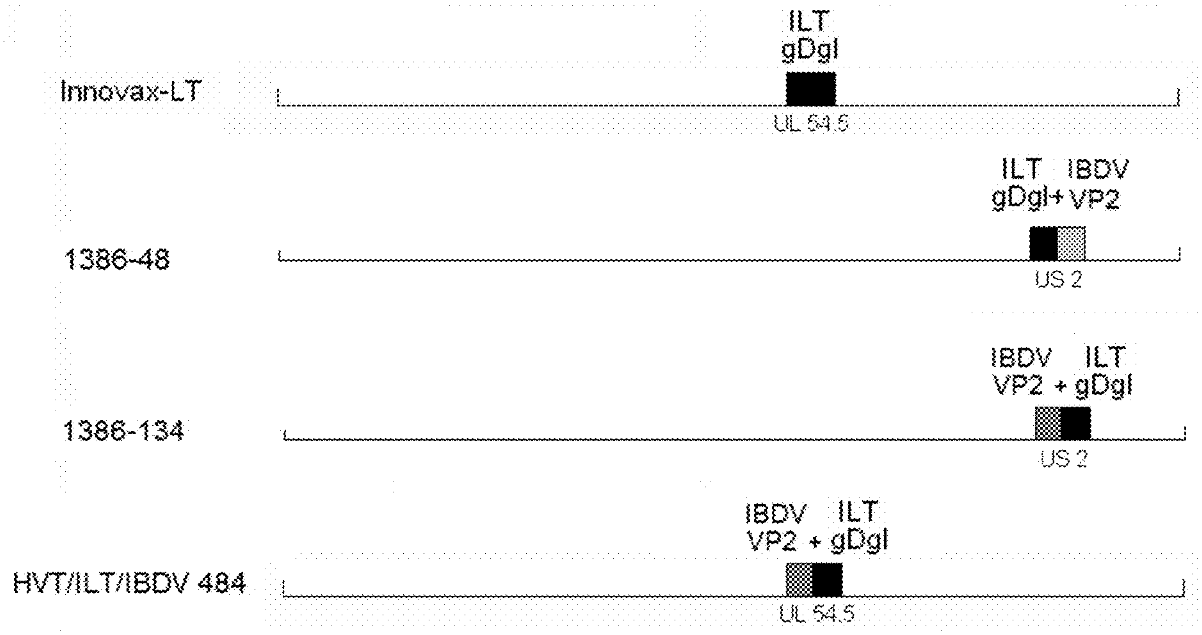
FIG. 2 is a schematic drawing of four different recombinant HVTs, which depict the genes inserted into the HVT backbone and the site of their insertion. Innovax®-ILT is an rHVT that includes an expression cassette encoding the ILTV gD and ILTV gI genes inserted in the UL54.5 site of the rHVT. 1386-48 is an rHVT that includes an expression cassette that encodes the ILTV gD, the ILTV gI, and the IBDV viral protein 2 genes inserted in the US2 site of the rHVT. 1386-134 is an rHVT that also includes both an expression cassette encoding the ILTV gD and ILTV gI, and the IBDV viral protein 2 genes inserted in the US2 site, but the cassette order is switched (i.e., VP2, then ILT gD and gI). HVT/ILT/IBDV 484 is an rHVT that includes an expression cassette that encodes the IBDV viral protein 2, the ILTV gD, and the ILTV gI genes inserted in the UL54.5 site of the rHVT.

Construction of HVT/ILT/IBDV 1386-134.1-2: [see, 1386-134 depicted in FIG. 2]

The cosmid regeneration of HVT/ILT/IBDV 1386-134.1-2 was performed essentially as described in U.S. Pat. No. 5,853,733 [e.g. FIG. 8 of U.S. Pat. No. 5,853,733; redrawn, at least in part, in FIG. 1, herein]. To allow integration into the US region of the FC126 HVT genome, the region covered by the cosmid nr. 378-50 in U.S. Pat. No. 5,853,733, was now provided from three smaller plasmids: pSY640 and 556-60.6, and one transfer plasmid (228509-ILT-435Vec6), overlapping these two, and containing the IBDV/ILTV expression cassettes in the US2 gene locus. The set of seven linearized constructs: 3 cosmids and 4 plasmids are transfected all together into CEFs, using a standard $CaCl_2$ transfection protocol and the resulting virus stock was plaque purified two times.

Construction of HVT/ILT/IBDV 1386-48.1.1.1: [see, 1386-48 depicted in FIG. 2]

The cosmid regeneration of HVT/ILT/IBDV 1386-48.1.1.1 was performed essentially as described in U.S. Pat. No. 5,853,733 [e.g. FIG. 8 of U.S. Pat. No. 5,853,733; redrawn, at least in part, in FIG. 1, herein]. To allow integration into the US region of the FC126 HVT genome, the region covered by the cosmid nr. 378-50 in U.S. Pat. No. 5,853,733, was now provided from three smaller plasmids: pSY640 and 556-60.6, and one transfer plasmid (1333-85.B6), overlapping these two, and containing the IBDV/I LTV expression cassettes in the US2 gene locus. The set of seven linearized constructs: 3 cosmids and 4 plasmids are transfected all together into CEFs, using a standard $CaCl_2$ transfection protocol and the resulting virus stock was plaque purified two times.

Construction of HVT/ILT/IBDV 1386-48.3.1.7: [see, 1386-48 depicted in FIG. 2]

The cosmid regeneration of HVT/ILT/IBDV 1386-48.3.1.7 was performed essentially as described in U.S. Pat. No. 5,853,733 [e.g. FIG. 8 of U.S. Pat. No. 5,853,733; redrawn, at least in part, in FIG. 1, herein]. To allow integration into the US region of the FC126 HVT genome, the region covered by the cosmid nr. 378-50 in U.S. Pat. No. 5,853,733, was now provided from three smaller plasmids: pSY640 and 556-60.6, and one transfer plasmid (1386-04.4#1), overlapping these two, and containing the IBDV/ILTV expression cassettes in the US2 gene locus. The set of seven linearized constructs: 3 cosmids and 4 plasmids are transfected all together into CEFs, using a standard $CaCl_2$ transfection protocol and the resulting virus stock was plaque purified two times.

Construction of HVT/ILT/IBDV 484: [see, 1386-484 depicted in FIG. 2]

The cosmid regeneration of HVT/ILT/IBDV 484 was performed essentially as described in U.S. Pat. No. 5,853,733 [e.g. FIG. 8 of U.S. Pat. No. 5,853,733; redrawn, at least in part, in FIG. 1, herein]. To allow integration into the UL54.5 region of the FC126 HVT genome, the region covered by the cosmid nr. 407-32.1C1 in U.S. Pat. No. 5,853,733, was now provided from three smaller plasmids: 672-01.A40 and 672-07.C40, and one transfer plasmid (484-1050-2641-10859), overlapping these two, and containing the IBDV/ILTV expression cassettes in the UL54.5 gene locus. The set of seven linearized constructs: 4 cosmids and 3 plasmids are transfected all together into CEFs, using a standard $CaCl_2$ transfection protocol and the resulting virus stock was plaque purified two times.

Description of Subgenomic Fragments for Generating FC126 HVT:

Subgenomic Clone 407-32.2C3

Cosmid 407-32.2C3 contains an approximately 40,170 base pair region of genomic HVT DNA [Left terminus—pos. 39,754; Afonso et al., 2001, supra; Acc. #AF291866]. This region includes HVT BamHI fragments F', L, P, N1, E, D, and 2,092 base pairs of fragment B.

Subgenomic Clone 172-07.BA2

Plasmid 172-07.BA2 contains a 25,931 base pair region of genomic HVT DNA. It was constructed by cloning the HVT BamHI B fragment [pos. 37,663 to 63,593; Afonso et al., 2001, supra; Acc. #AF291866], into the plasmid pSP64 (Promega, Madison Wis.).

Subgenomic Clone 407-32.5G6

Cosmid 407-32.5G6 contains a 39,404 base pair region of genomic HVT DNA [pos. 61,852-101,255; Afonso et al., 2001, supra; Acc. #AF291866]. This region includes HVT BamHI fragments H, C, Q, K1, M, K2, plus 1,742 base pairs of fragment B, and 3,880 base pairs of fragment J. Subgenomic Clone 407-31.

1C1Cosmid 407-31.1C1 contains a 37,444 base pair region of genomic HVT DNA [pos. 96,095-133,538; Afonso et al., 2001, supra; Acc. #AF291866]. This region includes HVT BamHI fragments J, G, I, F, O, plus 1,281 base pairs of fragment K2, and 6,691 base pairs of fragment A.

Subgenomic Clone 378-50

Cosmid 378-50 contains a 28,897 base pair region of genomic HVT DNA [see, FIG. 8 of U.S. Pat. No. 5,853,733; redrawn, at least in part, in FIG. 1, herein]. This region includes HVT BamHI fragment A. It was constructed by cloning the HVT BamHI A fragment [pos. 126,848-155,744; Afonso et al., 2001, supra; Acc. #AF291866] into cosmid pWE15.

Additional Insertion Fragments for Generating HVT/ILT/IBDV 1386-134.1-2:

Subgenomic Clone 228059-ILT-435Vec6

The insertion plasmid 228059-ILT-435Vec6 contains a 7311 base pair EcoRI fragment of the HVT unique short regions [pos. 126880-144190; Afonso et al., 2001, supra; Acc. #AF291866], cloned into the plasmid pSP64 (Promega, Madison, Wis.). Inserted into a unique StuI site within the HVT US2 gene [pos. 140540/140541; Afonso et al., 2001, supra; Acc. #AF291866, between amino acid residues 124 and 125] are 2 elements: an expression cassette consisting of the mCMV IE promoter, the IBDV classic type F52/70, Faragher strain, virus protein 2 gene (VP2), and the SV40 polyadenylation signal, followed by a 3563 base pair SalI-HindIII fragment from ILTV, NVSL Challenge Strain, Lot #83-2 [pos. 10532-14094; Wild et al., Virus Genes 12:104-116 (1996); Acc. #U28832], encoding the full length genes for glycoprotein D (gD) and glycoprotein I (gI), plus partial coding regions from glycoprotein E (amino acids 1-101), and ORF5 (amino acids 734-985). The IBDV VP2, ILTV gD and ILTV gI genes are transcribed in the opposite direction relative to the HVT US2 gene.

Subgenomic Clone pSY640

Plasmid pSY640 contains an approximately 13,600 base pair region of genomic HVT DNA (pos. 126848-140540; Afonso et al., 2001, supra; Acc. #AF291866] derived from BamHI fragment A. To generate this plasmid the region of DNA located upstream of the US2 gene, beginning at the StuI site located in the US2 gene and continuing to the end of the BamHI A fragment, was cloned into the plasmid pSP64 (Promega, Madison Wis.).

Subgenomic Clone 556-60.6

Plasmid 556-60.6 contains an approximately 12,500 base pair region of genomic HVT DNA derived from BamHI fragment A (approximate pos. 143300-155744; Afonso et al., 2001, supra; Acc. #AF291866]. To generate this plasmid, the region of DNA located downstream of the US2 gene (beginning at the StuI site located in the US2 gene and continuing to the end of the BamHI A fragment) was cloned into pSP64 (Promega, Madison Wis.), and then treated with exonuclease to "chewed back" from StuI site ~150 bp, and re-cloned into pBR322 plasmid vector.

Additional Insertion Fragments for Generating HVT/ILT/IBDV 1386-48.1.1.1:

Subgenomic Clone 1333-85.86

The insertion plasmid 1333-85.B6 contains a 7311 base pair EcoRI fragment of the HVT unique short regions [pos. 126880-144190; Afonso et al., 2001, supra; Acc. #AF291866], cloned into the plasmid pSP64 (Promega, Madison, Wis.). Inserted into a unique StuI site within the HVT US2 gene [pos. 140540/140541; Afonso et al., 2001, supra; Acc. #AF291866, between amino acid residues 124 and 125] are 2 elements: a 3563 base pair SalI-HindIII fragment from ILTV, NVSL Challenge Strain, Lot #83-2 [pos. 10532-14094; Wild et al., *Virus Genes* 12:104-116 (1996); Acc. #U28832], encoding the full length genes for glycoprotein D (gD) and glycoprotein I (gI), plus partial coding regions from glycoprotein E (amino acids 1-101), and ORF5 (amino acids 734-985) and an expression cassette consisting of the chicken β-Actin promoter, the IBDV classic type F52/70, Faragher strain, virus protein 2 gene (VP2), and the polyadenylation signal from the Feline Herpesvirus (FHV) glycoprotein B gene. The ILTV gD, ILTV gI and IBDV VP2 genes are transcribed in the opposite direction relative to the HVT US2 gene.

Subgenomic Clone pSY640.

Plasmid pSY640 contains an approximately 13,600 base pair region of genomic HVT DNA (pos. 126848-140540; Afonso et al., 2001, supra; Acc. #AF291866] derived from BamHI fragment A. To generate this plasmid the region of DNA located upstream of the US2 gene, beginning at the StuI site located in the US2 gene and continuing to the end of the BamHI A fragment, was cloned into the plasmid pSP64 (Promega, Madison Wis.).

Subgenomic Clone 556-60.6.

Plasmid 556-60.6 contains an approximately 12,500 base pair region of genomic HVT DNA derived from BamHI fragment A (approximate pos. 143300-155744; Afonso et al., 2001, supra; Acc. #AF291866]. To generate this plasmid, the region of DNA located downstream of the US2 gene (beginning at the StuI site located in the US2 gene and continuing to the end of the BamHI A fragment) was cloned into pSP64 (Promega, Madison Wis.), and then treated with exonuclease to "chewed back" from StuI site ~150 bp, and re-cloned into pBR322 plasmid vector.

Additional Insertion Fragments for Generating HVT/ILT/IBDV 1386-48.3.1.7:

Subgenomic Clone 1386-04.4#1

The insertion plasmid 1386-04.4#1 contains a 7311 base pair EcoRI fragment of the HVT unique short regions [pos. 126880-144190; Afonso et al., 2001, supra; Acc. #AF291866], cloned into the plasmid pSP64 (Promega, Madison, Wis.). Inserted into a unique StuI site within the HVT US2 gene [pos. 140540/140541; Afonso et al., 2001, supra; Acc. #AF291866, between amino acid residues 124 and 125] are 2 elements: a 3563 base pair SalI-HindIII fragment from ILTV, NVSL Challenge Strain, Lot #83-2 [pos. 10532-14094; Wild et al., Virus Genes 12:104-116 (1996); Acc. #U28832], encoding the full length genes for glycoprotein D (gD) and glycoprotein I (gI), plus partial coding regions from glycoprotein E (amino acids 1-101), and ORF5 (amino acids 734-985) and an expression cassette consisting of the hCMV IE promoter, the IBDV classic type F52/70, Faragher strain, virus protein 2 gene (VP2), and the polyadenylation signal from the Herpes Simplex virus (HSV) thymidine kinase gene. The ILTV gD, ILTV gI, and IBDV VP2 genes are transcribed in the opposite direction relative to the HVT US2 gene.

Subgenomic Clone pSY640.

Plasmid pSY640 contains an approximately 13,600 base pair region of genomic HVT DNA (pos. 126848-140540; Afonso et al., 2001, supra; Acc. #AF291866] derived from BamHI fragment A. To generate this plasmid the region of DNA located upstream of the US2 gene, beginning at the StuI site located in the US2 gene and continuing to the end of the BamHI A fragment, was cloned into the plasmid pSP64 (Promega, Madison Wis.).

Subgenomic Clone 556-60.6.

Plasmid 556-60.6 contains an approximately 12,500 base pair region of genomic HVT DNA derived from BamHI fragment A (approximate pos. 143300-155744; Afonso et al., 2001, supra; Acc. #AF291866]. To generate this plasmid, the region of DNA located downstream of the US2 gene (beginning at the StuI site located in the US2 gene and continuing to the end of the BamHI A fragment) was cloned into pSP64 (Promega, Madison Wis.), and then treated with exonuclease to "chewed back" from StuI site ~150 bp, and re-cloned into pBR322 plasmid vector.

Additional Insertion Fragments for Generating HVT/ILT/IBDV 484:

Subgenomic Clone 484-1050-2641-10859

The insertion plasmid 484-1050-2641-10859 contains a 8636 base pair region of genomic HVT unique long region [pos. 109489-118124; Afonso et al., 2001, supra; Acc. #AF291866], cloned into a derivative of plasmid pNEB193 (deleted AatII-PvuII). It is flanked by AscI sites and includes HVT BamHI fragments I, S, plus 1337 base pairs of fragment G and 1177 base pairs of fragment F. Inserted into an XhoI site within the HVT UL54.5 open reading frame [pos. 111240/111241; Afonso et al., 2001, supra; Acc. #AF291866, between amino acid residues 21 and 22] are 2 elements: an expression cassette consisting of the mCMV IE promoter, the IBDV classic type F52/70, Faragher strain, virus protein 2 gene (VP2), and the SV40 polyadenylation signal, followed by a 3563 base pair SalI-HindIII fragment from ILTV, NVSL Challenge Strain, Lot #83-2 [pos. 10532-14094; Wild et al., Virus Genes 12:104-116 (1996); Acc. #U28832], encoding the full length genes for glycoprotein D (gD) and glycoprotein I (gI), plus partial coding regions from glycoprotein E (amino acids 1-101), and ORF5 (amino acids 734-985). The IBDV VP2, ILTV gD, and ILTV gI genes are transcribed in the opposite direction relative to the HVT UL54.5 gene.

Subgenomic Clone 672-01.A40

Plasmid 672-01.A40 contains a 14,731 base pair region of genomic HVT DNA derived from the unique long region [pos. 96095-110825; Afonso et al., 2001, supra; Acc. #AF291866], cloned into a derivative of plasmid pNEB193. This region includes HVT BamHI fragments G, J and 1281 base pairs of K2.

Subgenomic clone 672-07.C40

Plasmid 672-07.C40 contains a 12,520 base pair region of genomic HVT DNA derived from the unique long region [pos. 116948-129467; Afonso et al., 2001, supra; Acc.

#AF291866], cloned into a derivative of plasmid pNEB193. This region includes HVT BamHI fragments F, O and 2620 base pairs of A.

Standard $CaCl_2$ Transfection Protocol

Secondary CEF's are seeded on 6 well culture plates and incubated at 38° C. with 5% $CO_2$ for 24 hours and confluent monolayers form. For each well a total amount of 0.5 μg DNA of cosmids and plasmids were mixed in Hepes buffer and 125 mM $CaCl_2$ was added dropwise until precipitation was imminent. This mixture was added to the CEF cell monolayer, and incubated for 2 to 3 hours. Supernatant was removed and an overlay of 15% Glycerol was added, and kept on the cells for 1 minute. Then this was removed, washed with PBS, and fresh culture medium was added and cells were incubated for 5 days. Next, cells were harvested by trypsinization and cells from individual plates were each seeded on fresh monolayers of CEF cells in 10 cm plates and incubated until 50-90% CPE was achieved. Next, the amplified transfected cells were harvested by trypsinization, and dilutions of $10^{-2}$ to $10^{-4}$ were plated on 10 cm plates with CEF monolayers and incubated. The following day, the plates were covered with agar, and a number of individual plaques of HVT/ILTV/IBDV were isolated and amplified on CEFs. Each virus stock was plaque purified a second time by infecting confluent monolayers of CEFs on 10 cm plates with first round purified stocks diluted to $10^{-2}$ to $10^{-4}$ and incubating cells. The following day, the plates were covered with agar, and a number of individual plaques of HVT/ILTV/IBDV were isolated and amplified on CEFs.

Example 3

Recombinant HVT/ILTV/IBDV Virus Stocks are Phenotypically Stable for Expression of the ILT and IBDV Proteins Following Serial Passage in Tissue Culture Three constructs, one comprising HVT/IBDV/ILT 1386-134.1-2, the second, comprising HVT/ILT/IBDV 1386-48.1.1.1, and the third comprising HVT/ILT/IBDV 1386-48.3.1.7 were serial passaged greater than 14 times on secondary CEF cells and evaluated for expression of the inserted ILTV and IBDV genes in an Immunofluorescence Assay. A fourth construct, designated HVT/ILT/IBDV 484.1-1A3A3 was serial passaged greater than 15 times on secondary CEF cells and evaluated for expression of the inserted ILTV and IBDV genes in an Immunofluorescence Assay, [see, Tables 1 and 2 below].

Generation of Tissue Culture Passage Stocks:

For each tissue culture passage, confluent secondary CEF monolayers, plated on a 10 cm dish were inoculated with 50-100 μL of virus stock, then incubated at 38° C., 5% $CO_2$ for 2-5 days until CPE was evident. Next, cells were harvested by trypsinization, passage 1 (P1). The process was repeated to prepare further passage stocks (P2-P15).

Phenotypic Stability Analysis:

Six well plates were planted with secondary CEF monolayers. The cells were inoculated with virus stocks harvested at various passage levels: P0-P15, or diluent alone. Plates were inoculated at multiple dilutions to achieve a countable number of plaques per well, and incubated at 38° C., 5% $CO_2$. After a five day incubation, supernatant was decanted and CEF monolayers were fixed with 100% methanol for 10-15 minutes at 15-30° C. Methanol was decanted and cells allowed to air dry prior to staining with ILTV gD (MAB #6), ILTV gI (polyclonal Rabbit anti-gI), and IBDV VP2 (MCA GDV-R63) primary antibodies. Following a 2 hour blocking step, (5% non-fat dry milk in PBS), 2 mL per well, was added to dishes, and incubated on a rocking platform at 15-30° C., primary antibodies were diluted as appropriate and added at 2 mL per well, then incubated at 15-30° C. for 3 hours on a rocking platform. After antibody incubation, plates were washed three times with PBS. The FITC-labeled secondary antibody solution (Rabbit anti-mouse or Goat anti-rabbit) was prepared at 1:100 and 2 mL was added to each well. Plates were incubated for 1 hour at 15-30° C. on a rocking platform. Following the incubation, the plates were washed three times with PBS, and examined under a fluorescent scope. Plaques stained with the ILT antibodies were observed for positive (+) or negative (−) fluorescence. Fluorescing plaques stained with primary antibody to IBDV VP2 protein were counted. Plates were then examined under a white light microscope and the plaques were re-counted. The percentage of fluorescing plaques at each passage level is provided in Tables 1 and 2 below, as well as a qualitative determination of the IBDV VP2 protein expression and vector stability.

TABLE 1

STABILITY OF EXPRESSION FOLLOWING PASSAGE IN TISSUE CULTURE

| | | | | Expression | | |
|---|---|---|---|---|---|---|
| Virus Number | Description | Insertion site | Passage Level | ILT gD | ILT gI | IBDV VP2 |
| 1386-48.3.1.7 | (h)IE-VP2/ ILTgDgI | US2 | P0 | + | + | 100% |
| | | | P5 | + | + | 100% |
| | | | P9 | + | + | 100% |
| | | | P14 | + | + | 96% |
| 1386-48.1.1.1 | (c)β-act-VP2/ ILTgDgI | US2 | P0 | + | + | 100% |
| | | | P5 | + | + | 100% |
| | | | P10 | + | + | 97% |
| | | | P15 | + | + | 98% |
| 1386-134.1-2 | (m)IE-VP2/ ILTgDgI | US2 | P0 | + | + | 100% |
| | | | P5 | + | + | 100% |
| | | | P10 | + | + | 98% |
| | | | P15 | + | + | 99% |
| 484.1-1A3A3 | (m)IE-VP2/ ILTgDgI | UL54.5 | P0 | + | + | 100% |
| | | | P4 | + | + | 100% |
| | | | P10 | + | + | 97% |
| | | | P15 | + | + | 94% |

TABLE 2

INSERTION PLASMID DESCRIPTION/VECTOR PROPERITES

| Name/ Designation | Insert. site | Insert. Plasmid | IBDV Promoter | IBDV Expression | Stability |
|---|---|---|---|---|---|
| HVT/ILT/IBDV 1386-48.1.1.1 | US2 | 1333-85.B6 | chicken β-actin | Strong | Stable |
| HVT/ILT/IBDV 1386-48.3.1.7 | US2 | 1386-04.4#1 | hCMV IE | Strong | Stable |

TABLE 2-continued

| INSERTION PLASMID DESCRIPTION/VECTOR PROPERITES | | | | | |
|---|---|---|---|---|---|
| Name/ Designation | Insert. site | Insert. Plasmid | IBDV Promoter | IBDV Expression | Stability |
| HVT/IBDV/ILT 1386-134.1-2 | US2 | 228509-ILT-435Vec6 | mCMV IE | Strong | Stable |
| HVT/IBDV/ILT 484 | UL54.5 | 484-1050-2641-10859 | mCMV IE | Strong | Stable |

Example 4

Recombinant HVT/ILTV/IBDV Virus Stocks are Phenotypically Stable for Expression of the ILT and IBDV Proteins Following Vaccination and Recovery from Birds Three vaccines, one comprising HVT/ILT/IBDV 1386-134.1-2, another comprising HVT/ILT IBDV 1386-48.3.1.7, and a third comprising HVT/ILT/IBDV 484.1-1A3A3 were used to inoculate three groups of fifteen (15) day-of-age chickens by the subcutantious route. A fourth group of birds were vaccinated with diluent alone to serve as a negative control group. Spleen samples were collected seven days post-inoculation, and processed for virus isolation on chicken embryo fibroblast cells. Inoculated cells were passaged two times to allow expansion of any virus present. When cytopathic effect was clearly visible, monolayers were harvested and stock frozen. These stocks were used to inoculate secondary CEFs, and plaques analyzed for expression of the ILTV gD, ILTV gI, and IBDV VP2 proteins by immunofluorescence assay (IFA) assay, with antibodies specific to each protein.

Phenotypic Stability Analysis

Six well plates were planted with secondary CEF monolayers. The cells were inoculated with the harvested virus isolation stocks or diluent alone. The plates were inoculated at multiple dilutions to achieve a countable number of plaques per well, and incubated at 38° C., 5% $CO_2$. After five days incubation, supernatant was decanted and CEF monolayers were fixed with 100% methanol for 10-15 minutes at 15-30° C. Methanol was decanted and cells allowed to air dry prior to staining with ILTV gD (MAB #6), ILTV gI(polyclonal Rabbit anti-gI), and IBDV VP2 (MCA GDV-R63) primary antibodies. Following a 2 hour blocking step, (5% non-fat dry milk in PBS), 2 mL per well, was added to dishes, and incubated on a rocking platform at 15-30° C., primary antibodies were diluted as appropriate, and added at 2 mL per well, then incubated at 15-30° C. for 3 hours on a rocking platform. After antibody incubation, plates were washed three times with PBS. The FITC-labeled secondary antibody solution (Rabbit anti-mouse or Goat anti-rabbit) was prepared at 1:100 and 2 mL was added to each well. Plates were incubated for 1 hour at 15-30° C. on a rocking platform. Following incubation, plates were washed three times with PBS, and examined under a fluorescent scope. Plaques stained with the ILTV antibodies were observed for positive (+) or negative (−) fluorescence. Fluorescing plaques stained with primary antibody to IBDV VP2 were counted. Plates were then examined under a white light microscope and plaques re-counted. The percentage of fluorescing plaques at each passage level is provided in Table 3A below. This study was essentially repeated except the virus was recovered two weeks post-inoculation, see, Table 3B below.

TABLE 3A

| STABILITY OF EXPRESSION FOLLOWING PASSAGE IN BIRDS | | | | | | |
|---|---|---|---|---|---|---|
| | | | | Percent Expressing | | |
| Vaccine | Insert Description | Insertion site | Dose (PFU) | ILT gI | ILT gD | IBDV VP2 |
| HVT/ILT/IBDV 1386-134.1-2 (p10) | (m)IE-VP2/ ILTgDgI | US2 | 7737 | 100% | 100% | 90% |
| HVT/ILT/IBDV 1386-48.3.1.7 (p10) | (h)IE-VP2/ ILTgDgI | US2 | 7003 | 100% | 100% | 89% |
| HVT/IBDV/ILT 484.1-1A3A3 (p10) | (m)IE-VP2/ ILTgDgI | UL54.5 | 7793 | 100% | 100% | 97% |
| Diluent | NA | NA | 0 | NA | NA | NA |

TABLE 3B

| VIRUS RECOVERED 2 WEEKS POST-INOCULATION | | | | | | |
|---|---|---|---|---|---|---|
| | | | | Percent Expressing | | |
| Vaccine | Insert Description | Insertion site | Dose (PFU) | ILT gI | ILT gD | IBDV VP2 |
| HVT/ILT/IBDV 1386-48.1.1.1 (p10) | (h)IE-VP2/ ILTgDgI | US2 | 4785 | 100% | 92% | 42% |

Example 5

Unsuccessful Constructs

The recombinant vector vaccine viruses, by definition are engineered to carry and express foreign genes. Should transcription and expression of these foreign genes provide a growth disadvantage to the recombinant virus relative to the parental virus, it is possible for these genes to be lost during production of the vaccine. For this reason, vaccine candidates must be tested for both genetic and phenotypic stability.

In addition, the protection criteria used is that which has been established by the USDA and codified in the Title 9 Code of Federal Regulations, part 113 (9CFR 113) «Standard requirements for Animal Products». Live virus vaccines must provide at least 90% protection, in the case of NDV, IBDV and ILTV, and at least 80% in the case of MDV, from clinical signs or lesions associated with the disease to obtain a license.

Genetic stability of the viral constructs was determined by Southern blot analysis after a defined number of passages in tissue culture, the highest anticipated vaccine production level, and compared with DNA from the original isolate. DNA extracted from viral stocks would be digested with restriction enzymes, transfered to a membrane and hybridized with probes designed to detect the presence of the inserted foreign genes. Genetic stability may also be determined by PCR analysis. PCR primers designed to anneal to DNA within or flanking the foreign DNA could be used to amplify fragments of a known size from the viral DNA templates both before and after passage in tissue culture.

Phenotypic stability of the viral constructs was determined by immunological staining of individual viral plaques with antibodies directed against the protein products of these inserted foreign genes. Protection provided by these recombinant vaccines relies on expression of these protein products in order to stimulate the animals immune system. In most cases, if the percent of viruses staining positive for the foreign protein expression dropped below 90%, it was likely detrimental to the viruses ability to be grown in tissue culture, and therefore unsuitable as a vaccine candidate.

As is readily apparent from Tables 4A and 4B below, most rMDVnp constructs do not meet these two criteria, namely stabilty with relatively strong antigen expression and/or efficacy. Table 4A provides a series of recombinant HVT constructs with multiple heterologous inserts in which one of the heterologous inserts encodes an IBDV antigen. As the results show, all of the constructs in Table 4A failed to meet the stability with relatively strong antigen expression and/or efficacy criteria.

TABLE 4A

DOUBLE RECOMBINANT HVT AND IBDV VIRUS CONSTRUCTS:

| Name/ Designation | Insertion site | Insert | IBDV Promoter | IBDV Expression | Stability |
|---|---|---|---|---|---|
| HVT 003 | UL43 | [IBDV] polyprotein<br>[*Ecoli*] Bgal | PRV gX | Poor | stable |
| HVT 016 | UL43 | [IBDV] VP2<br>[*Ecoli*] Bgal | hCMV IE | Strong | unstable |
| HVT 056 | US2 | [MDV] gA, gB<br>[IBDV] VP2 | hCMV IE | Strong | Unstable |
| HVT 060 | US2 | [MDV] gA, gB<br>[IBDV] VP2,<br>16 kD ORF | IE-VP2,<br>gX-16dk<br>ORF | Strong | unstable |
| HVT 137 | US2<br>UL54.5 | [MDV] gA, gB, gC<br>[IBDV] VP2 | [BHV] VP8<br>(tegument) | Poor | stable |
| HVT 143 | US2<br>US2<br>UL54.5 | [MDV] gA, gB, gD<br>[NDV] HN, F<br>[IBDV] VP2 | [BHV] VP8<br>(tegument) | Poor | Unstable |
| HVT/NDV/IBDV<br>1312-92 | US2<br>UL7/UL8 | [IBDV] VP2<br>[NDV] F | hCMV IE | Strong | Unstable |
| HVT/NDV/IBDV<br>1312-94 | US2<br>UL7/UL8 | [IBDV] VP2<br>[NDV] F | hCMV IE | Strong | Unstable |
| HVT/NDV/IBDV<br>1312-95 | US2<br>UL7/UL8 | [IBDV] VP2<br>[NDV] F | hCMV IE | Strong | Unstable |
| HVT/NDV/IBDV<br>1329-54 | US2 | [IBDV] VP2<br>[NDV] F | FHV gB | Strong | Unstable |

Table 4B below, provides a series of eleven recombinant HVT constructs and one lone NAHV construct each of which comprise multiple heterologous inserts in which at least one of the heterologous inserts encodes either an NDV or an ILTV antigen.[1] As the results show, all of the constructs in Table 4B failed to meet the stability with relatively strong antigen expression and/or efficacy criteria.

The data in Table 4B was submitted to the U.S. Patent Office during the prosecution of U.S. Pat. No. 8,932,604 B2 in a Declaration signed by one of the co-Inventors of the present application.

TABLE 4B

DOUBLE RECOMBINANT HVT AND NAHV VIRUS CONSTRUCTS:

| Name | Insertion site | Insert | Stability | NDV Protection | MDV Protection | ILT Protection |
|---|---|---|---|---|---|---|
| HVT 048 | US2 | [MDV] gA, gB<br>[NDV] F | Stable | Good | *Protective | — |
| HVT 049 | US2 | [MDV] gA, gB<br>[NDV] HN | Stable | Poor<br>(<20%) | Not tested | — |

TABLE 4B-continued

| DOUBLE RECOMBINANT HVT AND NAHV VIRUS CONSTRUCTS: | | | | | | |
|---|---|---|---|---|---|---|
| Name | Insertion site | Insert | Stability | NDV Protection | MDV Protection | ILT Protection |
| HVT 050 | US2 | [MDV] gA, gB [NDV] F, HN | Stable | Good | *Protective | — |
| HVT 053 | US2 | [MDV] gA, gB [ILT] gB, gD | Unstable | — | Not tested | None |
| HVT 078 | US2 | [MDV] gA, gB, gD [NDV]HN, F | Unstable | Not tested | Not tested | — |
| HVT 079 | US2 | [MDV] gA, gB, gD [ILT] gB, gD | Unstable | — | Not tested | (71-100%) |
| HVT 106 | US2 | [MDV]gA, gB, gD [NDV]HN, F | Stable | **Unknown | Not tested | — |
| HVT 123 | UL54.5 + US2 | [ILT] gD, gB/UL54.5 [MDV] gA, gD, gB/US2 | Unstable | — | Not tested | Not tested |
| HVT 125 | UL54.5 + US2 | [ILT] gDgI, gB/UL54.5 [MDV] gA, gD, gB/US2 | Unstable | — | Not tested | Not tested |
| HVT 128 | UL54.5 + US2 | [NDV] HN, F/UL54.5 [MDV] gA, gD, gB/US2 | Unstable | Not tested | Not tested | — |
| HVT 139 | UL54.5 + US2 | [ILT] gDgI/UL54.5 [MDV] gA, gD, gB/US2 | Unstable | — | Not tested | Not tested |
| HVY-198 (NAHV) | US2* (MDV) | [NDV] F + [ILT] gD, gI | Unstable | | | |

* Protective, but subsequently failed in field studies
** Only 75% birds seroconverted to NDV F Example 6

Sequences

The following sequences have been used in the exemplary rHVT constructs. The coding sequences provided below include individual stop codons, which can be readily replaced with alternative stop codons without modifying the properties of the protein antigens that the coding sequences encode.

SEQ ID NO 1: ILTV gD Glycoprotein (1134 bp)

```
atggaccgccatttatttttgaggaatgctttttg
gactatcgtactgctttcttccttcgctagccaga
gcaccgccgccgtcacgtacgactacattttaggc
cgtcgcgcgctcgacgcgctaaccataccggcggt
tggcccgtataacagatacctcactagggtatcaa
gaggctgcgacgttgtcgagctcaacccgatttct
aacgtggacgacatgatatcggcggccaaagaaaa
agagaaggggggccctttcgaggcctccgtcgtct
ggttctacgtgattaagggcgacgacggcgaggac
aagtactgtccaatctatagaaaagagtacaggga
atgtggcgacgtacaactgctatctgaatgcgccg
ttcaatctgcacagatgtgggcagtggactatgtt
cctagcacccttgtatcgcgaaatggcgcgggact
gactatattctcccccactgctgcgctctctggcc
aatacttgctgaccctgaaaatcgggagatttgcg
caaacagctctcgtaactctagaagttaacgatcg
ctgtttaaagatcgggtcgcagcttaactttttac
```

-continued

```
cgtcgaaatgctggacaacagaacagtatcagact
ggatttcaaggcgaacacctttatccgatcgcaga
caccaatacacgacacgcggacgacgtatatcggg
gatacgaagatattctgcagcgctggaataatttg
ctgaggaaaaagaatcctagcgcgccagaccctcg
tccagatagcgtcccgcaagaaattcccgctgtaa
ccaagaaagcggaagggcgcaccccggacgcagaa
agcagcgaaaagaaggcccctccagaagactcgga
ggacgacatgcaggcagaggcttctggagaaaatc
ctgccgccctccccgaagacgacgaagtccccgag
gacaccgagcacgatgatccaaactcggatcctga
ctattacaatgacatgcccgccgtgatcccggtgg
aggagactactaaaagttctaatgccgtctccatg
cccatattcgcggcgttcgtagcctgcgcggtcgc
gctcgtggggctactggtttggagcatcgtaaaat
gcgcgcgtagctaa
```

SEQ ID NO 2: ILTV gD Glycoprotein (377 amino acids)

```
MDRHLFLRNAFWTIVLLSSFASQSTAAVTYDYILG
RRALDALTIPAVGPYNRYLTRVSRGCDVVELNPIS
NVDDMISAAKEKEKGGPFEASVVWFYVIKGDDGED
KYCPIYRKEYRECGDVQLLSECAVQSAQMWAVDYV
PSTLVSRNGAGLTIFSPTAALSGQYLLTLKIGRFA
QTALVTLEVNDRCLKIGSQLNFLPSKCWTTEQYQT
GFQGEHLYPIADTNTRHADDVYRGYEDILQRWNNL
```

-continued

LRKKNPSAPDPRPDSVPQEIPAVTKKAEGRTPDAE

SSEKKAPPEDSEDDMQAEASGENPAALPEDDEVPE

DTEHDDPNSDPDYYNDMPAVIPVEETTKSSNAVSM

PIFAAFVACAVALVGLLVWSIVKCARS

SEQ ID NO 3: ILTV gl Glycoprotein (1089 bp)
Atggcatcgctacttggaactctggctctccttgc cgcgacgctcgcacccttcggcgcgatgggaatcg tgatcactggaaatcacgtctccgccaggattgac gacgatcacatcgtgatcgtcgcgcctcgccccga agctacaattcaactgcagctatttttcatgcctg gccagagaccccacaaaccctactcaggaaccgtc cgcgtcgcgtttcggtctgatataacaaaccagtg ctaccaggaacttagcgaggagcgctttgaaaatt gcactcatcgatcgtcttctgtttttgtcggctgt aaagtgaccgagtacacgttctccgcctcgaacag actaaccggacctccacacccgtttaagctcacta tacgaaatcctcgtccgaacgacagcgggatgttc tacgtaattgttcggctagacgacaccaaagaacc cattgacgtcttcgcgatccaactatcggtgtatc aattcgcgaacaccgccgcgactcgcggactctat tccaaggcttcgtgtcgcaccttcggattacctac cgtccaacttgaggcctatctcaggaccgaggaaa gttggcgcaactggcaagcgtacgttgccacggag gccacgacgaccagcgccgaggcgacaaccccgac gcccgtcactgcaaccagcgcctccgaacttgaag cggaacactttacctttccctggctagaaaatggc gtggatcattacgaaccgacacccgcaaacgaaaa ttcaaacgttactgtccgtctcgggacaatgagcc ctacgctaattggggtaaccgtggctgccgtcgtg agcgcaacgatcggcctcgtcattgtaatttccat cgtcaccagaaacatgtgcaccccgcaccgaaaat tagacacggtctcgcaagacgacgaagaacgttcc caaactagaagggaatcgcgaaaatttggacccat ggttgcgtgcgaaataaacaagggggctgaccagg atagtgaacttgtggaactggttgcgattgttaac ccgtctgcgctaagctcgcccgactcaataaaaat gtga -continued SEQ ID NO 4: ILTV gl Glycoprotein (362 amino acids)
MASLLGTLALLAATLAPFGAMGIVITGNHVSARID

DDHIVIVAPRPEATIQLQLFFMPGQRPHKPYSGTV

RVAFRSDITNQCYQELSEERFENCTHRSSSVFVGC

KVTEYTFSASNRLTGPPHPFKLTIRNPRPNDSGMF

YVIVRLDDTKEPIDVFAIQLSVYQFANTAATRGLY

SKASCRTFGLPTVQLEAYLRTEESWRNWQAYVATE

ATTTSAEATTPTPVTATSASELEAEHFTFPWLENG

VDHYEPTPANENSNVTVRLGTMSPTLIGVTVAAVV

SATIGLVIVISIVTRNMCTPHRKLDTVSQDDEERS

QTRRESRKFGPMVACEINKGADQDSELVELVAIVN

PSALSSPDSIKM

SEQ ID NO 5: IBDV VP2 (1362 bp)
atgacaaacctgcaagatcaaacccaacagattgt tccgttcatacggagccttctgatgccaacaaccg gaccggcgtccattccggacgacaccctggagaag cacactctcaggtcagagacctcgacctacaattt gactgtgggggacacagggtcagggctaattgtct tttccctggattccctggctcaattgtgggtgct cactacacactgcagagcaatgggaactacaagtt cgatcagatgctcctgactgcccagaacctaccgg ccagctacaactactgcagactagtgagtcggagt ctcacagtgaggtcaagcacactccctggtggcgt ttatgcactaaacggcaccataaacgccgtgacct tccaaggaagcctgagtgaactgacagatgttagc tacaatgggttgatgtctgcaacagccaacatcaa cgacaaaattgggaatgtcctggtaggggaagggg tcactgtcctcagcctacccacatcatatgatctt gggtatgtgaggcttggtgaccccattcccgctat agggcttgacccaaaaatggtagctacatgcgaca gcagtgacaggcccagagtctacaccataactgca gccgatgattaccaattctcatcacagtaccaacc aggtggggtaacaatcacactgttctcagccaaca ttgatgctatcacaagcctcagcattgggggagag ctcgtgtttcaaacaagcgtccaaggccttgtact gggcgccaccatctaccttataggctttgatggga ctgcggtaatcaccagagctgtggccgcagataat gggctgacggccggcaccgacaatcttatgccatt caatcttgtcattccaaccaatgagataacccagc caatcacatccatcaaactggagatagtgacctcc aaaagtggtggtcaggcaggggatcagatgtcatg -continued gtcggcaagtgggagcctagcagtgacgatccatg gtggcaactatccaggggccctccgtcccgtcaca ctagtagcctacgaaagagtggcaacaggatccgt cgttacggtcgctggggtgagtaacttcgagctga ttccaaatcctgaactagcaaagaacctggttaca gaatacggccgatttgacccaggagccatgaacta cacaaaattgatactgagtgagagggaccgtcttg gcatcaagaccgtctggccaacaagggagtacact gattttcgtgagtacttcatggaggtggccgacct caactctcccctgaagattgcaggagcatttggct tcaaagacataatccgggctataaggaggtaa SEQ ID NO 6: IBDV VP2
(453 amino acids)
MTNLQDQTQQIVPFIRSLLMPTTGPASIPDDTLEK

HTLRSETSTYNLTVGDTGSGLIVFFPGFPGSIVGA

HYTLQSNGNYKFDQMLLTAQNLPASYNYCRLVSRS

LTVRSSTLPGGVYALNGTINAVTFQGSLSELTDVS

YNGLMSATANINDKIGNVLVGEGVTVLSLPTSYDL

GYVRLGDPIPAIGLDPKMVATCDSSDRPRVYTITA

ADDYQFSSQYQPGGVTITLFSANIDAITSLSIGGE

LVFQTSVQGLVLGATIYLIGFDGTAVITRAVAADN

GLTAGTDNLMPFNLVIPTNEITQPITSIKLEIVTS

KSGGQAGDQMSWSASGSLAVTIHGGNYPGALRPVT

LVAYERVATGSVVTVAGVSNFELIPNPELAKNLVT

EYGRFDPGAMNYTKLILSERDRLGIKTVWPTREYT

DFREYFMEVADLNSPLKIAGAFGFKDIIRAIRR

SEQ ID NO 7: ILTV gD
promoter (527 bp)
aaacagctgtactacagagtaaccgatggaagaac atcggtccagctaatgtgcctgtcgtgcacgagcc attctccggaaccttactgtcttttcgacacgtct cttatagcgagggaaaaagatatcgcgccagagtt atactttacctctgatccgcaaacggcatactgca caataactctgccgtccggcgttgttccgagattc gaatggagccttaataatgtttcactgccggaata tttgacggccacgaccgttgtttcgcataccgctg gccaaagtacagtgtggaagagcagcgcgagagca ggcgaggcgtggatttctggccggggaggcaatat atacgaatgcaccgtcctcatctcagacggcactc gcgttactacgcgaaaggagaggtgcttaacaaac acatggattgcggtggaaaacggtgctgctcaggc gcagctgtattcactcttttctggacttgtgtcag -continued gattatgcgggagcatatctgctttgtacgcaacg ct SEQ ID NO 8: ILTV gl promoter (264 bp)
tgactattacaatgacatgcccgccgtgatcccgg tggaggagactactaaaagttctaatgccgtctcc atgcccatattcgcggcgttcgtagcctgcgcggt cgcgctcgtggggctactggtttggagcatcgtaa aatgcgcgcgtagctaatcgagcctagaataggtg gtttcttcctacatgccacgcctcacgctcataat ataaatcacatggaatagcataccaatgcctattc attgggacgttcgaaaagc SEQ ID NO 9: ILTV insert (3563 bp)
tcgacggcagagtcgcagacgcccctattggacgt caaaattgtagaggtgaagttttcaaacgatggcg aagtaacggcgacttgcgtttccaccgtcaaatct ccctatagggtagaaactaattggaaagtagacct cgtagatgtaatggatgaaatttctgggaacagtc ccgccggggtttttaacagtaatgagaaatggcag aaacagctgtactacagagtaaccgatggaagaac atcggtccagctaatgtgcctgtcgtgcacgagcc attctccggaaccttactgtcttttcgacacgtct cttatagcgagggaaaaagatatcgcgccagagtt atactttacctctgatccgcaaacggcatactgca caataactctgccgtccggcgttgttccgagattc gaatggagccttaataatgtttcactgccggaata tttgacggccacgaccgttgtttcgcataccgctg gccaaagtacagtgtggaagagcagcgcgagagca ggcgaggcgtggatttctggccggggaggcaatat atacgaatgcaccgtcctcatctcagacggcactc gcgttactacgcgaaaggagaggtgcttaacaaac acatggattgcggtggaaaacggtgctgctcaggc gcagctgtattcactcttttctggacttgtgtcag gattatgcgggagcatatctgctttgtacgcaacg ctatggaccgccatttatttttgaggaatgctttt tggactatcgtactgctttcttccttcgctagcca gagcaccgccgccgtcacgtacgactacattttag gccgtcgcgcgctcgacgcgctaaccataccggcg gttggcccgtataacagatacctcactagggtatc aagaggctgcgacgttgtcgagctcaacccgattt ctaacgtggacgacatgatatcggcggccaaagaa aaagagaagggggcccctttcgaggcctccgtcgt -continued ctggttctacgtgattaagggcgacgacggcgagg acaagtactgtccaatctatagaaaagagtacagg gaatgtggcgacgtacaactgctatctgaatgcgc cgttcaatctgcacagatgtgggcagtggactatg ttcctagcacccttgtatcgcgaaatggcgcggga ctgactatattctcccccactgctgcgctctctgg ccaatacttgctgaccctgaaaatcgggagatttg cgcaaacagctctcgtaactctagaagttaacgat cgctgtttaaagatcgggtcgcagcttaacttttt accgtcgaaatgctggacaacagaacagtatcaga ctggatttcaaggcgaacacctttatccgatcgca gacaccaatacacgacacgcggacgacgtatatcg gggatacgaagatattctgcagcgctggaataatt tgctgaggaaaaagaatcctagcgcgccagaccct cgtccagatagcgtcccgcaagaaattcccgctgt aaccaagaaagcggaagggcgcaccccggacgcag aaagcagcgaaaagaaggcccctccagaagactcg gaggacgacatgcaggcagaggcttctggagaaaa tcctgccgccctccccgaagacgacgaagtccccg aggacaccgagcacgatgatccaaactcggatcct gactattacaatgacatgcccgccgtgatcccggt ggaggagactactaaaagttctaatgccgtctcca tgcccatattcgcggcgttcgtagcctgcgcggtc gcgctcgtggggctactggtttggagcatcgtaaa atgcgcgcgtagctaatcgagcctagaataggtgg tttcttcctacatgccacgcctcacgctcataata taaatcacatggaatagcataccaatgcctattca ttgggacgttcgaaaagcatggcatcgctacttgg aactctggctctccttgccgcgacgctcgcaccct tcggcgcgatgggaatcgtgatcactggaaatcac gtctccgccaggattgacgacgatcacatcgtgat cgtcgcgcctcgccccgaagctacaattcaactgc agctatttttcatgcctggccagagaccccacaaa ccctactcaggaaccgtccgcgtcgcgtttcggtc tgatataacaaaccagtgctaccaggaacttagcg aggagcgctttgaaaattgcactcatcgatcgtct tctgtttttgtcggctgtaaagtgaccgagtacac gttctccgcctcgaacagactaaccggacctccac acccgtttaagctcactatacgaaatcctcgtccg aacgacagcgggatgttctacgtaattgttcggct agacgacaccaaagaacccattgacgtcttcgcga -continued tccaactatcggtgtatcaattcgcgaacaccgcc gcgactcgcggactctattccaaggcttcgtgtcg caccttcggattacctaccgtccaacttgaggcct atctcaggaccgaggaaagttggcgcaactggcaa gcgtacgttgccacggaggccacgacgaccagcgc cgaggcgacaaccccgacgcccgtcactgcaacca gcgcctccgaacttgaagcggaacactttaccttt ccctggctagaaaatggcgtggatcattacgaacc gacacccgcaaacgaaaattcaaacgttactgtcc gtctcgggacaatgagccctacgctaattggggta accgtggctgccgtcgtgagcgcaacgatcggcct cgtcattgtaatttccatcgtcaccagaaacatgt gcaccccgcaccgaaaattagacacggtctcgcaa gacgacgaagaacgttcccaaactagaagggaatc gcgaaaatttggacccatggttgcgtgcgaaataa acaagggggctgaccaggatagtgaacttgtggaa ctggttgcgattgttaacccgtctgcgctaagctc gcccgactcaataaaaatgtgattaagtctgaatg tggctctccaatcatttcgattctctaatctccca atcctctcaaaaggggcagtatcggacacggactg ggaggggcgtacacgatagttatatggtacagcag aggcctctgaacacttaggaggagaattcagccgg ggagagcccctgttgagtaggcttgggagcatatt gcaggatgaacatgttagtgatagttctcgcctct tgtcttgcgcgcctaacttttgcgacgcgacacgt cctctttttggaaggcactcaggctgtcctcgggg aagatgatcccagaaacgttccggaagggactgta atcaaatggacaaaagtcctgcggaacgcgtgcaa gatgaaggcggccgatgtctgctcttcgcctaact attgctttcatgatttaatttacgacggaggaaag aaagactgcccgcccgcgggacccctgtctgcaaa cctggtaattttactaaagcgcggcgaa SEQ ID NO 10: mCMV IE promoter (1391 bp)

aactccgcccgttttatgactagaaccaatagttt ttaatgccaaatgcactgaaatcccctaatttgca aagccaaacgcccccctatgtgagtaatacggggac tttttacccaatttcccacgcggaaagccccctaa tacactcatatggcatatgaatcagcacggtcatg cactctaatggcggcccatagggactttccacata gggggcgttcaccatttcccagcataggggtggtg actcaatggcctttacccaagtacattgggtcaat -continued gggaggtaagccaatgggtttttcccattactggc aagcacactgagtcaaatgggactttccactgggt tttgcccaagtacattgggtcaatgggaggtgagc caatgggaaaaacccattgctgccaagtacactga ctcaatagggactttccaatgggtttttccattgt tggcaagcatataaggtcaatgtgggtgagtcaat agggactttccattgtattctgcccagtacataag gtcaataggggtgaatcaacaggaaagtcccatt ggagccaagtacactgcgtcaatagggactttcca ttgggttttgcccagtacataaggtcaatagggga tgagtcaatgggaaaaacccattggagccaagtac actgactcaatagggactttccattgggttttgcc cagtacataaggtcaataggggtgagtcaacagg aaagttccattggagccaagtacattgagtcaata gggactttccaatgggttttgcccagtacataagg tcaatgggaggtaagccaatgggtttttcccatta ctggcacgtatactgagtcattagggactttccaa tgggttttgcccagtacataaggtcaataggggtg aatcaacaggaaagtcccattggagccaagtacac tgagtcaatagggactttccattgggttttgccca gtacaaaaggtcaataggggtgagtcaatgggtt tttcccattattggcacgtacataaggtcaatagg ggtgagtcattgggtttttccagccaatttaatta aaacgccatgtactttcccaccattgacgtcaatg ggctattgaaactaatgcaacgtgacctttaaacg gtactttcccatagctgattaatgggaaagtaccg ttctcgagccaatacacgtcaatgggaagtgaaag ggcagccaaaacgtaacaccgccccggttttcccc tggaaattccatattggcacgcattctattggctg agctgcgttctacgtgggtataagaggcgcgacca gcgtcggtaccgtcgcagtcttcggtctgaccacc gtagaacgcagagctcctcgctgcag SEQ ID NO 11:
chicken β-actin promoter (692 bp)
(Note: “nnn” denotes an ambiguous sequence in highly GC-rich region. Could be 3-5 “g’s”)
cgcgccggatcagatctccatggtcgaggtgagcc ccacgttctgcttcactctccccatctcccccccc tccccacccccaattttgtatttatttatttttta attattttgtgcagcgatgggggcgggggggggggg nnncgcgcgccaggcggggcggggcggggcgaggg gcggggcggggcgaggcggagaggtgcggcggcag

-continued ccaatcagagcggcgcgctccgaaagtttcctttt atggcgaggcggcggcggcggcggccctataaaaa gcgaagcgcgcggcgggcgggagtcgctgcgcgct gccttcgccccgtgccccgctccgccgccgcctcg cgccgcccgccccggctctgactgaccgcgttact cccacaggtgagcgggcgggacggcccttctcctc cgggctgtaattagcggcaggaaggaaatgggcgg ggagggccttcgtgcgtcgccgcgccgccgtcccc ttctccctctccagcctcggggctgtccgcggggg gacggctgccttcgggggggacggggcagggcggg gttcggcttctggcgtgtgaccggcggctctagag cctctgctaaccatgttcatgccttcttctttttc ctacagctcctgggcaacgtgctggttattgtgct gtctcatcattttggcaaagaattgca SEQ ID NO 12: hCMV IE promoter, from strain AD169 (301 bp)
ggcagtacatctacgtattagtcatcgctattacc atggtgatgcggttttggcagtacatcaatgggcg tggatagcggtttgactcacggggatttccaagtc tccaccccattgacgtcaatgggagtttgttttgg caccaaaatcaacgggactttccaaaatgtcgtaa caactccgccccattgacgcaaatgggcggtaggc gtgtacggtgggaggtctatataagcagagctcgt ttagtgaaccgtcagatcgcctggagacgccatcc acgctgttttgacctccatag SEQ ID NO 13:
FHV US-9 polyadenylation signal
(55 bp)
caataaacatagcatacgttatgacatggtctacc gcgtcttatatggggacgac SEQ ID NO 14: HSV TK polyadenylation signal (370 bp)

gatccataattgattgacgggagatgg gggaggctaactgaaacacggaaggagacaatacc ggaaggaacccgcgctatgacggcaataaaaagac agaataaaacgcacgggtgttgggtcgtttgttca taaacgcggggttcggtcccagggctggcactctg tcgataccccaccgagaccccattggggccaatac gcccgcgtttcttccttttccccaccccacccccc aagttcgggtgaaggcccagggctcgcagccaacg tcggggcggcaggccctgccatagccactggcccc gtgggttagggacggggtcccccatggggaatggt ttatggttcgtgggggttattattttga SEQ ID NO 15: 228509-ILT-435Vec6
(mCMV IEpro-VP2-SV40pA/ILT/HVT)
(14113 bp)
(IBDV + ILT gene cassettes in
HVT EcoRI#7 fragment. Virus no.
HVT/IBDV/ILT 1386-134)
gaattccagactaaatgccccggcccaatttgtca agtgtgcagtcacggaggcgtcgaccgtgtccccg gcattaaacaggaaagcgttaaagtttttgaatgt taggtcacaggtacaaacataaatgtttgtacaaa caggtaacaggtacaaacataaatgccccggcata aatgtcccttacggcggatcgaaacgacattaggc atactcgggtaccattttgcattccgatcagcacg gatgaaattaggcaggaatgcggtttatattatgc ggcattggacaaacgatatggcattgattggcagt ttatgaatgtcttcatgttgggcgtaaacggattc ctattggttcagaagacaacgacgatatatttaga gagaaaaagctacccagcataggataaacacacat tgagcattgagagacataggtatcggtatggatgg gaaaactacacacgtgaacaccaaacgacttatat actcgagcggtgatactactgagcaagaatgcact gcatctgagccactgaatgaagactgtgatgaaaa tgtgaccatcgatggaattggagaagaatatgcgc agttcttcatgtccccgcaatgggtcccaaatcta catcgcttgagcgaggataccaaaaaggtataccg atgtatggtttccaacagactcaattattttccct attatgaggcgttcaggcggtctttgtttgatatg tatatgctaggtcggttggggcgtcgacttaagcg atctgactgggagactattatgcatctgtcaccaa cgcaaagtcggcgtctacatagaactttaagattt gtggagcgtagaattatcccatctaacagttatat acgcacatcgggccacgttccgccttcgagggcac ttccgacagatacgaatttaaagatggatgaataa ttaaattggaaagagtaactacattaatcgagcgt catgacggcgtcccgtgaaaatgggaattttctac tcgaaacaccgtgacatttgacagacctggaattg ttattctgatatatagtgggtgtgtctggccggca acatacataatgtgcatgcgaaaccactttttcag tgtacgctgacattgtgcaacacggaggggtagca tctacatacaatatatgttgattaatgattggaga aaaaactatgcagctcgccgatcatatggctaact cgccttcgtctatatggcggaccccgcgggaaaaa tcgacgtaccatctgatttacaacaccagtaatga acatgtcgcatccctgcccagatctgtgcgcccat -continued tggcgcggatcgttgtgaatgccgccgaaacactt caggtcggtatgagagccgggaggccgccatcagc aggagtttggcgagaggtgtttgatagaatgatga cagccttccgtgaccacgagcctactgcgacattt aatgctgcaaatcccattagaaaaatggtcgagac agttctacagaataatgaagagcccccgcggacgc atgctgaaatgggtaatcgccttatgaacattatg tactggtgttgcttgggacacgcaggacaatgctc gatatggcagttgtacgagacgaatcaggccattt taagtttattagatgaagtggttatcggcacaaca aatccctttgcaccctcgagcaatactggaagcc attatgcaccgcaatcgccaacaaggggacctcat cgcttgttgaggatgccaaagtggccgagtacctg gttagcatgcgcaaattgatataacataggcacgc tctgatgttacagaccacaataccgcatacattta ttgtaaggttgttaataaaggtttattctatgtaa gactacaatactttcgacattgcttgtatacatat taaatactttctcaagttcctattacataaaatgg gatctatcattacattcgttaagagtctggataat tttactgtttgccagcttcgatcttggaacgtact gtggatagtgccttacttggaatcgtgaaaatttg aaacgtccattatttggatatcttccggttgtccc atatcccgccctggtaccgctcggataccttgccc gtatggattcgtattgacagtcgcgcaatcgggga ccaacaacgcgtgggtccacactcattcggaaatt ttccgatgattctgaatatttattgccgctcgtta cgagtcgttggacatatctgtaatacatttcttct tctgaaggatcgctgcacatttgatctatacattg gccaggatgttcaagtctcagatgttgcattctgg cacagcacaactttatggcatttccgatgtaatcg tccggcagccctgggggagttctatattcgcatat tgggatggtaaggacaatagcagatctcgcaacct ccagggaggctataataacgtttttaaaggatgga tttctcataaaaatctgtcgcaaattacactgaga atatcctttactagcgccgattgagagcatcgtcg tccaattttctaaatggaaagaaaacaaggcgggc aagagtgttccaaacattttcattttcggcgaatc tctcaaatcccatggcgtgcaattgattgcaaaat tggcacttccgttcacgtttgtatctccaaactct aagacacttttaattgaaaaactacgttctagtgt ggaaagaaacctataggcagaccatagaactattt gacaccacatatctttttgtatgtcaaactgacca tgatcgtatgttgctgaatgcactagggcaattcg ctcgcgcgactccatacattgaataattccacacg tcagctcatcggttagcaaggtccagtagttgaag tcatttattttccccgcggctggccaaatctacc tctgggaatatccaagttgtcgaatatgatcgcac cggctctggtcatggtgaaggaactgtagcataaa gacgcaggtatcataggggtaatatttttttattc actcacatactaaaagtaacgcatattagcaccat gtatgggctatcaattgacatttgcgtagcactac atcacgattatgtacaacataatgggacaacatat ggcaagtagatgcaatttcctcacactagttgggt ttatctactattgaattttcccctatctgtgatac acttgggagcctctacaagcatattgccatcatgt acgtttttatctactgtcttaacgcccatgggaac ggaggcgtcgtcgtcatgtattggacggcaacata ggcagcaacacaaattgcgtttaggtggggtgcat gtggactcgataccaagcccctgcagctggggaac gtctggtggagagccgataatttgatatacgcacg ccatattactgtcgttgaagtacgccttatcttct atgttttcaaatttaggttcccaagtggacgtgag aagtgtttgtatctcacatggaatggcccaaggca ttccagcccaggtgcctggtactttaatggcaaac aaacgttttggtagaggtattgattctattgcagt tctgcagatatctgcagccccgagtatccacaggc tatacgatacgttatcggaggcaagctgcggccgc tctagaactagtggatcccccgggctgcagcccaa tgtggaattcgcccttgcacattgttactcctgca tcttaaaaatatatcctgtagtaattttcacagca atgtcataacatcatctcgctaaagaatgacctgg gattggagaagtaatgaatatttgcaaccaatgca ttgaataaactaacattaaacgaattcactagtgg atcccccaactccgcccgttttatgactagaacca atagtttttaatgccaaatgcactgaaatcccta atttgcaaagccaaacgcccctatgtgagtaata cggggactttttacccaatttcccacgcggaaagc cccctaatacactcatatggcatatgaatcagcac ggtcatgcactctaatggcggcccatagggacttt ccacatagggggcgttcaccatttcccagcatagg ggtggtgactcaatggcctttacccaagtacattg ggtcaatgggaggtaagccaatgggtttttcccat tactggcaagcacactgagtcaaatgggactttcc actgggttttgcccaagtacattgggtcaatggga ggtgagccaatgggaaaaacccattgctgccaagt acactgactcaatagggactttccaatgggttttt ccattgttggcaagcatataaggtcaatgtgggtg agtcaatagggactttccattgtattctgcccagt acataaggtcaataggggggtgaatcaacaggaaag tcccattggagccaagtacactgcgtcaataggga ctttccattgggttttgcccagtacataaggtcaa taggggatgagtcaatgggaaaaacccattggagc caagtacactgactcaatagggactttccattggg ttttgcccagtacataaggtcaataggggggtgagt caacaggaaagttccattggagccaagtacattga gtcaatagggactttccaatgggttttgcccagta cataaggtcaatgggaggtaagccaatgggttttt cccattactggcacgtatactgagtcattagggac tttccaatgggttttgcccagtacataaggtcaat aggggtgaatcaacaggaaagtcccattggagcca agtacactgagtcaatagggactttccattgggtt ttgcccagtacaaaaggtcaataggggggtgagtca atgggtttttcccattattggcacgtacataaggt caataggggtgagtcattgggtttttccagccaat ttaattaaaacgccatgtactttcccaccattgac gtcaatgggctattgaaactaatgcaacgtgacct ttaaacggtactttcccatagctgattaatgggaa agtaccgttctcgagccaatacacgtcaatgggaa gtgaaagggcagccaaaacgtaacaccgccccggt tttcccctggaaattccatattggcacgcattcta ttggctgagctgcgttctacgtgggtataagaggc gcgaccagcgtcggtaccgtcgcagtcttcggtct gaccaccgtagaacgcagagctcctcgctgcaggc ggccgctctagaactcgtcgatcgcagcgatgaca aacctgcaagatcaaacccaacagattgttccgtt catacggagccttctgatgccaacaaccggaccgg cgtccattccggacgacaccctggagaagcacact ctcaggtcagagacctcgacctacaatttgactgt gggggacacagggtcagggctaattgtctttttcc ctggattccctggctcaattgtgggtgctcactac acactgcagagcaatgggaactacaagttcgatca -continued gatgctcctgactgcccagaacctaccggccagct
acaactactgcagactagtgagtcggagtctcaca
gtgaggtcaagcacactccctggtggcgtttatgc
actaaacggcaccataaacgccgtgaccttccaag
gaagcctgagtgaactgacagatgttagctacaat
gggttgatgtctgcaacagccaacatcaacgacaa
aattgggaatgtcctggtaggggaaggggtcactg
tcctcagcctacccacatcatatgatcttgggtat
gtgaggcttggtgaccccattcccgctatagggct
tgacccaaaaatggtagctacatgcgacagcagtg
acaggcccagagtctacaccataactgcagccgat
gattaccaattctcatcacagtaccaaccaggtgg
ggtaacaatcacactgttctcagccaacattgatg
ctatcacaagcctcagcattgggggagagctcgtg
tttcaaacaagcgtccaaggccttgtactgggcgc
caccatctaccttataggctttgatgggactgcgg
taatcaccagagctgtggccgcagataatgggctg
acggccggcaccgacaatcttatgccattcaatct
tgtcattccaaccaatgagataacccagccaatca
catccatcaaactggagatagtgacctccaaaagt
ggtggtcaggcaggggatcagatgtcatggtcggc
aagtgggagcctagcagtgacgatccatggtggca
actatccaggggccctccgtcccgtcacactagta
gcctacgaaagagtggcaacaggatccgtcgttac
ggtcgctggggtgagtaacttcgagctgattccaa
atcctgaactagcaaagaacctggttacagaatac
ggccgatttgacccaggagccatgaactacacaaa
attgatactgagtgagagggaccgtcttggcatca
agaccgtctggccaacaagggagtacactgatttt
cgtgagtacttcatggaggtggccgacctcaactc
tcccctgaagattgcaggagcatttggcttcaaag
acataatccgggctataaggaggtaagcttcagac
atgataagatacattgatgagtttggacaaaccac
aactagaatgcagtgaaaaaaatgctttatttgtg
aaatttgtgatgctattgctttatttgtaaccatt
ataagctgcaataaacaagttaacaacaacaattg
cattcattttatgtttcaggttcagggggaggtgt
gggaggttttttcggatcctctagagtcgacggca
gagtcgcagacgcccctattggacgtcaaaattgt
agaggtgaagttttcaaacgatggcgaagtaacgg
cgacttgcgtttccaccgtcaaatctccctatagg -continued gtagaaactaattggaaagtagacctcgtagatgt
aatggatgaaatttctgggaacagtcccgccgggg
tttttaacagtaatgagaaatggcagaaacagctg
tactacagagtaaccgatggaagaacatcggtcca
gctaatgtgcctgtcgtgcacgagccattctccgg
aaccttactgtcttttcgacacgtctcttatagcg
agggaaaaagatatcgcgccagagttatactttac
ctctgatccgcaaacggcatactgcacaataactc
tgccgtccggcgttgttccgagattcgaatggagc
cttaataatgtttcactgccggaatatttgacggc
cacgaccgttgtttcgcataccgctggccaaagta
cagtgtggaagagcagcgcgagagcaggcgaggcg
tggatttctggccggggaggcaatatatacgaatg
caccgtcctcatctcagacggcactcgcgttacta
cgcgaaaggagaggtgcttaacaaacacatggatt
gcggtggaaaacggtgctgctcaggcgcagctgta
ttcactcttttctggacttgtgtcaggattatgcg
ggagcatatctgctttgtacgcaacgctatggacc
gccatttatttttgaggaatgctttttggactatc
gtactgctttcttccttcgctagccagagcaccgc
cgccgtcacgtacgactacattttaggccgtcgcg
cgctcgacgcgctaaccataccggcggttggcccg
tataacagatacctcactagggtatcaagaggctg
cgacgttgtcgagctcaacccgatttctaacgtgg
acgacatgatatcggcggccaaagaaaaagagaag
gggggccctttcgaggcctccgtcgtctggttcta
cgtgattaagggcgacgacggcgaggacaagtact
gtccaatctatagaaaagagtacagggaatgtggc
gacgtacaactgctatctgaatgcgccgttcaatc
tgcacagatgtgggcagtggactatgttcctagca
cccttgtatcgcgaaatggcgcgggactgactata
ttctcccccactgctgcgctctctggccaatactt
gctgaccctgaaaatcgggagatttgcgcaaacag
ctctcgtaactctagaagttaacgatcgctgttta
aagatcgggtcgcagcttaactttttaccgtcgaa
atgctggacaacagaacagtatcagactggatttc
aaggcgaacacctttatccgatcgcagacaccaat
acacgacacgcggacgacgtatatcggggatacga
agatattctgcagcgctggaataatttgctgagga
aaaagaatcctagcgcgccagaccctcgtccagat -continued agcgtcccgcaagaaattcccgctgtaaccaagaa
agcggaagggcgcaccccggacgcagaaagcagcg
aaaagaaggcccctccagaagactcggaggacgac
atgcaggcagaggcttctggagaaaatcctgccgc
cctccccgaagacgacgaagtccccgaggacaccg
agcacgatgatccaaactcggatcctgactattac
aatgacatgcccgccgtgatcccggtggaggagac
tactaaaagttctaatgccgtctccatgcccatat
tcgcggcgttcgtagcctgcgcggtcgcgctcgtg
gggctactggtttggagcatcgtaaaatgcgcgcg
tagctaatcgagcctagaataggtggtttcttcct
acatgccacgcctcacgctcataatataaatcaca
tggaatagcataccaatgcctattcattgggacgt
tcgaaaagcatggcatcgctacttggaactctggc
tctccttgccgcgacgctcgcacccttcggcgcga
tgggaatcgtgatcactggaaatcacgtctccgcc
aggattgacgacgatcacatcgtgatcgtcgcgcc
tcgccccgaagctacaattcaactgcagctatttt
tcatgcctggccagagaccccacaaaccctactca
ggaaccgtccgcgtcgcgtttcggtctgatataac
aaaccagtgctaccaggaacttagcgaggagcgct
ttgaaaattgcactcatcgatcgtcttctgttttt
gtcggctgtaaagtgaccgagtacacgttctccgc
ctcgaacagactaaccggacctccacacccgttta
agctcactatacgaaatcctcgtccgaacgacagc
gggatgttctacgtaattgttcggctagacgacac
caaagaacccattgacgtcttcgcgatccaactat
cggtgtatcaattcgcgaacaccgccgcgactcgc
ggactctattccaaggcttcgtgtcgcaccttcgg
attacctaccgtccaacttgaggcctatctcagga
ccgaggaaagttggcgcaactggcaagcgtacgtt
gccacggaggccacgacgaccagcgccgaggcgac
aaccccgacgcccgtcactgcaaccagcgcctccg
aacttgaagcggaacactttacctttccctggcta
gaaaatggcgtggatcattacgaaccgacacccgc
aaacgaaaattcaaacgttactgtccgtctcggga
caatgagccctacgctaattggggtaaccgtggct
gccgtcgtgagcgcaacgatcggcctcgtcattgt
aatttccatcgtcaccagaaacatgtgcaccccgc
accgaaaattagacacggtctcgcaagacgacgaa
gaacgttcccaaactagaagggaatcgcgaaaatt -continued tggacccatggttgcgtgcgaaataaacaaggggg
ctgaccaggatagtgaacttgtggaactggttgcg
attgttaacccgtctgcgctaagctcgcccgactc
aataaaaatgtgattaagtctgaatgtggctctcc
aatcatttcgattctctaatctcccaatcctctca
aaaggggcagtatcggacacggactgggaggggcg
tacacgatagttatatggtacagcagaggcctctg
aacacttaggaggagaattcagccggggagagccc
ctgttgagtaggcttgggagcatattgcaggatga
acatgttagtgatagttctcgcctcttgtcttgcg
cgcctaacttttgcgacgcgacacgtcctcttttt
ggaaggcactcaggctgtcctcggggaagatgatc
ccagaaacgttccggaagggactgtaatcaaatgg
acaaaagtcctgcggaacgcgtgcaagatgaaggc
ggccgatgtctgctcttcgcctaactattgctttc
atgatttaatttacgacggaggaaagaaagactgc
ccgcccgcgggacccctgtctgcaaacctggtaat
tttactaaagcgcggcgaagcttagcttgcctccg
attctagcattacatagccggtcagtagatcctgc
cattcggtagcgcaaccggctacatcttcaaacag
tctcacgataaatgcatctctcgttcctgccaatc
cggaaccgggcataccactcccgcctgccgattta
attctcacaattgggcgatgccggcggggcaaaac
gaatgtggatttggcaaaccgacacaggtctgctg
tacggactaatatgggcacacccacatcattcttc
agatgctccatgcattgttctatgagaaagatcca
tagggtggaggcagcgtcacgagatcgcccaggca
atcgatcgcattcgtctagtaaagtgacgagagtt
atcatgcacacacccatgcccacgccttccgaata
actggagctgtggaagatcggaaacgtctttttga
ctgccggtctcgtactactttcgcacaggtgtata
cccggacgcgtactatatattttatatcatccaac
gtccgaaattacatacgtggcggcgatggaagtag
atgttgagtcttcgaaagtaagtgcctcgaatatg
ggtattgtctgtgaaaatatcgaaagcggtacgac
ggttgcagaaccgtcgatgtcgccagatactagta
acaatagcttcgataacgaagacttccgtgggcct
gaatacgatgtggagataaataccagaaaatctgc
taatcttgatcgtatggaatcttcgtgccgtgaac
aacgagcggcgtgcgaacttcgaaagtgttcgtgt -continued cctacgtctgccgtgcgcatgcaatacagtattct ttcatctctcgctccgggttcagagggtcatgtat atatatgtactagatacggggacgcggaccaaaaa aaatgcatagtgaaggcagtcgttggaggaaagaa tcccgggagggaagtggatattttaaaaaccatct cacataaatcaattataaaattaatccatgcctat aaatggaaaaatgttgtgtgtatggcaatgcgtgt atatcgttatgatcttttcacatatattgacggag tcggccctatgccccttcaacagatgatctatatt caacgtggactactagaggcgctagcatacataca tgaaaggggcatcattcaccgagacgtaaagacgg agaatatattcttggataatcacgaaaatgcagtt ttgggtgacttcggtgctgcatgccaactaggaga ttgtatagatacgccccaatgttacggttggagcg gaactgtggaaacaaattcgccggaattatctgca cttgatccgtattgcacaaaaacagatatttggag tgccggattggttctatatgagatggcaattaaaa atgtaccattgtttagtaagcaggtgaaaagttcg ggatctcagctgagatccataatacggtgcatgca agtgcatgaactggagtttccccgcaacgattcta ccaacctctgtaaacatttcaaacaatatgcggtt cgtgtacgaccgccttataccattcctcgagttat aagaaatggggggatgccaatggatgttgaatatg tcatttctaaaatgcttacgtttgaccaggagttc agaccttctgctaaggaaatattgaatatgcccct atttactaaggcgccgattaacctgcttaatatca caccctctgacagtgtctaacggtatacaggcggg agcgggtcgtggcgtcatcatcaccacttgagaat ttatattttgaattgttgattgataaattaacctg attcattgagaactgaaacgccatattggtttctt ggatatgtctacaacaattagttaaattgctatgt tctactgcgagtaacatttgataagttgtaagaga cgggcgactcatgtcgaagttgacgaatataaagt acataacgtgtttagaatacccagaatccgaatag tccgcgggggcgtcttctcgcgtgagtaccaaata ctgagttgaacttgaaaatgctaaatctgtgacac tctttgtgtgatgattattgtcaccacttcgaaga tggcttcgacattcatgatgttctggtgtttgttt ggaatcgtaatagcgcttgtttcgtccaagtctga caacaaagaaaatctgaagaattatatcacggata agtcaaccaatattagaatacccacgccattattt -continued gtatcaacggaaaactcttatcccacaaaacatgt aatctacgatgaaaactgtggcttcgctgtactca atcctataagtgaccccaaatatgtccttttgagc cagcttctaatgggaaggcgcaaatatgatgcgac ggtcgcgtggtttgttctcggtaaaatgtgtgcca gattaatatatttgcgcgaattttataactgctcg acaaatgagccttttggcacatgttctatgagctc tcctggatggtgggacaggcgctacgtctcaacca gtttcatttctcgcgacgaattacagctggttttt gcagcgccgtcccgagaattagatggtttatatac gcgcgtagtagttgtcaacggggactttactacgg ccgatataatgtttaatgttaaagtggcatgtgcc ttttcaaagactggaatagaagatgatacattatg caaaccctttcatttctttgccaatgcaacattgc acaatttaaccatgattagatcggtaactcttcga gcgcacgaaagccatttaaaggaatgggtggcacg gagaggtggtaacgtccctgcagtgctacttgagt ctaccatgtatcatgcatccaatctgcctagaaat ttcagggatttctacataaagtctccagatgatta taagtataatcacctagatgggccatctgtaatgc tcatcactgacagacctagtgaagatttggatggg aggctcgttcaccaaagtgacatttttactactac aagtcctataaaacaggtccggtatgaagagcatc agtcacatacaaagcagtatcctgtaaacaaaata caagctataatttttttgatagggttaggctcgtt cattggaagcatattcgtagttttggtagtatgga ttatacgcagatattgcaatggagcgcggagtggg ggaacgccccccagtcctcgccggtatgtgtatac caggctatgatcacgtgtgaaacttgggcggacct gtatcatatgtacaccgtccctattcgtttatagc cagtacgtgttatctgcacatagaggaacatgtgt catactgggatcgcatgcatggtatgtgtgactct aatattattctgtatcataataaaaacacagtgca tggtatatagaggatcgctggtaagcactacggta gaccaatcggctcagattgcattctttggcatcga taccgttgttaatttatatggcaaagtcttgttca tgggagatcagtatttggaggaaatatactctgga acgatggaaatactcaaatggaatcaagctaaccg ctgctattctattgcgcatgcaacatattacgccg actgtcctataatcagttctacggtattcagagga -continued tgccgggacgccgttgtttatactaggccccacag cagaattc SEQ ID NO 16: 1333-85.B6 (ILT/Chicken
β-actin pro-VP2-FHV US9pA /HVT) (13064 bp) (ILT + IBDV gene cassettes in HVT EcoRI#7 fragment.) Virus no. HVT/ILT/IBDV 1386-48.1.1.1 gaattccagactaaatgccccggcccaatttgtca agtgtgcagtcacggaggcgtcgaccgtgtccccg gcattaaacaggaaagcgttaaagtttttgaatgt taggtcacaggtacaaacataaatgtttgtacaaa caggtaacaggtacaaacataaatgccccggcata aatgtcccttacggcggatcgaaacgacattaggc atactcgggtaccattttgcattccgatcagcacg gatgaaattaggcaggaatgcggtttatattatgc ggcattggacaaacgatatggcattgattggcagt ttatgaatgtcttcatgttgggcgtaaacggattc ctattggttcagaagacaacgacgatatatttaga gagaaaaagctacccagcataggataaacacacat tgagcattgagagacataggtatcggtatggatgg gaaaactacacacgtgaacaccaaacgacttatat actcgagcggtgatactactgagcaagaatgcact gcatctgagccactgaatgaagactgtgatgaaaa tgtgaccatcgatggaattggagaagaatatgcgc agttcttcatgtccccgcaatgggtcccaaatcta catcgcttgagcgaggataccaaaaaggtataccg atgtatggtttccaacagactcaattattttccct attatgaggcgttcaggcggtctttgtttgatatg tatatgctaggtcggttggggcgtcgacttaagcg atctgactgggagactattatgcatctgtcaccaa cgcaaagtcggcgtctacatagaactttaagattt gtggagcgtagaattatcccatctaacagttatat acgcacatcgggccacgttccgccttcgagggcac ttccgacagatacgaatttaaagatggatgaataa ttaaattggaaagagtaactacattaatcgagcgt catgacggcgtcccgtgaaaatgggaattttctac tcgaaacaccgtgacatttgacagacctggaattg ttattctgatatatagtgggtgtgtctggccggca acatacataatgtgcatgcgaaaccactttttcag tgtacgctgacattgtgcaacacggaggggtagca tctacatacaatatatgttgattaatgattggaga aaaaactatgcagctcgccgatcatatggctaact cgccttcgtctatatggcggaccccgcgggaaaaa -continued tcgacgtaccatctgatttacaacaccagtaatga acatgtcgcatccctgcccagatctgtgcgcccat tggcgcggatcgttgtgaatgccgccgaaacactt caggtcggtatgagagccgggaggccgccatcagc aggagtttggcgagaggtgtttgatagaatgatga cagccttccgtgaccacgagcctactgcgacattt aatgctgcaaatcccattagaaaaatggtcgagac agttctacagaataatgaagagcccccgcggacgc atgctgaaatgggtaatcgccttatgaacattatg tactggtgttgcttgggacacgcaggacaatgctc gatatggcagttgtacgagacgaatcaggccattt taagtttattagatgaagtggttatcggcacaaca aatccctttttgcaccctcgagcaatactggaagcc attatgcaccgcaatcgccaacaaggggacctcat cgcttgttgaggatgccaaagtggccgagtacctg gttagcatgcgcaaattgatataacataggcacgc tctgatgttacagaccacaataccgcatacattta ttgtaaggttgttaataaaggtttattctatgtaa gactacaatactttcgacattgcttgtatacatat taaatactttctcaagttcctattacataaaatgg gatctatcattacattcgttaagagtctggataat tttactgtttgccagcttcgatcttggaacgtact gtggatagtgccttacttggaatcgtgaaaatttg aaacgtccattatttggatatcttccggttgtccc atatcccgccctggtaccgctcggataccttgccc gtatggattcgtattgacagtcgcgcaatcgggga ccaacaacgcgtgggtccacactcattcggaaatt ttccgatgattctgaatatttattgccgctcgtta cgagtcgttggacatatctgtaatacatttcttct tctgaaggatcgctgcacatttgatctatacattg gccaggatgttcaagtctcagatgttgcattctgg cacagcacaactttatggcatttccgatgtaatcg tccggcagccctgggggagttctatattcgcatat tgggatggtaaggacaatagcagatctcgcaacct ccagggaggctataataacgtttttaaaggatgga tttctcataaaaatctgtcgcaaattacactgaga atatcctttactagcgccgattgagagcatcgtcg tccaattttctaaatggaaagaaaacaaggcgggc aagagtgttccaaacattttcattttcggcgaatc tctcaaatcccatggcgtgcaattgattgcaaaat -continued tggcacttccgttcacgtttgtatctccaaactct aagacacttttaattgaaaaactacgttctagtgt ggaaagaaacctataggcagaccatagaactattt gacaccacatatctttttgtatgtcaaactgacca tgatcgtatgttgctgaatgcactagggcaattcg ctcgcgcgactccatacattgaataattccacacg tcagctcatcggttagcaaggtccagtagttgaag tcatttatttttccccgcggctggccaaatctacc tctgggaatatccaagttgtcgaatatgatcgcac cggctctggtcatggtgaaggaactgtagcataaa gacgcaggtatcataggggtaatatttttttattc actcacatactaaaagtaacgcatattagcaccat gtatgggctatcaattgacatttgcgtagcactac atcacgattatgtacaacataatgggacaacatat ggcaagtagatgcaatttcctcacactagttgggt ttatctactattgaattttcccctatctgtgatac acttgggagcctctacaagcatattgccatcatgt acgtttttatctactgtcttaacgcccatgggaac ggaggcgtcgtcgtcatgtattggacggcaacata ggcagcaacacaaattgcgtttaggtggggtgcat gtggactcgataccaagcccctgcagctggggaac gtctggtggagagccgataatttgatatacgcacg ccatattactgtcgttgaagtacgccttatcttct atgttttcaaatttaggttcccaagtggacgtgag aagtgtttgtatctcacatggaatggcccaaggca ttccagcccaggtgcctggtactttaatggcaaac aaacgttttggtagaggtattgattctattgcagt tctgcagatatctgcagccccgagtatccacaggc tatacgatacgttatcggaggcaagcttaattaag taccgagctcgaattggcgcgcccgacggcagagt cgcagacgcccctattggacgtcaaaattgtagag gtgaagttttcaaacgatggcgaagtaacggcgac ttgcgtttccaccgtcaaatctccctatagggtag aaactaattggaaagtagacctcgtagatgtaatg gatgaaatttctgggaacagtcccgccggggtttt taacagtaatgagaaatggcagaaacagctgtact acagagtaaccgatggaagaacatcggtccagcta atgtgcctgtcgtgcacgagccattctccggaacc ttactgtcttttcgacacgtctcttatagcgaggg aaaaagatatcgcgccagagttatactttacctct gatccgcaaacggcatactgcacaataactctgcc -continued gtccggcgttgttccgagattcgaatggagcctta ataatgtttcactgccggaatatttgacggccacg accgttgtttcgcataccgctggccaaagtacagt gtggaagagcagcgcgagagcaggcgaggcgtgga tttctggccggggaggcaatatatacgaatgcacc gtcctcatctcagacggcactcgcgttactacgcg aaaggagaggtgcttaacaaacacatggattgcgg tggaaaacggtgctgctcaggcgcagctgtattca ctcttttctggacttgtgtcaggattatgcgggag catatctgctttgtacgcaacgctatggaccgcca tttatttttgaggaatgctttttggactatcgtac tgctttcttccttcgctagccagagcaccgccgcc gtcacgtacgactacattttaggccgtcgcgcgct cgacgcgctaaccataccggcggttggcccgtata acagatacctcactagggtatcaagaggctgcgac gttgtcgagctcaacccgatttctaacgtggacga catgatatcggcggccaaagaaaaagagaaggggg gccctttcgaggcctccgtcgtctggttctacgtg attaagggcgacgacggcgaggacaagtactgtcc aatctatagaaaagagtacagggaatgtggcgacg tacaactgctatctgaatgcgccgttcaatctgca cagatgtgggcagtggactatgttcctagcaccct tgtatcgcgaaatggcgcgggactgactatattct cccccactgctgcgctctctggccaatacttgctg accctgaaaatcgggagatttgcgcaaacagctct cgtaactctagaagttaacgatcgctgtttaaaga tcgggtcgcagcttaactttttaccgtcgaaatgc tggacaacagaacagtatcagactggatttcaagg cgaacacctttatccgatcgcagacaccaatacac gacacgcggacgacgtatatcggggatacgaagat attctgcagcgctggaataatttgctgaggaaaaa gaatcctagcgcgccagaccctcgtccagatagcg tcccgcaagaaattcccgctgtaaccaagaaagcg gaagggcgcaccccggacgcagaaagcagcgaaaa gaaggcccctccagaagactcggaggacgacatgc aggcagaggcttctggagaaaatcctgccgccctc cccgaagacgacgaagtccccgaggacaccgagca cgatgatccaaactcggatcctgactattacaatg acatgcccgccgtgatcccggtggaggagactact aaaagttctaatgccgtctccatgcccatattcgc -continued ggcgttcgtagcctgcgcggtcgcgctcgtggggc tactggtttggagcatcgtaaaatgcgcgcgtagc taatcgagcctagaataggtggtttcttcctacat gccacgcctcacgctcataatataaatcacatgga atagcataccaatgcctattcattgggacgttcga aaagcatggcatcgctacttggaactctggctctc cttgccgcgacgctcgcacccttcggcgcgatggg aatcgtgatcactggaaatcacgtctccgccagga ttgacgacgatcacatcgtgatcgtcgcgcctcgc cccgaagctacaattcaactgcagctatttttcat gcctggccagagaccccacaaaccctactcaggaa ccgtccgcgtcgcgtttcggtctgatataacaaac cagtgctaccaggaacttagcgaggagcgctttga aaattgcactcatcgatcgtcttctgtttttgtcg gctgtaaagtgaccgagtacacgttctccgcctcg aacagactaaccggacctccacacccgtttaagct cactatacgaaatcctcgtccgaacgacagcggga tgttctacgtaattgttcggctagacgacaccaaa gaacccattgacgtcttcgcgatccaactatcggt gtatcaattcgcgaacaccgccgcgactcgcggac tctattccaaggcttcgtgtcgcaccttcggatta cctaccgtccaacttgaggcctatctcaggaccga ggaaagttggcgcaactggcaagcgtacgttgcca cggaggccacgacgaccagcgccgaggcgacaacc ccgacgcccgtcactgcaaccagcgcctccgaact tgaagcggaacactttacctttccctggctagaaa atggcgtggatcattacgaaccgacacccgcaaac gaaaattcaaacgttactgtccgtctcgggacaat gagccctacgctaattggggtaaccgtggctgccg tcgtgagcgcaacgatcggcctcgtcattgtaatt tccatcgtcaccagaaacatgtgcaccccgcaccg aaaattagacacggtctcgcaagacgacgaagaac gttcccaaactagaagggaatcgcgaaaatttgga cccatggttgcgtgcgaaataaacaaggggggctga ccaggatagtgaacttgtggaactggttgcgattg ttaacccgtctgcgctaagctcgcccgactcaata aaaatgtgattaagtctgaatgtggctctccaatc atttcgattctctaatctcccaatcctctcaaaag gggcagtatcggacacggactgggaggggcgtaca cgatagttatatggtacagcagaggcctctgaaca cttaggaggagaattcagccggggagagcccctgt -continued tgagtaggcttgggagcatattgcaggatgaacat gttagtgatagttctcgcctcttgtcttgcgcgcc taacttttgcgacgcgacacgtcctctttttggaa ggcactcaggctgtcctcggggaagatgatcccag aaacgttccggaagggactgtaatcaaatggacaa aagtcctgcggaacgcgtgcaagatgaaggcggcc gatgtctgctcttcgcctaactattgctttcatga tttaatttacgacggaggaaagaaagactgcccgc ccgcgggacccctgtctgcaaacctggtaatttta ctaaagcgcggcgggcgcgccggatcagatctcca tggtcgaggtgagccccacgttctgcttcactctc cccatctccccccctccccacccccaattttgta tttatttatttttaattattttgtgcagcgatgg gggcgggggggggggnnncgcgcgccaggcggggc ggggcggggcgaggggcggggcggggcgaggcgga gaggtgcggcggcagccaatcagagcggcgcgctc cgaaagtttccttttatggcgaggcggcggcggcg gcggccctataaaaagcgaagcgcgcggcgggcgg gagtcgctgcgcgctgccttcgccccgtgccccgc tccgccgccgcctcgcgccgcccgccccggctctg actgaccgcgttactcccacaggtgagcgggcggg acggcccttctcctccgggctgtaattagcggcag gaaggaaatgggcggggagggccttcgtgcgtcgc cgcgccgccgtccccttctccctctccagcctcgg ggctgtccgcggggggacggctgccttcgggggg acggggcagggcggggttcggcttctggcgtgtga ccggcggctctagagcctctgctaaccatgttcat gccttcttctttttcctacagctcctgggcaacgt gctggttattgtgctgtctcatcattttggcaaag aattgcagatctggatctatgacaaacctgcaaga tcaaacccaacagattgttccgttcatacggagcc ttctgatgccaacaaccggaccggcgtccattccg gacgacaccctggagaagcacactctcaggtcaga gacctcgacctacaatttgactgtgggggacacag ggtcagggctaattgtctttttccctggattccct ggctcaattgtgggtgctcactacacactgcagag caatgggaactacaagttcgatcagatgctcctga ctgcccagaacctaccggccagctacaactactgc agactagtgagtcggagtctcacagtgaggtcaag cacactccctggtggcgtttatgcactaaacggca -continued ccataaacgccgtgaccttccaaggaagcctgagt
gaactgacagatgttagctacaatgggttgatgtc
tgcaacagccaacatcaacgacaaagttgggaatg
tcctggtaggggaaggggtcactgtcctcagccta
cccacatcatatgatcttgggtatgtgaggcttgg
tgaccccattcccgctatagggcttgacccaaaaa
tggtagctacatgcgacagcagtgacaggcccaga
gtctacaccataactgcagccgatgattaccaatt
ctcatcacagtaccaaccaggtggggtaacaatca
cactgttctcagccaacattgatgctatcacaagc
ctcagcattgggggagagctcgtgtttcaaacaag
cgtccaaggccttgtactgggcgccaccatctacc
ttataggctttgatgggactgcggtaatcaccaga
gctgtggccgcagataatgggctgacggccggcac
cgacaatcttatgccattcaatcttgtcattccaa
ccaatgagataacccagccgatcacatccatcaaa
ctggagatagtgacctccaaaagtggtggtcaggc
aggggatcagatgtcatggtcggcaagtgggagcc
tagcagtgacgatccatggtggcaactatccaggg
gccctccgtcccgtcacactagtagcctacgaaag
agtggcaacaggatccgtcgttacggtcgctgggg
tgagtaacttcgagctgatcccaaatcctgaacta
gcaaagaacctggttacagaatacggccgatttga
cccaggagccatgaactacacaaaattgatactga
gtgagagggaccgtcttggcatcaagaccgtctgg
ccaacaagggagtacactgattttcgtgagtactt
catggaggtggccgacctcaactctcccctgaaga
ttgcaggagcatttggcttcaaagacataatccgg
gctataaggaggtaagatccgatctctcgattaat
taacaataaacatagcatacgttatgacatggtct
accgcgtcttatatggggacgacaagcttgcctcc
gattctagcattacatagccggtcagtagatcctg
ccattcggtagcgcaaccggctacatcttcaaaca
gtctcacgataaatgcatctctcgttcctgccaat
ccggaaccgggcataccactcccgcctgccgattt
aattctcacaattgggcgatgccggcggggcaaaa
cgaatgtggatttggcaaaccgacacaggtctgct
gtacggactaatatgggcacacccacatcattctt
cagatgctccatgcattgttctatgagaaagatcc
atagggtggaggcagcgtcacgagatcgcccaggc
aatcgatcgcattcgtctagtaaagtgacgagagt -continued tatcatgcacacacccatgcccacgccttccgaat
aactggagctgtggaagatcggaaacgtctttttg
actgccggtctcgtactactttcgcacaggtgtat
acccggacgcgtactatatattttatatcatccaa
cgtccgaaattacatacgtggcggcgatggaagta
gatgttgagtcttcgaaagtaagtgcctcgaatat
gggtattgtctgtgaaaatatcgaaagcggtacga
cggttgcagaaccgtcgatgtcgccagatactagt
aacaatagcttcgataacgaagacttccgtgggcc
tgaatacgatgtggagataaataccagaaaatctg
ctaatcttgatcgtatggaatcttcgtgccgtgaa
caacgagcggcgtgcgaacttcgaaagtgttcgtg
tcctacgtctgccgtgcgcatgcaatacagtattc
tttcatctctcgctccgggttcagagggtcatgta
tatatatgtactagatacggggacgcggaccaaaa
aaaatgcatagtgaaggcagtcgttggaggaaaga
atcccgggagggaagtggatattttaaaaaccatc
tcacataaatcaattataaaattaatccatgccta
taaatggaaaaatgttgtgtgtatggcaatgcgtg
tatatcgttatgatcttttcacatatattgacgga
gtcggccctatgccccttcaacagatgatctatat
tcaacgtggactactagaggcgctagcatacatac
atgaaaggggcatcattcaccgagacgtaaagacg
gagaatatattcttggataatcacgaaaatgcagt
tttgggtgacttcggtgctgcatgccaactaggag
attgtatagatacgccccaatgttacggttggagc
ggaactgtggaaacaaattcgccggaattatctgc
acttgatccgtattgcacaaaaacagatatttgga
gtgccggattggttctatatgagatggcaattaaa
aatgtaccattgtttagtaagcaggtgaaaagttc
gggatctcagctgagatccataatacggtgcatgc
aagtgcatgaactggagtttccccgcaacgattct
accaacctctgtaaacatttcaaacaatatgcggt
tcgtgtacgaccgccttataccattcctcgagtta
taagaaatgggggggatgccaatggatgttgaatat
gtcatttctaaaatgcttacgtttgaccaggagtt
cagaccttctgctaaggaaatattgaatatgcccc
tatttactaaggcgccgattaacctgcttaatatc
acaccctctgacagtgtctaacggtatacaggcgg
gagcgggtcgtggcgtcatcatcaccacttgagaa -continued tttatattttgaattgttgattgataaattaacct gattcattgagaactgaaacgccatattggtttct tggatatgtctacaacaattagttaaattgctatg ttctactgcgagtaacatttgataagttgtaagag acgggcgactcatgtcgaagttgacgaatataaag tacataacgtgtttagaatacccagaatccgaata gtccgcgggggcgtcttctcgcgtgagtaccaaat actgagttgaacttgaaaatgctaaatctgtgaca ctctttgtgtgatgattattgtcaccacttcgaag atggcttcgacattcatgatgttctggtgtttgtt tggaatcgtaatagcgcttgtttcgtccaagtctg acaacaaagaaaatctgaagaattatatcacggat aagtcaaccaatattagaatacccacgccattatt tgtatcaacggaaaactcttatcccacaaaacatg taatctacgatgaaaactgtggcttcgctgtactc aatcctataagtgaccccaaatatgtccttttgag ccagcttctaatgggaaggcgcaaatatgatgcga cggtcgcgtggtttgttctcggtaaaatgtgtgcc agattaatatatttgcgcgaattttataactgctc gacaaatgagccttttggcacatgttctatgagct ctcctggatggtgggacaggcgctacgtctcaacc agtttcatttctcgcgacgaattacagctggtttt tgcagcgccgtcccgagaattagatggtttatata cgcgcgtagtagttgtcaacggggactttactacg gccgatataatgtttaatgttaaagtggcatgtgc cttttcaaagactggaatagaagatgatacattat gcaaaccctttcatttctttgccaatgcaacattg cacaatttaaccatgattagatcggtaactcttcg agcgcacgaaagccatttaaaggaatgggtggcac ggagaggtggtaacgtccctgcagtgctacttgag tctaccatgtatcatgcatccaatctgcctagaaa tttcagggatttctacataaagtctccagatgatt ataagtataatcacctagatgggccatctgtaatg ctcatcactgacagacctagtgaagatttggatgg gaggctcgttcaccaaagtgacatttttactacta caagtcctataaaacaggtccggtatgaagagcat cagtcacatacaaagcagtatcctgtaaacaaaat acaagctataatttttttgatagggttaggctcgt tcattggaagcatattcgtagttttggtagtatgg attatacgcagatattgcaatggagcgcggagtgg gggaacgcccccccagtcctcgccggtatgtgtata -continued ccaggctatgatcacgtgtgaaacttgggcggacc tgtatcatatgtacaccgtccctattcgtttatag ccagtacgtgttatctgcacatagaggaacatgtg tcatactgggatcgcatgcatggtatgtgtgactc taatattattctgtatcataataaaaacacagtgc atggtatatagaggatcgctggtaagcactacggt agaccaatcggctcagattgcattctttggcatcg ataccgttgttaatttatatggcaaagtcttgttc atgggagatcagtatttggaggaaatatactctgg aacgatggaaatactcaaatggaatcaagctaacc gctgctattctattgcgcatgcaacatattacgcc gactgtcctataatcagttctacggtattcagagg atgccgggacgccgttgtttatactaggccccaca gcagaattc SEQ ID NO 17: 1386-04.4#1 (ILT/hCMV IEpro-VP2-HSV TKpA/HVT) (13017 bp) (ILT + IBDV gene cassettes in HVT EcoRI#7 fragment. Virus no. HVT/ILT/IBDV 1386-48.3.1.7)

gaattccagactaaatgccccggcccaatttgtca agtgtgcagtcacggaggcgtcgaccgtgtccccg gcattaaacaggaaagcgttaaagtttttgaatgt taggtcacaggtacaaacataaatgtttgtacaaa caggtaacaggtacaaacataaatgccccggcata aatgtcccttacggcggatcgaaacgacattaggc atactcgggtaccattttgcattccgatcagcacg gatgaaattaggcaggaatgcggtttatattatgc ggcattggacaaacgatatggcattgattggcagt ttatgaatgtcttcatgttgggcgtaaacggattc ctattggttcagaagacaacgacgatatatttaga gagaaaaagctacccagcataggataaacacacat tgagcattgagagacataggtatcggtatggatgg gaaaactacacacgtgaacaccaaacgacttatat actcgagcggtgatactactgagcaagaatgcact gcatctgagccactgaatgaagactgtgatgaaaa tgtgaccatcgatggaattggagaagaatatgcgc agttcttcatgtccccgcaatgggtcccaaatcta catcgcttgagcgaggataccaaaaaggtataccg atgtatggtttccaacagactcaattattttccct attatgaggcgttcaggcggtctttgtttgatatg tatatgctaggtcggttggggcgtcgacttaagcg atctgactgggagactattatgcatctgtcaccaa cgcaaagtcggcgtctacatagaactttaagattt -continued gtggagcgtagaattatcccatctaacagttatat
acgcacatcgggccacgttccgccttcgagggcac
ttccgacagatacgaatttaaagatggatgaataa
ttaaattggaaagagtaactacattaatcgagcgt
catgacggcgtcccgtgaaaatgggaattttctac
tcgaaacaccgtgacatttgacagacctggaattg
ttattctgatatatagtgggtgtgtctggccggca
acatacataatgtgcatgcgaaaccactttttcag
tgtacgctgacattgtgcaacacggaggggtagca
tctacatacaatatatgttgattaatgattggaga
aaaaactatgcagctcgccgatcatatggctaact
cgccttcgtctatatggcggaccccgcgggaaaaa
tcgacgtaccatctgatttacaacaccagtaatga
acatgtcgcatccctgcccagatctgtgcgcccat
tggcgcggatcgttgtgaatgccgccgaaacactt
caggtcggtatgagagccgggaggccgccatcagc
aggagtttggcgagaggtgtttgatagaatgatga
cagccttccgtgaccacgagcctactgcgacattt
aatgctgcaaatcccattagaaaaatggtcgagac
agttctacagaataatgaagagcccccgcggacgc
atgctgaaatgggtaatcgccttatgaacattatg
tactggtgttgcttgggacacgcaggacaatgctc
gatatggcagttgtacgagacgaatcaggccattt
taagtttattagatgaagtggttatcggcacaaca
aatccctttttgcaccctcgagcaatactggaagcc
attatgcaccgcaatcgccaacaaggggacctcat
cgcttgttgaggatgccaaagtggccgagtacctg
gttagcatgcgcaaattgatataacataggcacgc
tctgatgttacagaccacaataccgcatacattta
ttgtaaggttgttaataaaggtttattctatgtaa
gactacaatactttcgacattgcttgtatacatat
taaatactttctcaagttcctattacataaaatgg
gatctatcattacattcgttaagagtctggataat
tttactgtttgccagcttcgatcttggaacgtact
gtggatagtgccttacttggaatcgtgaaaatttg
aaacgtccattatttggatatcttccggttgtccc
atatcccgccctggtaccgctcggataccttgccc
gtatggattcgtattgacagtcgcgcaatcgggga
ccaacaacgcgtgggtccacactcattcggaaatt
ttccgatgattctgaatatttattgccgctcgtta -continued cgagtcgttggacatatctgtaatacatttcttct
tctgaaggatcgctgcacatttgatctatacattg
gccaggatgttcaagtctcagatgttgcattctgg
cacagcacaactttatggcatttccgatgtaatcg
tccggcagccctgggggagttctatattcgcatat
tgggatggtaaggacaatagcagatctcgcaacct
ccagggaggctataataacgtttttaaaggatgga
tttctcataaaaatctgtcgcaaattacactgaga
atatcctttactagcgccgattgagagcatcgtcg
tccaattttctaaatggaaagaaaacaaggcgggc
aagagtgttccaaacattttcattttcggcgaatc
tctcaaatcccatggcgtgcaattgattgcaaaat
tggcacttccgttcacgtttgtatctccaaactct
aagacacttttaattgaaaaactacgttctagtgt
ggaaagaaacctataggcagaccatagaactattt
gacaccacatatctttttgtatgtcaaactgacca
tgatcgtatgttgctgaatgcactagggcaattcg
ctcgcgcgactccatacattgaataattccacacg
tcagctcatcggttagcaaggtccagtagttgaag
tcatttatttttccccgcggctggccaaatctacc
tctgggaatatccaagttgtcgaatatgatcgcac
cggctctggtcatggtgaaggaactgtagcataaa
gacgcaggtatcataggggtaatatttttttattc
actcacatactaaaagtaacgcatattagcaccat
gtatgggctatcaattgacatttgcgtagcactac
atcacgattatgtacaacataatgggacaacatat
ggcaagtagatgcaatttcctcacactagttgggt
ttatctactattgaattttcccctatctgtgatac
acttgggagcctctacaagcatattgccatcatgt
acgtttttatctactgtcttaacgcccatgggaac
ggaggcgtcgtcgtcatgtattggacggcaacata
ggcagcaacacaaattgcgtttaggtggggtgcat
gtggactcgataccaagcccctgcagctggggaac
gtctggtggagagccgataatttgatatacgcacg
ccatattactgtcgttgaagtacgccttatcttct
atgttttcaaatttaggttcccaagtggacgtgag
aagtgtttgtatctcacatggaatggcccaaggca
ttccagcccaggtgcctggtactttaatggcaaac
aaacgttttggtagaggtattgattctattgcagt
tctgcagatatctgcagccccgagtatccacaggc
tatacgatacgttatcggaggcaagcttgttaatt -continued aagtcgacggcagagtcgcagacgcccctattgga
cgtcaaaattgtagaggtgaagttttcaaacgatg
gcgaagtaacggcgacttgcgtttccaccgtcaaa
tctccctatagggtagaaactaattggaaagtaga
cctcgtagatgtaatggatgaaatttctgggaaca
gtcccgccggggtttttaacagtaatgagaaatgg
cagaaacagctgtactacagagtaaccgatggaag
aacatcggtccagctaatgtgcctgtcgtgcacga
gccattctccggaaccttactgtcttttcgacacg
tctcttatagcgagggaaaaagatatcgcgccaga
gttatactttacctctgatccgcaaacggcatact
gcacaataactctgccgtccggcgttgttccgaga
ttcgaatggagccttaataatgtttcactgccgga
atatttgacggccacgaccgttgtttcgcataccg
ctggccaaagtacagtgtggaagagcagcgcgaga
gcaggcgaggcgtggatttctggccggggaggcaa
tatatacgaatgcaccgtcctcatctcagacggca
ctcgcgttactacgcgaaaggagaggtgcttaaca
aacacatggattgcggtggaaaacggtgctgctca
ggcgcagctgtattcactcttttctggacttgtgt
caggattatgcgggagcatatctgctttgtacgca
acgctatggaccgccatttatttttgaggaatgct
ttttggactatcgtactgctttcttccttcgctag
ccagagcaccgccgccgtcacgtacgactacattt
taggccgtcgcgcgctcgacgcgctaaccataccg
gcggttggcccgtataacagatacctcactagggt
atcaagaggctgcgacgttgtcgagctcaacccga
tttctaacgtggacgacatgatatcggcggccaaa
gaaaaagagaagggggccctttcgaggcctccgt
cgtctggttctacgtgattaagggcgacgacggcg
aggacaagtactgtccaatctatagaaaagagtac
agggaatgtggcgacgtacaactgctatctgaatg
cgccgttcaatctgcacagatgtgggcagtggact
atgttcctagcacccttgtatcgcgaaatggcgcg
ggactgactatattctcccccactgctgcgctctc
tggccaatacttgctgaccctgaaaatcgggagat
ttgcgcaaacagctctcgtaactctagaagttaac
gatcgctgtttaaagatcgggtcgcagcttaactt
tttaccgtcgaaatgctggacaacagaacagtatc
agactggatttcaaggcgaacacctttatccgatc -continued gcagacaccaatacacgacacgcggacgacgtata
tcggggatacgaagatattctgcagcgctggaata
atttgctgaggaaaaagaatcctagcgcgccagac
cctcgtccagatagcgtcccgcaagaaattcccgc
tgtaaccaagaaagcggaagggcgcaccccggacg
cagaaagcagcgaaaagaaggcccctccagaagac
tcggaggacgacatgcaggcagaggcttctggaga
aaatcctgccgccctccccgaagacgacgaagtcc
ccgaggacaccgagcacgatgatccaaactcggat
cctgactattacaatgacatgcccgccgtgatccc
ggtggaggagactactaaaagttctaatgccgtct
ccatgcccatattcgcggcgttcgtagcctgcgcg
gtcgcgctcgtggggctactggtttggagcatcgt
aaaatgcgcgcgtagctaatcgagcctagaatagg
tggtttcttcctacatgccacgcctcacgctcata
atataaatcacatggaatagcataccaatgcctat
tcattgggacgttcgaaaagcatggcatcgctact
tggaactctggctctccttgccgcgacgctcgcac
ccttcggcgcgatgggaatcgtgatcactggaaat
cacgtctccgccaggattgacgacgatcacatcgt
gatcgtcgcgcctcgccccgaagctacaattcaac
tgcagctatttttcatgcctggccagagaccccac
aaaccctactcaggaaccgtccgcgtcgcgtttcg
gtctgatataacaaaccagtgctaccaggaactta
gcgaggagcgctttgaaaattgcactcatcgatcg
tcttctgtttttgtcggctgtaaagtgaccgagta
cacgttctccgcctcgaacagactaaccggacctc
cacacccgtttaagctcactatacgaaatcctcgt
ccgaacgacagcgggatgttctacgtaattgttcg
gctagacgacaccaaagaacccattgacgtcttcg
cgatccaactatcggtgtatcaattcgcgaacacc
gccgcgactcgcggactctattccaaggcttcgtg
tcgcaccttcggattacctaccgtccaacttgagg
cctatctcaggaccgaggaaagttggcgcaactgg
caagcgtacgttgccacggaggccacgacgaccag
cgccgaggcgacaaccccgacgcccgtcactgcaa
ccagcgcctccgaacttgaagcggaacactttacc
tttccctggctagaaaatggcgtggatcattacga
accgacacccgcaaacgaaaattcaaacgttactg
tccgtctcgggacaatgagccctacgctaattggg
gtaaccgtggctgccgtcgtgagcgcaacgatcgg -continued cctcgtcattgtaatttccatcgtcaccagaaaca tgtgcaccccgcaccgaaaattagacacggtctcg caagacgacgaagaacgttcccaaactagaaggga atcgcgaaaatttggacccatggttgcgtgcgaaa taaacaagggggctgaccaggatagtgaacttgtg gaactggttgcgattgttaacccgtctgcgctaag ctcgcccgactcaataaaaatgtgattaagtctga atgtggctctccaatcatttcgattctctaatctc ccaatcctctcaaaaggggcagtatcggacacgga ctgggaggggcgtacacgatagttatatggtacag cagaggcctctgaacacttaggaggagaattcagc cggggagagcccctgttgagtaggcttgggagcat attgcaggatgaacatgttagtgatagttctcgcc tcttgtcttgcgcgcctaacttttgcgacgcgaca cgtcctctttttggaaggcactcaggctgtcctcg gggaagatgatcccagaaacgttccggaagggact gtaatcaaatggacaaaagtcctgcggaacgcgtg caagatgaaggcggccgatgtctgctcttcgccta actattgctttcatgatttaatttacgacggagga aagaaagactgcccgcccgcgggacccctgtctgc aaacctggtaattttactaaagcgcggcgaaagct taggtcaattccctggcattatgcccagtacatga ccttatgggactttcctacttggcagtacatctac gtattagtcatcgctattaccatggtgatgcggtt ttggcagtacatcaatgggcgtggatagcggtttg actcacggggatttccaagtctccaccccattgac gtcaatgggagtttgttttggcaccaaaatcaacg ggactttccaaaatgtcgtaacaactccgccccat tgacgcaaatgggcggtaggcgtgtacggtgggag gtctatataagcagagctcgtttagtgaaccgtca gatcgcctggagacgccatccacgctgttttgacc tccatagaagacaccgggcgcgccggatctatgac aaacctgcaagatcaaacccaacagattgttccgt tcatacggagccttctgatgccaacaaccggaccg gcgtccattccggacgacaccctggagaagcacac tctcaggtcagagacctcgacctacaatttgactg tgggggacacagggtcagggctaattgtctttttc cctggattccctggctcaattgtgggtgctcacta cacactgcagagcaatgggaactacaagttcgatc agatgctcctgactgcccagaacctaccggccagc -continued tacaactactgcagactagtgagtcggagtctcac agtgaggtcaagcacactccctggtggcgtttatg cactaaacggcaccataaacgccgtgaccttccaa ggaagcctgagtgaactgacagatgttagctacaa tgggttgatgtctgcaacagccaacatcaacgaca aagttgggaatgtcctggtaggggaaggggtcact gtcctcagcctacccacatcatatgatcttgggta tgtgaggcttggtgaccccattcccgctatagggc ttgacccaaaaatggtagctacatgcgacagcagt gacaggcccagagtctacaccataactgcagccga tgattaccaattctcatcacagtaccaaccaggtg gggtaacaatcacactgttctcagccaacattgat gctatcacaagcctcagcattgggggagagctcgt gtttcaaacaagcgtccaaggccttgtactgggcg ccaccatctaccttataggctttgatgggactgcg gtaatcaccagagctgtggccgcagataatgggct gacggccggcaccgacaatcttatgccattcaatc ttgtcattccaaccaatgagataacccagccgatc acatccatcaaactggagatagtgacctccaaaag tggtggtcaggcaggggatcagatgtcatggtcgg caagtgggagcctagcagtgacgatccatggtggc aactatccaggggccctccgtcccgtcacactagt agcctacgaaagagtggcaacaggatccgtcgtta cggtcgctggggtgagtaacttcgagctgatccca aatcctgaactagcaaagaacctggttacagaata cggccgatttgacccaggagccatgaactacacaa aattgatactgagtgagagggaccgtcttggcatc aagaccgtctggccaacaagggagtacactgattt tcgtgagtacttcatggaggtggccgacctcaact ctcccctgaagattgcaggagcatttggcttcaaa gacataatccgggctataaggaggtaagatccata attgattgacgggagatgggggaggctaactgaaa cacggaaggagacaataccggaaggaacccgcgct atgacggcaataaaaagacagaataaaacgcacgg gtgttgggtcgtttgttcataaacgcggggttcgg tcccagggctggcactctgtcgataccccaccgag accccattggggccaatacgcccgcgtttcttcct tttccccaccccaccccccaagttcgggtgaaggc ccagggctcgcagccaacgtcggggcggcaggccc tgccatagccactggccccgtgggttagggacggg gtcccccatggggaatggtttatggttcgtggggg -continued ttattattttgaagcttgcctccgattctagcatt
acatagccggtcagtagatcctgccattcggtagc
gcaaccggctacatcttcaaacagtctcacaataa
atgcatctctcgttcctgccaatccggaaccgggc
ataccactcccgcctgccgatttaattctcacaat
tgggcgatgccggcggggcaaaacgaatgtggatt
tggcaaaccgacacaggtctgctgtacggactaat
atgggcacacccacatcattcttcagatgctccat
gcattgttctatgagaaagatccatagggtggagg
cagcgtcacgagatcgcccaggcaatcgatcgcat
tcgtctagtaaagtgacgagagttatcatgcacac
acccatgcccacgccttccgaataactggagctgt
ggaagatcggaaacgtctttttgactgccggtctc
gtactactttcgcacaggtgtatacccggacgcgt
actatatattttatatcatccaacgtccgaaatta
catacgtggcggcgatggaagtagatgttgagtct
tcgaaagtaagtgcctcgaatatgggtattgtctg
tgaaaatatcgaaagcggtacgacggttgcagaac
cgtcgatgtcgccagatactagtaacaatagcttc
gataacgaagacttccgtgggcctgaatacgatgt
ggagataaataccagaaaatctgctaatcttgatc
gtatggaatcttcgtgccgtgaacaacgagcggcg
tgcgaacttcgaaagtgttcgtgtcctacgtctgc
cgtgcgcatgcaatacagtattctttcatctctcg
ctccgggttcagagggtcatgtatatatatgtact
agatacggggacgcggaccaaaaaaaatgcatagt
gaaggcagtcgttggaggaaagaatcccgggaggg
aagtggatattttaaaaaccatctcacataaatca
attataaaattaatccatgcctataaatggaaaaa
tgttgtgtgtatggcaatgcgtgtatatcgttatg
atcttttcacatatattgacggagtcggccctatg
ccccttcaacagatgatctatattcaacgtggact
actagaggcgctagcatacatacatgaaaggggca
tcattcaccgagacgtaaagacggagaatatattc
ttggataatcacgaaaatgcagttttgggtgactt
cggtgctgcatgccaactaggagattgtatagata
cgccccaatgttacggttggagcggaactgtggaa
acaaattcgccggaattatctgcacttgatccgta
ttgcacaaaaacagatatttggagtgccggattgg
ttctatatgagatggcaattaaaaatgtaccattg -continued tttagtaagcaggtgaaaagttcgggatctcagct
gagatccataatacggtgcatgcaagtgcatgaac
tggagtttccccgcaacgattctaccaacctctgt
aaacatttcaaacaatatgcggttcgtgtacgacc
gccttataccattcctcgagttataagaaatgggg
ggatgccaatggatgttgaatatgtcatttctaaa
atgcttacgtttgaccaggagttcagaccttctgc
taaggaaatattgaatatgcccctatttactaagg
cgccgattaacctgcttaatatcacaccctctgac
agtgtctaacggtatacaggcgggagcgggtcgtg
gcgtcatcatcaccacttgagaatttatattttga
attgttgattgataaattaacctgattcattgaga
actgaaacgccatattggtttcttggatatgtcta
caacaattagttaaattgctatgttctactgcgag
taacatttgataagttgtaagagacgggcgactca
tgtcgaagttgacgaatataaagtacataacgtgt
ttagaatacccagaatccgaatagtccgcgggggc
gtcttctcgcgtgagtaccaaatactgagttgaac
ttgaaaatgctaaatctgtgacactctttgtgtga
tgattattgtcaccacttcgaagatggcttcgaca
ttcatgatgttctggtgtttgtttggaatcgtaat
agcgcttgtttcgtccaagtctgacaacaaagaaa
atctgaagaattatatcacggataagtcaaccaat
attagaatacccacgccattatttgtatcaacgga
aaactcttatcccacaaaacatgtaatctacgatg
aaaactgtggcttcgctgtactcaatcctataagt
gaccccaaatatgtccttttgagccagcttctaat
gggaaggcgcaaatatgatgcgacggtcgcgtggt
ttgttctcggtaaaatgtgtgccagattaatatat
ttgcgcgaattttataactgctcgacaaatgagcc
ttttggcacatgttctatgagctctcctggatggt
gggacaggcgctacgtctcaaccagtttcatttct
cgcgacgaattacagctggtttttgcagcgccgtc
ccgagaattagatggtttatatacgcgcgtagtag
ttgtcaacggggactttactacggccgatataatg
tttaatgttaaagtggcatgtgccttttcaaagac
tggaatagaagatgatacattatgcaaaccctttc
atttctttgccaatgcaacattgcacaatttaacc
atgattagatcggtaactcttcgagcgcacgaaag
ccatttaaaggaatgggtggcacggagaggtggta
acgtccctgcagtgctacttgagtctaccatgtat -continued catgcatccaatctgcctagaaatttcagggattt ctacataaagtctccagatgattataagtataatc acctagatgggccatctgtaatgctcatcactgac agacctagtgaagatttggatgggaggctcgttca ccaaagtgacattttactactacaagtcctataa aacaggtccggtatgaagagcatcagtcacataca aagcagtatcctgtaaacaaaatacaagctataat tttttgatagggttaggctcgttcattggaagca tattcgtagttttggtagtatggattatacgcaga tattgcaatggagcgcggagtgggggaacgccccc cagtcctcgccggtatgtgtataccaggctatgat cacgtgtgaaacttgggcggacctgtatcatatgt acaccgtccctattcgtttatagccagtacgtgtt atctgcacatagaggaacatgtgtcatactgggat cgcatgcatggtatgtgtgactctaatattattct gtatcataataaaaacacagtgcatggtatataga ggatcgctggtaagcactacggtagaccaatcggc tcagattgcattctttggcatcgataccgttgtta atttatatggcaaagtcttgttcatgggagatcag tatttggaggaaatatactctggaacgatggaaat actcaaatggaatcaagctaaccgctgctattcta ttgcgcatgcaacatattacgccgactgtcctata atcagttctacggtattcagaggatgccgggacgc cgttgtttatactaggccccacagcagaattc SEQ ID NO 18: 484-1050-2641-10859
(mCMV IEpro-VP2-SV40pA/ILT/HVT)
(15252 bp)
(IBDV + ILT gene cassettes
in HVT Asci fragment.) Virus no.
HVT/IBDV/ILT 484
ggcgcgccactggagaacggcatgaccgcaaaagg cgttgtagagatcgatcccacgaactctcaggcga tcgtgtcagtcgccataaacagcgacgatcgtctc caggatctgaacggttttcttctcaacgatcatca gtatatgaggaactgaacctgatatttagccgagg gaaacgcaggttaaaaaccctatcaagcgattgcg attttcgcgtatctagtaaaaatagatgggcttcg gtactagccttcgccgccaactctgaatatgccct tcgtggacctcatataacatggcattgtttgttgg atgcggggccggaattaagaagaacattcgaaata cgagcaaaaatttcggccctggcatgtgctgcgcg agaatcggtacttcggggagaaagttttatcggag ctttgggtagtgcagaggaaactctatcttggttg -continued aaaatgcatgcgaccctgcacttgattctggttaa ccacgatccaatttttaagacggctggcgcggtcc tagataacctccgcttaaaactagccccaatattg atgtgcagatataacacagaaaaacgatcaatgga agacatgctacggcggtcatctcccgaagacatca ccgattccctaacaatgtgcctgattatgttatcg cgcattcgtcgtaccatgcgcaccgcaggaaataa atatagctatatgatagatccaatgaatcgtatgt ctaattacactccaggcgaatgtatgacaggtata ttgcgatatattgacgaacatgctagaaggtgtcc tgatcacatatgtaatttgtatatcacatgtacac ttatgccgatgtatgtgcacgggcgatatttctat tgtaattcatttttttgttagtaaactaccacagg ctgtccggaaatctaagttaatgaataaagtagat ggttaatactcattgcttagaattggactactttt aattctctttaatgttcgtattaaataaaaacatc tttaataaacttcagcctcttcgcttattgtagaa attgagtattcaaaatcatgttcaaagccgtcttc ggagagtgtactcgccacggtggttggaacatcac tatgtctacacgtcaaatttaagcacgtcaggtct gtcgaggacaagaaatggttaactagtgtttcaat tattcttataaacgttaagcattgtaagcccccg gccgtccgcagcaacaatttactagtatgccgtgg gctccgggactatcacggatgtccaattcgcacat gcatataatttttctagggtctctcatttcgagaa atcttcggggatccatcagcaatgcgggctgtagt cccgattcccgtttcaaatgaaggtgctccaacac ggtcttcaaagcaaccggcataccagcaaacacag actgcaactccccgctgcaatgattggttataaac agtaatctgtcttctggaagtatatttcgcccgac aatccacggcgcccccaaagttaaaaaccatccat gtgtatttgcgtcttctctgttaaaagaatattga ctggcattttcccgttgaccgccagatatccaaag tacagcacgatgttgcacggacgactttgcagtca ccagccttcctttccaccccccccaccaacaaaatg tttatcgtaggacccatatccgtaataaggatggg tctggcagcaaccccataggcgcctcggcgtggta gttctcgaggccttaagcttaaggatcccccaact ccgcccgttttatgactagaaccaatagtttttaa tgccaaatgcactgaaatcccctaatttgcaaagc caaacgccccctatgtgagtaatacggggactttt -continued tacccaatttcccacgcggaaagcccccctaataca ctcatatggcatatgaatcagcacggtcatgcact ctaatggcggcccatagggactttccacatagggg gcgttcaccatttcccagcataggggtggtgactc aatggcctttacccaagtacattgggtcaatggga ggtaagccaatgggtttttcccattactggcaagc acactgagtcaaatgggactttccactgggttttg cccaagtacattgggtcaatgggaggtgagccaat gggaaaaacccattgctgccaagtacactgactca atagggactttccaatgggtttttccattgttggc aagcatataaggtcaatgtgggtgagtcaataggg actttccattgtattctgcccagtacataaggtca ataggggtgaatcaacaggaaagtcccattggag ccaagtacactgcgtcaatagggactttccattgg gttttgcccagtacataaggtcaataggggatgag tcaatgggaaaaacccattggagccaagtacactg actcaatagggactttccattgggttttgcccagt acataaggtcaataggggggtgagtcaacaggaaag ttccattggagccaagtacattgagtcaataggga ctttccaatgggttttgcccagtacataaggtcaa tgggaggtaagccaatgggtttttcccattactgg cacgtatactgagtcattagggactttccaatggg ttttgcccagtacataaggtcaataggggtgaatc aacaggaaagtcccattggagccaagtacactgag tcaatagggactttccattgggttttgcccagtac aaaaggtcaataggggggtgagtcaatgggtttttc ccattattggcacgtacataaggtcaataggggtg agtcattgggtttttccagccaatttaattaaaac gccatgtactttcccaccattgacgtcaatgggct attgaaactaatgcaacgtgacctttaaacggtac tttcccatagctgattaatgggaaagtaccgttct cgagccaatacacgtcaatgggaagtgaaagggca gccaaaacgtaacaccgccccggttttcccctgga aattccatattggcacgcattctattggctgagct gcgttctacgtgggtataagaggcgcgaccagcgt cggtaccgtcgcagtcttcggtctgaccaccgtag aacgcagagctcctcgctgcaggcggccgctctag aactcgtcgatcgcagcgatgacaaacctgcaaga tcaaacccaacagattgttccgttcatacggagcc ttctgatgccaacaaccggaccggcgtccattccg -continued gacgacaccctggagaagcacactctcaggtcaga gacctcgacctacaatttgactgtgggggacacag ggtcagggctaattgtctttttccctggattccct ggctcaattgtgggtgctcactacacactgcagag caatgggaactacaagttcgatcagatgctcctga ctgcccagaacctaccggccagctacaactactgc agactagtgagtcggagtctcacagtgaggtcaag cacactccctggtggcgtttatgcactaaacggca ccataaacgccgtgaccttccaaggaagcctgagt gaactgacagatgttagctacaatgggttgatgtc tgcaacagccaacatcaacgacaaaattgggaatg tcctggtaggggaaggggtcactgtcctcagccta cccacatcatatgatcttgggtatgtgaggcttgg tgaccccattcccgctatagggcttgacccaaaaa tggtagctacatgcgacagcagtgacaggcccaga gtctacaccataactgcagccgatgattaccaatt ctcatcacagtaccaaccaggtggggtaacaatca cactgttctcagccaacattgatgctatcacaagc ctcagcattgggggagagctcgtgtttcaaacaag cgtccaaggccttgtactgggcgccaccatctacc ttataggctttgatgggactgcggtaatcaccaga gctgtggccgcagataatgggctgacggccggcac cgacaatcttatgccattcaatcttgtcattccaa ccaatgagataacccagccaatcacatccatcaaa ctggagatagtgacctccaaaagtggtggtcaggc aggggatcagatgtcatggtcggcaagtgggagcc tagcagtgacgatccatggtggcaactatccaggg gccctccgtcccgtcacactagtagcctacgaaag agtggcaacaggatccgtcgttacggtcgctgggg tgagtaacttcgagctgattccaaatcctgaacta gcaaagaacctggttacagaatacggccgatttga cccaggagccatgaactacacaaaattgatactga gtgagagggaccgtcttggcatcaagaccgtctgg ccaacaagggagtacactgattttcgtgagtactt catggaggtggccgacctcaactctcccctgaaga ttgcaggagcatttggcttcaaagacataatccgg gctataaggaggtagatccagacatgataagatac attgatgagtttggacaaaccacaactagaatgca gtgaaaaaaatgctttatttgtgaaatttgtgatg ctattgctttatttgtaaccattataagctgcaat aaacaagttaacaacaacaattgcattcattttat -continued gtttcaggttcagggggaggtgtgggaggtttttt
cggatcctctagagtcgacggcagagtcgcagacg
cccctattggacgtcaaaattgtagaggtgaagtt
ttcaaacgatggcgaagtaacggcgacttgcgttt
ccaccgtcaaatctccctatagggtagaaactaat
tggaaagtagacctcgtagatgtaatggatgaaat
ttctgggaacagtcccgccggggtttttaacagta
atgagaaatggcagaaacagctgtactacagagta
accgatggaagaacatcggtccagctaatgtgcct
gtcgtgcacgagccattctccggaaccttactgtc
ttttcgacacgtctcttatagcgagggaaaaagat
atcgcgccagagttatactttacctctgatccgca
aacggcatactgcacaataactctgccgtccggcg
ttgttccgagattcgaatggagccttaataatgtt
tcactgccggaatatttgacggccacgaccgttgt
ttcgcataccgctggccaaagtacagtgtggaaga
gcagcgcgagagcaggcgaggcgtggatttctggc
cggggaggcaatatatacgaatgcaccgtcctcat
ctcagacggcactcgcgttactacgcgaaaggaga
ggtgcttaacaaacacatggattgcggtggaaaac
ggtgctgctcaggcgcagctgtattcactcttttc
tggacttgtgtcaggattatgcgggagcatatctg
ctttgtacgcaacgctatggaccgccatttatttt
tgaggaatgctttttggactatcgtactgctttct
tccttcgctagccagagcaccgccgccgtcacgta
cgactacattttaggccgtcgcgcgctcgacgcgc
taaccataccggcggttggcccgtataacagatac
ctcactagggtatcaagaggctgcgacgttgtcga
gctcaacccgatttctaacgtggacgacatgatat
cggcggccaaagaaaaagagaaggggggcccctttc
gaggcctccgtcgtctggttctacgtgattaaggg
cgacgacggcgaggacaagtactgtccaatctata
gaaaagagtacagggaatgtggcgacgtacaactg
ctatctgaatgcgccgttcaatctgcacagatgtg
ggcagtggactatgttcctagcacccttgtatcgc
gaaatggcgcgggactgactatattctcccccact
gctgcgctctctggccaatacttgctgaccctgaa
aatcgggagatttgcgcaaacagctctcgtaactc
tagaagttaacgatcgctgtttaaagatcgggtcg
cagcttaactttttaccgtcgaaatgctggacaac -continued agaacagtatcagactggatttcaaggcgaacacc
tttatccgatcgcagacaccaatacacgacacgcg
gacgacgtatatcggggatacgaagatattctgca
gcgctggaataatttgctgaggaaaaagaatccta
gcgcgccagaccctcgtccagatagcgtcccgcaa
gaaattcccgctgtaaccaagaaagcggaagggcg
caccccggacgcagaaagcagcgaaaagaaggccc
ctccagaagactcggaggacgacatgcaggcagag
gcttctggagaaaatcctgccgccctccccgaaga
cgacgaagtccccgaggacaccgagcacgatgatc
caaactcggatcctgactattacaatgacatgccc
gccgtgatcccggtggaggagactactaaaagttc
taatgccgtctccatgcccatattcgcggcgttcg
tagcctgcgcggtcgcgctcgtggggctactggtt
tggagcatcgtaaaatgcgcgcgtagctaatcgag
cctagaataggtggtttcttcctacatgccacgcc
tcacgctcataatataaatcacatggaatagcata
ccaatgcctattcattgggacgttcgaaaagcatg
gcatcgctacttggaactctggctctccttgccgc
gacgctcgcacccttcggcgcgatgggaatcgtga
tcactggaaatcacgtctccgccaggattgacgac
gatcacatcgtgatcgtcgcgcctcgccccgaagc
tacaattcaactgcagctatttttcatgcctggcc
agagaccccacaaaccctactcaggaaccgtccgc
gtcgcgtttcggtctgatataacaaaccagtgcta
ccaggaacttagcgaggagcgctttgaaaattgca
ctcatcgatcgtcttctgtttttgtcggctgtaaa
gtgaccgagtacacgttctccgcctcgaacagact
aaccggacctccacacccgtttaagctcactatac
gaaatcctcgtccgaacgacagcgggatgttctac
gtaattgttcggctagacgacaccaaagaacccat
tgacgtcttcgcgatccaactatcggtgtatcaat
tcgcgaacaccgccgcgactcgcggactctattcc
aaggcttcgtgtcgcaccttcggattacctaccgt
ccaacttgaggcctatctcaggaccgaggaaagtt
ggcgcaactggcaagcgtacgttgccacggaggcc
acgacgaccagcgccgaggcgacaaccccgacgcc
cgtcactgcaaccagcgcctccgaacttgaagcgg
aacactttacctttccctggctagaaaatggcgtg
gatcattacgaaccgacacccgcaaacgaaaattc
aaacgttactgtccgtctcgggacaatgagcccta -continued cgctaattggggtaaccgtggctgccgtcgtgagc
gcaacgatcggcctcgtcattgtaatttccatcgt
caccagaaacatgtgcaccccgcaccgaaaattag
acacggtctcgcaagacgacgaagaacgttcccaa
actagaagggaatcgcgaaaatttggacccatggt
tgcgtgcgaaataaacaaggggggctgaccaggata
gtgaacttgtggaactggttgcgattgttaacccg
tctgcgctaagctcgcccgactcaataaaaatgtg
attaagtctgaatgtggctctccaatcatttcgat
tctctaatctcccaatcctctcaaaaggggcagta
tcggacacggactgggaggggcgtacacgatagtt
atatggtacagcagaggcctctgaacacttaggag
gagaattcagccggggagagcccctgttgagtagg
cttgggagcatattgcaggatgaacatgttagtga
tagttctcgcctcttgtcttgcgcgcctaactttt
gcgacgcgacacgtcctctttttggaaggcactca
ggctgtcctcggggaagatgatcccagaaacgttc
cggaagggactgtaatcaaatggacaaaagtcctg
cggaacgcgtgcaagatgaaggcggccgatgtctg
ctcttcgcctaactattgctttcatgatttaattt
acgacggaggaaagaaagactgcccgcccgcggga
cccctgtctgcaaacctggtaattttactaaagcg
cggcgaaagcttcccgggttaattaaggccctcga
ggatacatccaaagaggttgagtattctctctaca
cttcttgttaaatggaaagtgcatttgcttgttct
tacaatcggcccgagtctcgttcacagcgcctcgt
tcacacttaaaccacaaatagtctacaggctatat
gggagccagactgaaactcacatatgactaatatt
cgggggtgttagtcacgtgtagcccattgtgtgca
tataacgatgttggacgcgtccttattcgcggtgt
acttgatactatggcagcgagcatgggatattcat
cctcgtcatcgttaacatctctacgggttcagaat
gtttggcatgtcgtcgatcctttgcccatcgttgc
aaattacaagtccgatcgccatgaccgcgataagc
ctgtaccatgtggcattagggtgacatctcgatca
tacattataagaccaacgtgcgagtcttccaaaga
cctgcacgccttcttcttcggattgtcaacgggtt
cttcagaatctatgcccatatctggcgttgagacc
attgtgcgtttaatgaacaataaagcggcatgcca
tggaaaggagggctgcagatctccattttctcacg -continued ccactatcctggacgctgtagacgataattatacc
atgaatatagaggggggtatgtttccactgccactg
tgatgataagttttctccagattgttggatatctg
cattttctgctgccgaacaaacttcatcgctatgc
aaagagatgcgtgtgtacacgcgccggtggagtat
acgggaaactaaatgttcatagaggtctttgggct
atatgttattaaataaaataattgaccagtgaaca
atttgtttaatgttagtttattcaatgcattggtt
gcaaatattcattacttctccaatcccaggtcatt
ctttagcgagatgatgttatgacattgctgtgaaa
attactacaggatatatttttaagatgcaggagta
acaatgtgcatagtaggcgtagttatcgcagacgt
gcaacgcttcgcatttgagttaccgaagtgcccaa
cagtgctgcggttatggtttatgcgcacagaatcc
atgcatgtcctaattgaaccatccgatttttcttt
taatcgcgatcgatgtttgggcaactgcgttattt
cagatctaaaaaatttaccctttatgaccatcaca
tctctctggctcataccccgcttggataagatatc
atgtagattccgccctaagaaatgcaaactaacat
tattgtcggttccatatacacttccatcttgtcct
tcgaaaataacaaactcgcgcaatagaccgtccgt
acatgcatggccgatgtgtgtcaacatcattggtc
tgctagatcccgatgggacgaatcgtacagtcgtc
gctccagcattggcaaaaatccccagatacccctcc
atgcggcaaatctaaattgcgaccccgaagagact
gcaccaaagtcttatcgacgcacgctgattttttt
gaacagcgggagcccattatcttcagtggagcgta
gacgggcgaggctaattatgtgacatagcaacact
gcatgtatgtttttataaatcaataagagtacata
atttattacgtatcatttccgtttgtaatatactg
tatacatcatccacactattagtcagcactagcgc
gcgggcgcacgttacaatagcagcgtgcccgttat
ctatattgtccgatatttacacataacatttcatc
gacatgattaaatacctaagtactgcacacagatg
tttaatgtatatcgtcatataaattatatcgctag
gacagacccaaacgacctttatcccaaacagtcag
atcctcttctcaagtgtcgatttctgttatggaat
atgcataccctggcccagaaattgcacgcacgagc
gtagtgaatgcgtcattggttttacatttaaaggc
taaatgcacaaattctttagacgacagcacatcgt
taaatagcatctctagcgttcttatgaatgctaag -continued cattggagtcctcctggtcggccacaataacagct
gagtatcataccctgagctccggggttgtcgcaca
tagcggattcgtataaacataggattttccgcgaa
tccatcagttgcaaaaatctgttaggctccatcaa
caacgctggatttacttcagatccacgcgtaaagt
aatggtgctcgaataccgtttttagagttgtcggc
atttcaaggaacaaagaattcatttcttcattgca
acgacgcgccagaaatcccaagacctctttgggta
gtatgttcttgcctataaaacacggcgttccaagt
gccaggaaccacgcatgtgttactgttggggcgta
ttcagaaataaagcggggtttatgcggcttttgaa
gctcggatatccaaagtatcgcttgctgatgaacg
agcgatgtagctgttacaaaacctcctttccatcc
tccagtcaacataatatttatcggcctacctatgt
ccgtaataagtattggtcgggcaattattccgtat
gaggtcttgcaggaataagctcttagggacagcca
gcttggatatggtgcgaaacagaccttctcggctt
cagaatgtcgctccgcagtctcttcgtgtcggtgc
atcttagatccaccatcaatgtgtgcagcattgac
tcccgcccgtcgaatattccttttgttacgatgca
gtaatgagcacgatcatgggcggggcgatgacgtt
ctatttgcatgtctgcgaacaatttgcgtcagtca
tacagctatggagtgggccatttctggccgtcaac
ttaaaaacgcgaaccgcagacatatgtatttgcat
gcaaagacgtatcttcgtatttctgggcatcttca
aatgctctggccaatatggcaatgaatttggattc
gtttgacgccgatggtatgcagtgcaaatgtgcca
atagcccacatccgaaaaagttatttgtcatacaa
gcaggtgttaagtagcaatcacataaaggcaccag
acgcctcatggcatcataatgaatagctccttctc
cccactggaaccactgacaaaatctgcgagtatat
tccgcaaaccacatttatttctcatagaaactac
cctaaatccttttaacgggaagaagaatcctagat
agtgcttgaagtcatgactgttactgctgcaataa
cactgtatattatttataaattccgtttgtctagg
tatctgatgtaggcattccgatcccttttactattg
cgtcttcacgaccaaatgggaatgcgccaaaatcc
ccacacctcatcaccctggaggcagattgtgtatt
attaatatccgccgattgaagcacaaaacggtacg
gtactgttcctaattctggtatagattctatggtc -continued aaaagtctgcatatccccgacattgccatgagatc
acacagtccaagtagcatgtttattgagtcactca
gactgtcaacgtccctcgccgcaccaccaatcgaa
aataaagtatctacgcaagttatagctccgcattt
tctatcgctagcagcaatcgcgacgcaaaacataa
aggccatgttgggatttgaactctctggggggctt
gttatcttctgcaccgtcgcagtcgcagttttccg
aaatttatgtctaatatattttccggccgtgctcc
aatcggccgaaaagaatctgcgtattaccagactc
attgacgggccgataaagaccataaaacaaaattc
ctgtgcactccctcctccagttttgccatcgtcca
agtcccgtaactttttttgcgtttcgaggagcaag
cgttcgttatccctacccacacttgttttccaccg
ttttcttattataagcggttgtatcgccaacgcgt
caccgcaggttgtcacatacagtgatggcatactt
gaacgtgcaacaacgcgctcgctttgcaaatctaa
gtcattgaccatcaaatcgcgttgagaggatagcc
aggcatcttttttcctagtatggtgacggtgcagc
caccccaactcagttcttgtaaaaaaagctattgg
cgggaatttatgttctgaggtgcattctatattta
tgagtccatcaaatgccattaaccagattcgtatt
ttttcgctcgacccggcatcactatggatacaata
cctttctatggcccatttcagctctcgaaccaacc
acacggacaattgactaacataagtatgatcttta
tcacagtcgcacccatctgagttatatttatggca
tccgagcgctcttactgtacggtcggatacaccca
tggtttttcctttatatagtcgggttatagtctgt
cgggtttggcggtagcacggagtagtttgattttt
aagaatcgaaaaccggcttggagagaccactgtcg
aatatttgtccgtatactctacacgtgagtgttgt
ccattcctaggtatattcatctgttcggatacctt
caattgctgttcaggcataaccttaaagcatatgt
tatgttgtacatcaaaacttggtgagttatgttcg
attgccgcgcataaagaatcgtacatgagcgtttc
tgctaacatactatctatattctcacacgcccctg
catatactgttcctattccaaattcacgttttgcc
ccatcggctatctgctcccaaaaagttgtaatata
ggtgccgctgggtgcgaaattttcatcagttgtat
tcctgataaactgaatcactttacataatttttgc
cacatatctgcgtgcagccatagtatcgaacccgt
gggctcggagacgacagtgcgtacaatgggtattt -continued taccttttccccaacaaaataatggtatacaagtta ggtccgtacctagaccttaatgtttccaattcttc tgaatcactgcactctcgtaggggagtaacggtaa taatttcgtctctgagccccgttttgcgttgaaaa ctaatcacattagataatgtgcaatcggtttcttt tatccggatacatctaagtattatgacatcggtgg tcattgtttccatcaacgaccatcttttacgatcg cccatactactcatggacgttgtcggtgttgaaaa atcaccagaattgcaacggatctctgggtaccatg ctgctgatggaattggcggttttaattgttgtttc agtctattattgctatctttggcggggttgaataa tgtgggggagagtgattgcaggaatccgaatggg tcaataaaacgaccgtgctccgttctgccggcgcc gatccgattgaagctatatacttcgcttctctccc cacttttccaatttgatccggaaataaaacggccc cggacaacagtatcgtacgatccggatccggatcc tgcttgcctacagaagaatcaacatctcgccccaa tattctggtcaaaactggctcgctcatggcaacgc ggacgtttcccccggtggccagtcttaatggttaa tgttcttttcggcaatcttatacatcagcgggttg cgtgaatactggtcacagttcagtcatttactaca caccagcaatacgacgacggacagtaccgtcccga cgaacgcgacgcccaaaattgctatcgcgaccgcg tccgaggcgatgtcgtacgggcggtgcggggttgg atcctcggcaaagagatcctcgtaattcggcggtg ggagcggagggtaaagacgcgggtggggatctccc tccggaccgcgcgccgggcgcggttcgaaaatgct ttccgcctcgctcagtgtcaacgccaagtattcgg gcgggctgggggccggaatatctcccgcgacttct tctatcggcgcggaattggagtcgcggtcgtggcg cgcttctagcgtcgtcaacggaagtccattttcgg ggtctcccggtgggcgttcagcgtccatcgtcgta tatgctctaacacacgtctcgctatattaaaaaaa agaagagtatcggtcagtgtcgagtgtcgccgaca atgtcgcgagttctcggcgatttaatttttggaac tgctccctatgaatcccgtaactgtagcgcccgcg cagaaagccgccatcagaccaactacgtgtctgtt cgatgtttgcccgccgatcgctttaccgattaagg ttccggcgagaaatgacatgctcgatccaagaaca aagtttttcgcggtaaacaacaacatagttaccgt -continued gcgagatggagaaaccacatctcccgaattagtag aggaaagcccgcgctgtcggtttggggacatatcg atctttttgtgtttttcctaggacccttttgcca gatcgtacaaagtcgcgtcttatgagcggacgttc ttactgcagctcggtaggagtggggcagggttaga tttcgtcggcgtttcggccccccgtatgcgccgcgc caccctcttcgccgagctctttatgcgcggtgggg gtgagcgcttccggagttgcgatctccgatctcga gccgcagcccggcggtgtctctttcagtggagcgt tagcgccatcatgtggttcgtggcggtggaaaggc tattatgtgttaggggagagaccacgtgatcggca tgcaaatgagcaaggcgaacgcgtcagcgttcgca ctgcgaaccaataatatatatattatactattggc tttaggtgcgaacgtccggctagtccaatagcggg gtcgcgtttcgtaccacgtgttatagaccgcccta aactcgcactcgggggtccggccgcgcccagacag ggcggagacgtgccacaggggctttaaaacaccgc ttcgggcaccgttcatctcggcgcgcc SEQ ID NO 19: SV40 polyadenylation signal (199 bp)

agcttcagacatgataagatacattgatgagtttg gacaaaccacaactagaatgcagtgaaaaaaatgc tttatttgtgaaatttgtgatgctattgctttatt tgtaaccattataagctgcaataaacaagttaaca acaacaattgcattcattttatgtttcaggttcag ggggaggtgtgggaggttttttcg The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

It is further to be understood that all base sizes or amino acid sizes, and all molecular weight or molecular mass values, given for nucleic acids or polypeptides are approximate, and are provided for description.

We claim:

1. A recombinant nonpathogenic Marek's Disease Virus (rMDV$_{np}$) comprising a first heterologous nucleic acid located in a first nonessential site in the $rMDV_{np}$ genome and a second heterologous nucleic acid located in a second nonessential site in the $rMDV_{np}$ genome;
   wherein the first heterologous nucleic acid comprises both a nucleotide sequence that encodes an Infectious Laryngotracheitis Virus glycoprotein D (ILTV gD) and a nucleotide sequence that encodes an Infectious Laryngotracheitis Virus glycoprotein I (ILTV gI);
   wherein the second heterologous nucleic acid comprises a nucleotide sequence that encodes an Infectious Bursal Disease Virus viral protein 2 (IBDV VP2);
   wherein the first nonessential site and the second nonessential site are either the same or different; and wherein when the first nonessential site and the second nonessential site are different, one is the US2 site and the other is the UL54.5 site.

2. The $rMDV_{np}$ of claim 1, wherein the first nonessential site and the second nonessential site are the US2 site.

3. The $rMDV_{np}$ of claim 1, wherein the nucleotide sequence encoding the ILTV gD protein is operatively under the control of a first promoter, the nucleotide sequence encoding the ILTV gI protein is operatively under the control of a second promoter, and the nucleotide sequence encoding the IBDV VP2 protein is operatively under the control of a third promoter.

4. The $rMDV_{np}$ of claim 3, wherein the first promoter, the second promoter, and the third promoter are all different.

5. The $rMDV_{np}$ of claim 4, wherein the first promoter is the endogenous ILTV gD promoter, the second promoter is the endogenous ILTV gI promoter, and the third promoter is selected from the group consisting of the murine cytomegalovirus immediate early 1 gene (mCMV-IE1) promoter, the human cytomegalovirus immediate early 1 gene (hCMV-IE1) promoter, and the chicken β-actin promoter.

6. The $rMDV_{np}$ of claim 1, wherein the $rMDV_{np}$ is a recombinant herpesvirus of turkeys (rHVT).

7. The $rMDV_{np}$ of claim 1, wherein the $rMDV_{np}$ is a recombinant Marek's Disease Virus serotype 2 (rMDV2).

8. An immunogenic composition comprising the $rMDV_{np}$ of claim 1.

9. The immunogenic composition of claim 8, wherein the $rMDV_{np}$ is a recombinant herpesvirus of turkeys (rHVT).

10. The immunogenic composition of claim 8, wherein the $rMDV_{np}$ is a recombinant Marek's Disease Virus serotype 2 (rMDV2).

11. A vaccine comprising the immunogenic composition of claim 8.

12. A method for aiding in the protection of a chicken against ILTV and IBDV comprising administering the vaccine of claim 11.

13. A vaccine comprising the immunogenic composition of claim 9.

14. A method for aiding in the protection of a chicken against ILTV and IBDV comprising administering the vaccine of claim 13.

15. The $rMDV_{np}$ of claim 5, wherein the $rMDV_{np}$ is a recombinant herpes virus of turkeys (rHVT).

16. A recombinant herpesvirus of turkeys (rHVT) that comprises a recombinant nucleic acid inserted into a nonessential site comprising in 5' to 3' direction in the following order:
   a murine cytomegalovirus immediate early 1 (mCMV-IE1) promoter;
   (ii) a coding sequence for Infectious Bursal Disease Virus viral protein 2 (IBDV VP2);
   (iii) a transcription terminator sequence;
   (iv) an Infectious Laryngotracheitis Virus glycoprotein D (ILTV gD) promoter;
   (v) a coding sequence for the ILTV gD protein;
   (vi) an Infectious Laryngotracheitis Virus glycoprotein I (ILTV gI) promoter; and
   (vii) a coding sequence for the ILTV gI protein.

17. The rHVT of claim 16, wherein the recombinant nucleic acid comprises the nucleotide sequence of SEQ ID NO: 15; and wherein the nonessential insertion site is the US2 site.

18. The rHVT of claim 16, wherein the nonessential insertion site is selected from the group consisting of US2 and UL54.5.

19. A vaccine comprising the rHVT of claim 17.

20. A method for aiding in the protection of a chicken against ILTV and IBDV comprising administering the vaccine of claim 19.

21. The rHVT of claim 16, wherein the recombinant nucleic acid comprises the nucleotide sequence of SEQ ID NO: 18; and wherein the nonessential insertion site is the UL54.5 site.

22. A vaccine comprising the rHVT of claim 21.

23. The rHVT of claim 16, wherein the nonessential insertion site is the US2 site.

24. A vaccine comprising the rHVT of claim 23.

25. A method for aiding in the protection of a chicken against ILTV and IBDV comprising administering the vaccine of claim 24.

* * * * *